United States Patent
Huryn et al.

(10) Patent No.: US 11,214,560 B2
(45) Date of Patent: Jan. 4, 2022

(54) MODULATORS OF P97 AAA ATPASE ACTIVITY

(71) Applicant: UNIVERSITY OF PITTSBURGH—OF THE COMMONWEALTH SYSTEM OF HIGHER EDUCATION, Pittsburgh, PA (US)

(72) Inventors: Donna M. Huryn, Allentown, PA (US); Peter Wipf, Pittsburgh, PA (US); Matthew G. LaPorte, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/612,342

(22) PCT Filed: May 10, 2018

(86) PCT No.: PCT/US2018/032062
§ 371 (c)(1),
(2) Date: Nov. 8, 2019

(87) PCT Pub. No.: WO2018/209083
PCT Pub. Date: Nov. 15, 2018

(65) Prior Publication Data
US 2020/0216410 A1    Jul. 9, 2020

Related U.S. Application Data

(60) Provisional application No. 62/504,732, filed on May 11, 2017.

(51) Int. Cl.
| | |
|---|---|
| *C07D 401/04* | (2006.01) |
| *C07D 401/14* | (2006.01) |
| *C07D 405/14* | (2006.01) |
| *A61P 35/00* | (2006.01) |
| *A61P 31/18* | (2006.01) |

(52) U.S. Cl.
CPC ......... *C07D 401/04* (2013.01); *C07D 401/14* (2013.01)

(58) Field of Classification Search
CPC .. C07D 401/04; C07D 401/14; C07D 405/14; A61P 35/00; A61P 31/18; A61P 31/00
See application file for complete search history.

(56) References Cited

U.S. PATENT DOCUMENTS
7,767,881 B2    8/2010  Kotani et al.
2005/0288347 A1 12/2005 Hodge et al.

FOREIGN PATENT DOCUMENTS

| WO | WO 2005/039569 A1 | 5/2005 | |
|---|---|---|---|
| WO | WO 2006/130160 A2 | 12/2006 | |
| WO | WO 2010/003908 A1 | 1/2010 | |
| WO | WO-2012174164 A2 * | 12/2012 | .......... C07D 471/04 |
| WO | WO 2017/070320 A1 | 4/2017 | |
| WO | WO 2017/197080 A1 | 11/2017 | |

OTHER PUBLICATIONS

Chemical Abstracts Service CAS Registry Nos. 1028266-83-2, 1027936-59-9 and 1026710-07-05, CAplus database entry dates of Jun. 15, 2008, Jun. 13, 2008 and Jun. 9, 2008; 1 p.*
International Preliminary Report on Patentability issued in International Patent Application No. PCT/US2018/032062, dated Nov. 12, 2019.
International Preliminary Report on Patentability issued in International Patent Application No. PCT/US2017/032099, dated Nov. 13, 2018.
Magnaghi, et al., "Covalent and Allosteric Inhibitors of the ATPase VCP/p97 Induce Cancer Cell Death," *Nature Chemical Biology*, 12 pages (Jul. 2013).
Paolo Polucci et al., "Alkylsulfanyl-1,2,4-triazoles, a New Class of Allosteric Valosine Containing Protein Inhibitors, Synthesis and Structure-Activity Relationships," *Journ. of Medicinal Chemistry*, vol. 56, No. 2, pp. 437-450 (Jan. 2013).
Banerjee et al., "2.3 Å resolution cryo-EM structure of human p97 and mechanism of allosteric inhibition," Science, (2016), 9 Pgs.
Pubchem, CHEMBL2315453, Jun. 11, 2013, pp. 1-7 [online], [retrieved on Jul. 12, 2017], Retrieved from the internet from https://pubchem.ncbi.nlm.nih.gov/compounds/71520307#section=2D-Structure; pp. 2-3, 6.
Pubchem, CHEMBL2315448, Jun. 11, 2013, pp. 1-7 [online], [retrieved on Jul. 12, 2017], Retrieved from the internet from https://pubchem.ncbi.nlm.nih.gov/compounds/71521795#section=BioAssay-Results; pp. 2-3.
Alverez, et al., Allosteric Indole Amide Inhibitors of p97: Identification of a Novel Probe of the Ubiquitin Pathway, ACS Medicinal Chemistry Letters, vol. 7, pp. 182-187, p. 183, figure 1 (2016).
Arpicco et al., "Anticancer prodrugs: An overview of major strategies and recent developments," *Curr. Top. Med. Chem.*, 7 7:2346-2381 (2011).
Banerjee, et al., "2.3 A resolution cryo-EM structure of human p97 and mechanism of allosteric Inhibitition," *Science*, vol. 331, No. 6275, pp. 871-875 (2016).
Blencowe et al., "Self-immolative linkers in polymeric delivery systems," *Polym. Chem.*, 2: 773-790 (2011); Arpicco et al., "Anticancer prodrugs: An overview of major strategies and recent developments," *Curr. Tot>. Med. Chem.* (*Shariah, United Arab Emirates*), 11:2346-2381 (2011).
Bodor, N., "Novel Approaches in Prodrug Design," *Drugs of the Future*, vol. 6, pp. 165-182 (1981).

(Continued)

*Primary Examiner* — John M Mauro
(74) *Attorney, Agent, or Firm* — Foley & Lardner LLP

(57) ABSTRACT

The present technology is directed to methods of inhibiting or modulating p97 and compounds and compositions useful in such methods Diseases and conditions that can be treated with the compounds and compositions of the present technology include, but are not limited to, antibacterial infection, antiviral infection, cancer and neurodegenerative disorders susceptible to treatment by inhibition or modulation of p97.

22 Claims, No Drawings

(56) References Cited

OTHER PUBLICATIONS

Bundgaard, H., "Design of Prodrugs: Bioreversible-Derivatives for Various Functional Groups and Chemical Entities," in Design of Prodrugs, Elsevier (1985), 1 page Abstract.

Deshaies et al., "Proteotoxic crisis, the ubiquitin-proteasome system, and cancer therapy," *BMC Biology*, 12(94), 14 pages (2014).

Huttunen et al., "Prodrugs—from serendipity to rational design," *Pharmacol. Rev.*, 63, 750-771 (2011).

Karaman, R., "Prodrugs design based on inter- and intramolecular chemical processes," *Chem. Biol. Drug Des.*, 82: 643-668 (2013).

Lee et al., "Pro-drug and Antedrug: Two Diametrical Approaches in Designing Safer Drugs," *Arch. Pharm. Res.*, 25:111-136 (2002).

Meyer et al., "Emerging functions of the VCP/p97 AAA-ATPase in the ubiquitin system," *Nature Cell Biology*, 14: 117-123 (2012).

Meyer et al., "*The VCP/p97 system at a glance: connecting cellular function to disease pathogenesis,*" *J. Cell Sci.*, 127, pp. 3877-3883 (2014).

Notari, "Theory and Practice of Prodrug Kinetics," *Methods in Enzymology*, vol. 112, pp. 309-323 (1985).

Rautio et al., "Prodrugs: Design and clinical applications," *Nat. Rev. Drug Discovery*, 7: 255-270 (2008).

Simplicio et al., "Prodrugs for amines," *Molecules*, 13: 519-547 (2008).

Tietze et al., "Antibody-directed enzyme prodrug therapy: A promising approach for a selective treatment of cancer based on prodrugs and monoclonal antibodies" *Chem. Biol. Drug Des.*, 74: 205-211 (2009).

Valle et al., "Critical Role of VCP/p97 in the Pathogenesis and Progression of Non-Small Cell Lung Carcinoma," *PlosOne*, 6(12): e29073, 12 pages (2011).

Zhang et al., "Structure of the AAA ATPase p97," *Molecular Cell*, 6(6): 1473-1484 (2000).

Zhang, et al., "Altered cofactor regulation with disease-associated p97NCP mutations," *Proc. Natl. Acad. Sci. USA*, 112(14), E1705-E1714 (2015).

Dantuma, et al., "Short-lived green fluorescent proteins for quantifying ubiquitin/proteasome-dependent proteolysis in living cells," Nature Biotechnology, vol. 18, pp. 538-543 (2000).

Notice of Allowance issued in co-pending U.S. Appl. No. 16/301,080, filed Aug. 18, 2020.

International Search Report issued in International Patent Application No. PCT/US2018/032062, filed May 10, 2018.

PubChem CID 70041846 Dated Created: Dec. 1, 2012, Date Accessed: Aug. 27, 2018, 11 pages.

Office Action issued in co-pending U.S. Appl. No. 16/301,080, dated Apr. 22, 2020.

\* cited by examiner

MODULATORS OF P97 AAA ATPASE ACTIVITY

CROSS-REFERENCE TO RELATED APPLICATIONS

This application is the U.S. National Stage of International Patent Application No. PCT/US2018/032062, filed May 10, 2018, which claims the benefit of U.S. Provisional Patent Application No. 62/504,732, filed May 11, 2017. These applications are incorporated herein by reference in their-entirety.

STATEMENT OF GOVERNMENT SUPPORT

This invention was made with government support under HHSN261200800001E awarded by the NIH. The government has certain rights in the invention.

BACKGROUND

The AAA ATPase p97 (also known as valosin-containing protein (VCP), Cdc48 in yeast and plants, CDC-48 in worms and Ter94 in flies), is a hexameric member of the AAA family (ATPases associated with diverse cellular activities). Zhang et al., "Structure of the AAA ATPase p97," Mol. Cell, 6(6): 1473-84 (2000).

Recent studies have uncovered cellular functions for p97 in autophagy, endosomal sorting and regulation of protein degradation at the outer mitochondrial membrane, and elucidated a role for p97 in key chromatin-associated processes. These findings extend the functional relevance of p97 to lysosomal degradation and reveal a dual role in protecting cells from protein stress and ensuring genome stability during proliferation. Meyer et al., "Emerging functions of the VCP/p97 AAA-ATPase in the ubiquitin system," Nature Cell Biol., 14: 117-123 (2012).

p97 also functions as an interaction hub, and different sets of at least 30 cofactors have been shown to be responsible for modulating p97-mediated processes. Meyer et al., "The VCP/p97 system at a glance: connecting cellular function to disease pathogenesis," J. Cell Sci., 127: 1-7 (2014).

A 2.3 Å resolution cryo-EM structure of human p97 and mechanism of allosteric inhibition was recently disclosed. Banerjee et al., Science, 351(6275): 871-875 (2016). Other structures have also been disclosed. See, e.g., Wipf et al., Organic & Biomolecular Chemistry, (2017), DOI:10.1039/C7OB00526A.

p97-associated disease: p97 is a potential therapeutic target for cancer and neurodegenerative diseases. Given the crucial role of p97 in maintaining cellular proteostasis, it is not surprising that autosomal dominant mutations in p97, the gene encoding p97, lead to a rare multisystem degenerative disorder previously termed IBMPFD/ALS. The acronym IBMPFD/ALS refers to the four main phenotypes that can affect patients carrying disease-associated mutations of p97 (i.e., inclusion body myopathy (IBM), Paget's disease of the bone (PDB), frontotemporal dementia (FTD) and amyotrophic lateral sclerosis (ALS)). However, a patient with a pathogenic p97 mutation can have any mixture of phenotypes, including all four phenotypes or just one phenotype in isolation. In addition, a member of the same family can have any combination of phenotypes. Id.

Some carriers of p97 mutation also manifest additional symptoms, including Parkinsonism, ataxia, cataracts, dilated cardiomyopathy, hepatic fibrosis, and hearing loss. The term 'multisystem proteinopathy' has been proposed as the nomenclature for an emerging family of genetic disorders that are unified by this characteristic variation in the penetrance of muscle, bone and CNS degenerative phenotypes along with the accumulation of ubiquitin and TDP-43-positive inclusions.

The protein p97 plays an important role in protein homeostasis. However, in numerous disease states, homeostasis is dysregulated, and inhibitors and/or modulators of p97 have the potential to address diseases such as cancer, and neurodegenerative disorders. The compounds described inhibit the ATPase activity of p97, have effects on p97-dependent mechanisms in cells and exhibit anti-proliferative activity. They have the potential to be anti-cancer agents, or drugs that are effective in neurodegenerative diseases, or any other disorder that relies on p97. Inhibitors of homologous proteins in bacteria and/or viruses could also be useful to treat infectious diseases. Inhibitors of AAA ATPases may also be useful to treat antibacterial and/or antiviral infection (see, e.g., (1) Cold Spring Harb Perspect Med 2015; 5:a021154; and (2) Franke, K. B.; Bukau, B.; Mogk, A. "Mutant Analysis Reveals Allosteric Regulation of Clpb Disaggregase." Front Mol Biosci 2017, 4, 6).

There remains a need in the art for inhibitors and/or modulators of p97 useful in treating cancer and neurodegenerative disorders caused by proteostatic malfunction. The present technology satisfies these needs. Further, there remains a need for compounds that are more efficacious with fewer side effects than other compounds that work through similar or unrelated p97 inhibition mechanisms.

SUMMARY OF THE DISCLOSED SUBJECT MATTER

The present technology is directed to methods of modulating p97 or inhibiting p97, and compounds and compositions useful in such methods. Diseases and conditions that can be treated with the compounds and compositions of the technology include, but are not limited to, antibacterial infection, antiviral infection, cancer, and neurodegenerative disorders susceptible to treatment by modulation or inhibition of p97. Exemplary neurodegenerative disorders include, but are not limited to, inclusion body myopathy (IBM), Paget's disease of the bone (PDB), frontotemporal dementia (FTD) and amyotrophic lateral sclerosis (ALS).

Subjects having p97 mutations may also be treated with the compounds and compositions according to the present technology. Such p97 mutations may manifest symptoms including but not limited to Parkinsonism, ataxia, cataracts, dilated cardiomyopathy, hepatic fibrosis, and hearing loss. Treatment with a compound or composition according to the present technology may ameliorate such symptoms.

In one aspect, provided is a compound having a structure of Formula (I):

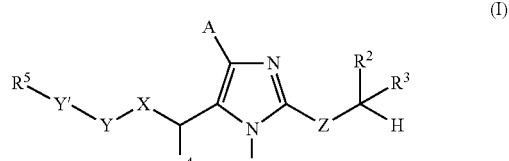

or a pharmaceutically acceptable salt, solvate, or prodrug thereof, wherein:

X is O, SO$_{0-2}$, NR, or C(R$^7$)$_2$;

Y is optionally substituted aryl, optionally substituted alkyl, optionally substituted alkenyl, alkynyl, optionally substituted heteroaryl, optionally substituted cycloalkyl, or optionally substituted non-aromatic heterocyclyl;

Y' is alkynyl, optionally substituted aryl, optionally substituted heteroaryl, optionally substituted cycloalkyl, optionally substituted non-aromatic heterocyclyl, or a bond;

R$^2$ and R$^3$ are independently H, optionally substituted C$_{1-6}$ alkyl, optionally substituted C$_{1-9}$ cyclic, optionally substituted C$_{3-9}$ heterocyclyl, or halogen, or R$^2$ and R$^3$ together form an optionally substituted C$_{3-9}$ cyclic or optionally substituted 3- to 9-membered heterocyclyl ring;

Z is O, SO$_{0-2}$, NR, C(R$^7$)$_2$, alkenyl or alkynyl;

R$^1$ is optionally substituted phenyl, optionally substituted 5- or 6-membered heteroaryl, or optionally substituted non-aromatic heterocyclic;

R$^4$ is H, C(R$^7$)$_2$, aryl, or heteroaryl;

R$^5$ is H, nitrile, an optionally substituted aryl, an optionally substituted heterocycle, optionally substituted C$_1$-C$_6$ alkyl, optionally substituted C$_3$-C$_9$ cycloalkyl, or

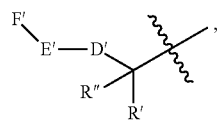

where
R' and R" are each independently selected from the group consisting of H, optionally substituted alkyl, —OR, halogen, —N(R)$_2$, optionally substituted cycloalkyl, and optionally substituted heterocyclyl;

or R' and R" may together form an optionally substituted 3- to 6-membered cycloalkyl or optionally substituted 3- to 6-membered non-aromatic heterocycle;

D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;

E' is selected from the group consisting of a bond, an optionally substituted C$_1$-C$_6$ alkyl, optionally substituted C$_1$-C$_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted C$_1$-C$_6$ alkyl, and optionally substituted cycloalkyl;

R$^7$ is independently selected from the group consisting of H, halogen, optionally substituted C$_1$-C$_6$ alkyl, optionally substituted cycloalkyl, —OR, and —N(R); and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

In another aspect, provided is a compound having a structure of Formula (Ia):

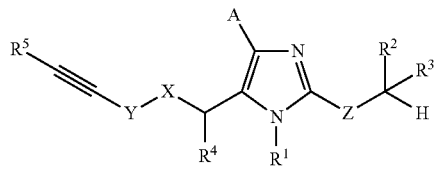

or a pharmaceutically acceptable salt, solvate, or prodrug thereof, wherein:

X is O, SO$_{0-2}$, NR, or C(R$^7$)$_2$,

Y is optionally substituted aryl, optionally substituted alkyl, optionally substituted alkenyl, alkynyl, optionally substituted heteroaryl, optionally substituted cycloalkyl, or optionally substituted non-aromatic heterocyclyl;

R$^2$ and R$^3$ are independently H, optionally substituted C$_{1-6}$ alkyl, optionally substituted C$_{1-9}$ cyclic, optionally substituted C$_{3-9}$ heterocyclyl, or halogen, or R$^2$ and R$^3$ together form an optionally substituted C$_{3-9}$ cyclic or optionally substituted 3- to 9-membered heterocyclyl ring;

Z is O, SO$_{0-2}$, NR, C(R$^7$)$_2$, alkenyl or alkynyl;

R$^1$ is optionally substituted phenyl, optionally substituted 5- or 6-membered heteroaryl, or optionally substituted non-aromatic heterocyclic;

R$^4$ is H, C(R$^7$)$_2$, aryl, or heteroaryl;

R$^5$ is H, nitrile, an optionally substituted aryl, an optionally substituted heterocycle, optionally substituted C$_1$-C$_6$ alkyl, optionally substituted C$_3$-C$_9$ cycloalkyl, or

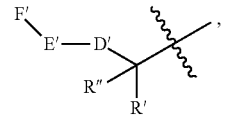

where
R' and R" are each independently selected from the group consisting of H, optionally substituted alkyl, —OR, halogen, —N(R)$_2$, optionally substituted cycloalkyl, and optionally substituted heterocyclyl;

or R' and R" may together form an optionally substituted 3- to 6-membered cycloalkyl or optionally substituted 3- to 6-membered non-aromatic heterocycle;

D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;

E' is selected from the group consisting of a bond, an optionally substituted C$_1$-C$_6$ alkyl, optionally substituted C$_1$-C$_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted C$_1$-C$_6$ alkyl, and optionally substituted cycloalkyl;

R$^7$ is independently selected from the group consisting of H, halogen, optionally substituted C$_1$-C$_6$ alkyl, optionally substituted cycloalkyl, —OR, and —N(R); and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)₂, or —COOR;

provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

In another aspect, provided is a compound having a structure of Formula (Ib):

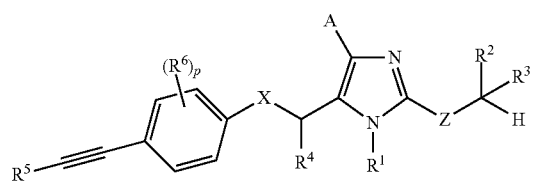

or a pharmaceutically acceptable salt, solvate, or prodrug thereof, wherein:

X is O, SO$_{0-2}$, or NR;

R² and R³ are independently H, optionally substituted C$_{1-6}$ alkyl, optionally substituted C$_{1-9}$ cyclic, optionally substituted C$_{3-9}$ heterocyclyl, or halogen, or R² and R³ together form an optionally substituted C$_{3-9}$ cyclic or optionally substituted 3- to 9-membered heterocyclyl ring;

Z is O, SO$_{0-2}$, NR, C(R⁷)₂, alkenyl or alkynyl;

R¹ is optionally substituted phenyl, optionally substituted 5- or 6-membered heteroaryl, or optionally substituted non-aromatic heterocyclic;

R⁴ is H, C(R⁷)₂, aryl, or heteroaryl;

R⁵ is H, nitrile, an optionally substituted aryl, an optionally substituted heterocycle, optionally substituted C$_1$-C$_6$ alkyl, optionally substituted C$_3$-C$_9$ cycloalkyl, or

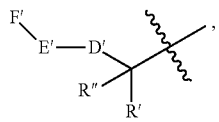

where
R' and R" are each independently selected from the group consisting of H, optionally substituted alkyl, —OR, halogen, —N(R)₂, optionally substituted cycloalkyl, and optionally substituted heterocyclyl;
or R' and R" may together form an optionally substituted 3- to 6-membered cycloalkyl or optionally substituted 3- to 6-membered non-aromatic heterocycle;
D' is selected from the group consisting of —O—, —NR—, —OCONR—, —OCO—, —NRSO₂—, —NRCO—, —NRSO₂NR—, —NRCOO—, —NR-CONR—, and —NRC(NR)NR—;
E' is selected from the group consisting of a bond, an optionally substituted C$_1$-C$_6$ alkyl, optionally substituted C$_1$-C$_6$ alkenyl, and optionally substituted cycloalkyl; and
F' is selected from the group consisting of H, an optionally substituted cycloalkyl, an optionally substituted non-aromatic heterocycle, an optionally substituted aryl, and an optionally substituted heteroaryl;
R is independently selected from the group consisting of H, optionally substituted C$_1$-C$_6$ alkyl, and optionally substituted cycloalkyl;

R⁶ is independently selected from the group consisting of alkyl, —CF₃, —OR, —CN, —CO₂R, halogen, —SR, —SOR, —SO₂R, —SF₅, and —NR₂;

p is 0, 1, or 2;

R⁷ is independently selected from the group consisting of H, halogen, optionally substituted C$_1$-C$_6$ alkyl, optionally substituted cycloalkyl, —OR, and —N(R); and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)₂, or —COOR;

provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

In another aspect, provided is a compound having a structure of Formula (Ic):

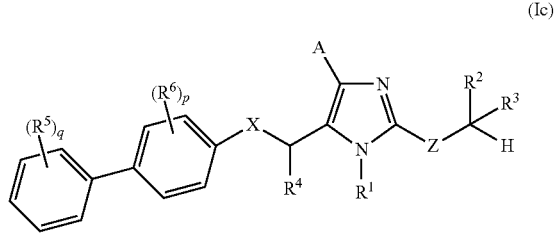

or a pharmaceutically acceptable salt, solvate, or prodrug thereof, wherein:

X is O, SO$_{0-2}$, or NR;

R² and R³ are independently H, optionally substituted C$_{1-6}$ alkyl, optionally substituted C$_{1-9}$ cyclic, optionally substituted C$_{3-9}$ heterocyclyl, or halogen, or R² and R³ together form an optionally substituted C$_{3-9}$ cyclic or optionally substituted 3- to 9-membered heterocyclyl ring;

Z is O, SO$_{0-2}$, NR, C(R⁷)₂, alkenyl or alkynyl;

R¹ is optionally substituted phenyl, optionally substituted 5- or 6-membered heteroaryl, or optionally substituted non-aromatic heterocyclic;

R⁴ is H, C(R⁷)₂, aryl, or heteroaryl;

R⁵ is independently selected from the group consisting of NO₂, optionally substituted alkynyl, optionally substituted alkenyl, C$_{1-6}$ alkyl, —CF₃, —OR, —CN, —CO₂R, halogen, —SR, —SOR, —SO₂R, —SF₅, and —NR₂;

R⁶ is independently selected from the group consisting of NO₂, optionally substituted alkynyl, optionally substituted alkenyl, alkyl, —CF₃, —OR, —CN, —CO₂R, halogen, —SR, —SOR, —SO₂R, —SF₅, and —NR₂;

p is 0, 1, or 2;

q is 0, 1, 2, 3, 4, or 5;

R is independently selected from the group consisting of H, optionally substituted C$_1$-C$_6$ alkyl, and optionally substituted cycloalkyl;

R⁷ is independently selected from the group consisting of H, halogen, optionally substituted C$_1$-C$_6$ alkyl, optionally substituted cycloalkyl, —OR, and —N(R)₂; and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)₂, or —COOR.

In some embodiments X is O or S. In some embodiments Y is selected from the group consisting of:

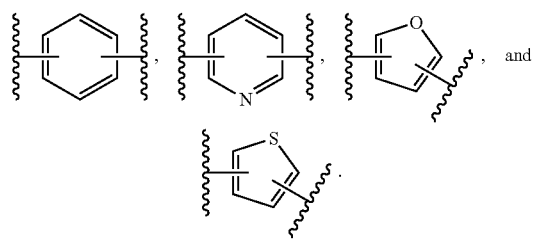

, and

In some embodiments, Y is phenylene optionally substituted with $C_1$-$C_6$ alkyl, cycloalkyl, —$CF_3$, —OR, —CN, —$CO_2R$, halogen, —SR, —SOR, —$SO_2R$, —$SF_5$, or —$NR_2$, or a combination of two or more thereof. In some embodiments, Y' is a bond, alkynyl, or optionally substituted aryl. In some embodiments, Y' is a bond, alkynyl, or phenylene optionally substituted with alkyl, —$CF_3$, —OR, —CN, —$CO_2R$, halogen, —SR, —SOR, —$SO_2R$, —$SF_5$, or —$NR_2$, or a combination of two or more thereof. In some embodiments, Z is selected from the group consisting of O, S and $CH_2$. In some embodiments, $R^5$ is a phenyl optionally substituted with one or more alkyl, —OR, —CN, —$CO_2R$, halogen, —SR, —SOR, —$SO_2R$, —$SF_5$, and —$NR_2$, or any combination thereof. In some embodiments, $R^5$ is a heterocycle optionally substituted with alkyl, —OR, —CN, —$CO_2R$, halogen, —SR, —SOR, —$SO_2R$, —$SF_5$ or —$NR_2$, or a combination of two or more thereof. In some embodiments, $R^5$ is

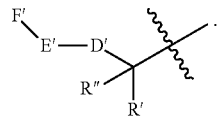

In some embodiments, R' and R" together form a 3- to 6-membered cycloalkyl or 3- to 6-membered non-aromatic heterocycle. In some embodiments, R' and R" are each H, or at least one of R' and R" is methyl and any remaining R' or R" is H. In some embodiments, at least one of R' and R" is an optionally substituted alkyl. In some embodiments, E' is a $C_1$-$C_6$ alkyl and F' is H. In some embodiments, F' is an optionally substituted cycloalkyl selected from: cyclopropyl, cyclobutyl, cyclopentyl, and cyclohexyl. In some embodiments, F' is an optionally substituted heterocycle selected from: morpholine, azetidine, alkyl-piperidine, alkyl-piperazine, alkyl-diazepane, thiomorpholine 1,1-dioxide, isoindoline-1,3-dione, tetrahydropyran, and pyrrolidone. In some embodiments, F' is an optionally substituted aryl selected from: phenyl, optionally substituted with alkyl, —$CF_3$, —OR, —CN, —$CO_2R$, halogen, —SR, —SOR, —$SO_2R$, —$SF_5$ or —$NR_2$, or a combination of two or more thereof. In some embodiments, F' is an optionally substituted heteroaryl selected from: alkyl-triazole, tetrazole, imidazole, and isoxazole. In some embodiments, D' is —O—, —NH—, —OCONH—, —OCO—, —NHCO—, or —NHCOO—. In some embodiments, $R^1$ is optionally substituted pyridine. In some embodiments, $R^2$ and $R^3$ together form a cyclopropyl, cyclopentyl or cyclohexene. In some embodiments, $R^2$ and $R^3$ are independently optionally substituted $C_{1-6}$ alkyl. In some embodiments, A is H, halogen, nitrile, optionally substituted alkyl, optionally substituted alkenyl, optionally substituted alkynyl, —$CON(R)_2$, or —COOR. In some embodiments, A is H.

In another aspect, provided is a compound having a structure of Formula (IIa):

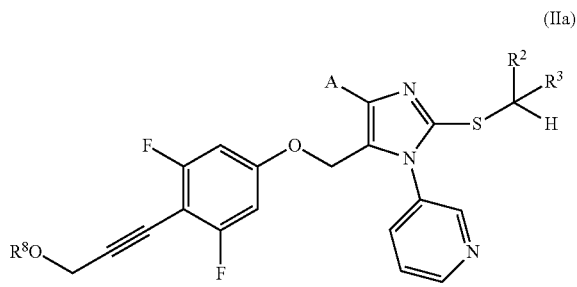

(IIa)

or a pharmaceutically acceptable salt, solvate, or prodrug thereof, wherein:

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —$CON(R)_2$, or —COOR;

R is independently selected from the group consisting of H, optionally substituted $C_1$-$C_6$ alkyl, and optionally substituted cycloalkyl; and $R^8$ is selected from the group consisting of H,

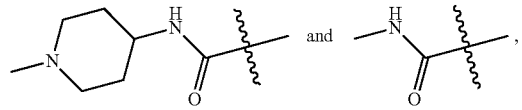

wherein ⁓ indicates a point of attachment to O.

In another aspect, provided is a compound having a structure of Formula (IIb):

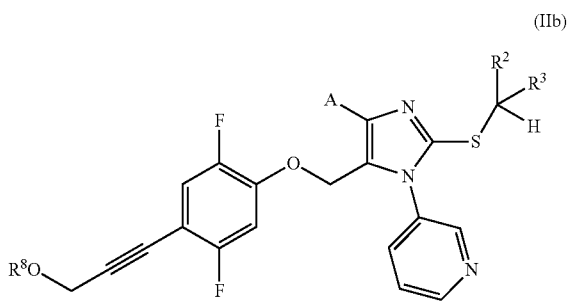

(IIb)

or a pharmaceutically acceptable salt, solvate, or prodrug thereof, wherein:

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

R is independently selected from the group consisting of H, optionally substituted $C_1$-$C_6$ alkyl, and optionally substituted cycloalkyl; and $R^8$ is selected from the group consisting of H,

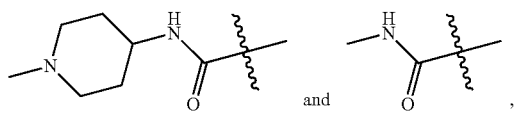

and wherein ⸵ indicates a point of attachment to O.

In another aspect, provided is a compound having a structure of Formula (III):

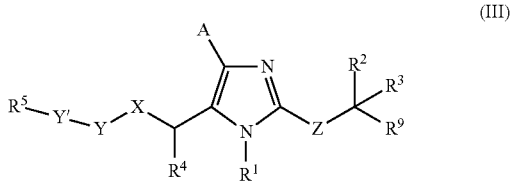

(III)

or a pharmaceutically acceptable salt, solvate, or prodrug thereof, wherein:

X is O, SO$_{0-2}$, NR, or C(R$^7$)$_2$;

Y is optionally substituted aryl, optionally substituted alkyl, optionally substituted alkenyl, alkynyl, optionally substituted heteroaryl, optionally substituted cycloalkyl, or optionally substituted non-aromatic heterocyclyl;

Y' is alkynyl, optionally substituted aryl, optionally substituted heteroaryl, optionally substituted cycloalkyl, optionally substituted non-aromatic heterocyclyl, or a bond;

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

Z is O, SO$_{0-2}$, NR, C(R$^7$)$_2$, alkenyl or alkynyl;

$R^1$ is optionally substituted phenyl, optionally substituted 5- or 6-membered heteroaryl, or optionally substituted non-aromatic heterocyclic;

$R^4$ is H, C(R$^7$)$_2$, aryl, or heteroaryl;

$R^5$ is H, nitrile, an optionally substituted aryl, an optionally substituted heterocycle, optionally substituted $C_1$-$C_6$ alkyl, optionally substituted $C_3$-$C_9$ cycloalkyl, or

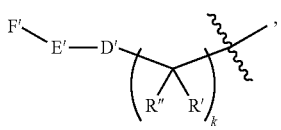

where k is 1, 2, 3, 4, or 5;

R' and R" are each independently selected from the group consisting of H, optionally substituted alkyl, —OR, halogen (e.g., F, Cl, Br, I), —N(R)$_2$, optionally substituted cycloalkyl, and optionally substituted heterocyclyl;

or R' and R" may together form an optionally substituted 3- to 6-membered cycloalkyl or optionally substituted 3- to 6-membered non-aromatic heterocycle;

D' is selected from the group consisting of —O—, —NR—, —OCONR—, —OCO—, —CO—, —CO(NR)—, —SO$_{0-2}$—, —SO$_{0-2}$NR—, —NRSO$_2$—, —NRCO—, —NRSO$_2$NR—, —NRCOO—, —NRCONR—, and —NRC(NR)NR—;

E' is selected from the group consisting of a bond, an optionally substituted $C_1$-$C_6$ alkyl, optionally substituted $C_1$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted $C_1$-$C_6$ alkyl, and optionally substituted cycloalkyl;

$R^7$ is independently selected from the group consisting of H, halogen, optionally substituted $C_1$-$C_6$ alkyl, optionally substituted cycloalkyl, —OR, and —N(R); and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

$R^9$ is H, nitrile, halogen, —C(O)(optionally substituted alkyl), optionally substituted heterocycle, optionally substituted cyclic ring, or optionally substituted alkyl;

provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

Some embodiments include a compound selected from those depicted in Tables I or III, or a pharmaceutically acceptable salt, solvate or prodrug thereof.

Some embodiments include a pharmaceutical composition comprising a compound of any of the embodiments herein and at least one pharmaceutically acceptable excipient.

In another aspect, provided is a method of inhibiting p97 in a subject in need thereof, comprising administering to the subject a therapeutically effective amount of a compound of any one of the embodiments herein or a therapeutically effective amount of a pharmaceutical composition of the embodiments herein.

In another aspect, provided is a method of modulating p97 in a subject in need thereof, comprising administering to the subject a therapeutically effective amount of a compound of any one of the embodiments herein or a therapeutically effective amount of a pharmaceutical composition of the embodiments herein.

In another aspect, provided is a method of treating cancer or a neurodegenerative disease susceptible to treatment by p97 inhibition in a subject in need thereof comprising administering to the subject a therapeutically effective amount of a compound of any of the embodiments herein or a therapeutically effective amount of a pharmaceutical composition of the embodiments herein. In some embodiments, the method is a method of treating cancer susceptible to treatment by p97 inhibition, wherein the cancer is selected from the group consisting of a solid tumor, non-small cell lung carcinoma, multiple myeloma, and mantle cell lymphoma. In some embodiments, the method is a method of treating a neurodegenerative disease susceptible to treatment by p97 inhibition, wherein the neurodegenerative disease is selected from the group consisting of inclusion body myopathy (IBM), Paget's disease of the bone (PDB), frontotemporal dementia (FTD) and amyotrophic lateral sclerosis (ALS).

In another aspect, provided is a method of treating cancer or a neurodegenerative disease susceptible to treatment by p97 modulation in a subject in need thereof comprising administering to the subject a therapeutically effective amount of a compound of any of the embodiments herein or a therapeutically effective amount of a pharmaceutical composition of the embodiments herein. In some embodiments, the method is a method of treating cancer susceptible to treatment by p97 modulation, wherein the cancer is selected from the group consisting of a solid tumor, non-small cell lung carcinoma, multiple myeloma, and mantle cell lymphoma. In some embodiments, the method is a method of treating a neurodegenerative disease susceptible to treatment by p97 modulation, wherein the neurodegenerative disease is selected from the group consisting of inclusion body myopathy (IBM), Paget's disease of the bone (PDB), frontotemporal dementia (FTD) and amyotrophic lateral sclerosis (ALS).

In another aspect, provided is a method of treating antibacterial and/or antiviral infection in a subject in need thereof comprising administering to the subject a therapeutically effective amount of a compound of any of the embodiments herein or a therapeutically effective amount of a pharmaceutical composition of the embodiments herein.

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction. Additional embodiments may be disclosed in the Detailed Description below.

DETAILED DESCRIPTION

I. Compounds of the Disclosure

The present disclosure provides imidazoles with p97 inhibitory activity or p97 modulatory activity.

In some embodiments, compounds of the present disclosure include those represented by Formula (I):

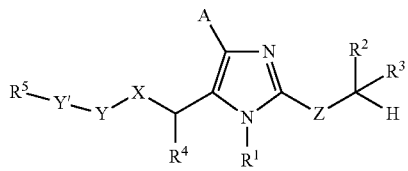

(I)

or a pharmaceutically acceptable salt, solvate, or prodrug thereof, wherein:

X is O, $SO_{0-2}$, NR, or $C(R^7)_2$;

Y is optionally substituted aryl, optionally substituted alkyl, optionally substituted alkenyl, alkynyl, optionally substituted heteroaryl, optionally substituted cycloalkyl, or optionally substituted non-aromatic heterocyclyl;

Y' is alkynyl, optionally substituted aryl, optionally substituted heteroaryl, optionally substituted cycloalkyl, optionally substituted non-aromatic heterocyclyl, or a bond;

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

Z is O, $SO_{0-2}$, NR, $C(R^7)_2$, alkenyl or alkynyl;

$R^1$ is optionally substituted phenyl, optionally substituted 5- or 6-membered heteroaryl, or optionally substituted non-aromatic heterocyclic;

$R^4$ is H, $C(R^7)_2$, aryl, or heteroaryl;

$R^5$ is H, nitrile, an optionally substituted aryl, an optionally substituted heterocycle, optionally substituted $C_1$-$C_6$ alkyl, optionally substituted $C_3$-$C_9$ cycloalkyl, or

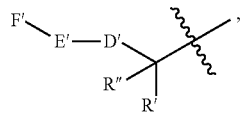

where

R' and R" are each independently selected from the group consisting of H, optionally substituted alkyl, —OR, halogen (e.g., F, Cl, Br, I), —N(R)$_2$, optionally substituted cycloalkyl, and optionally substituted heterocyclyl;

or R' and R" may together form an optionally substituted 3- to 6-membered cycloalkyl or optionally substituted 3- to 6-membered non-aromatic heterocycle;

D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;

E' is selected from the group consisting of a bond, an optionally substituted $C_1$-$C_6$ alkyl, optionally substituted $C_1$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted $C_1$-$C_6$ alkyl, and optionally substituted cycloalkyl;

$R^7$ is independently selected from the group consisting of H, halogen, optionally substituted $C_1$-$C_6$ alkyl, optionally substituted cycloalkyl, —OR, and —N(R); and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

In some embodiments, compounds of the present disclosure include those represented by Formula (Ia):

(Ia)

or a pharmaceutically acceptable salt, solvate, or prodrug thereof, wherein:
X is O, $SO_{0-2}$, NR, or $C(R^7)_2$;
Y is optionally substituted aryl, optionally substituted alkyl, optionally substituted alkenyl, alkynyl, optionally substituted heteroaryl, optionally substituted cycloalkyl, or optionally substituted non-aromatic heterocyclyl;
$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;
Z is O, $SO_{0-2}$, NR, $C(R^7)_2$, alkenyl or alkynyl;
$R^1$ is optionally substituted phenyl, optionally substituted 5- or 6-membered heteroaryl, or optionally substituted non-aromatic heterocyclic;
$R^4$ is H, $C(R^7)_2$, aryl, or heteroaryl;
$R^5$ is H, nitrile, an optionally substituted aryl, an optionally substituted heterocycle, optionally substituted $C_1$-$C_6$ alkyl, optionally substituted $C_3$-$C_9$ cycloalkyl, or where
R' and R" are each independently selected from the group consisting of H, optionally substituted alkyl, —OR, halogen (e.g., F, Cl, Br, I), —N(R)$_2$, optionally substituted cycloalkyl, and optionally substituted heterocyclyl;
or R' and R" may together form an optionally substituted 3- to 6-membered cycloalkyl or optionally substituted 3- to 6-membered heterocycle;
D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;
E' is selected from the group consisting of a bond, an optionally substituted $C_1$-$C_6$ alkyl, optionally substituted $C_1$-$C_6$ alkenyl, and optionally substituted cycloalkyl; and
F' is selected from the group consisting of H, an optionally substituted cycloalkyl, an optionally substituted non-aromatic heterocycle, an optionally substituted aryl, and an optionally substituted heteroaryl;
R is independently selected from the group consisting of H, optionally substituted $C_1$-$C_6$ alkyl, and optionally substituted cycloalkyl;
$R^7$ is independently selected from the group consisting of H, halogen, optionally substituted $C_1$-$C_6$ alkyl, optionally substituted cycloalkyl, —OR, and —N(R); and
A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;
provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

In some embodiments, compounds of the present disclosure include those represented by Formula (Ib):

(Ib)

or a pharmaceutically acceptable salt, solvate, or prodrug thereof, wherein:
X is O, $SO_{0-2}$, or NR;
$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;
Z is O, $SO_{0-2}$, NR, $C(R^7)_2$, alkenyl or alkynyl;
$R^1$ is optionally substituted phenyl, optionally substituted 5- or 6-membered heteroaryl, or optionally substituted non-aromatic heterocyclic;
$R^4$ is H, $C(R^7)_2$, aryl, or heteroaryl;
$R^5$ is H, nitrile, an optionally substituted aryl, an optionally substituted heterocycle, optionally substituted $C_1$-$C_6$ alkyl, optionally substituted $C_3$-$C_9$ cycloalkyl, or where
R' and R" are each independently selected from the group consisting of H, optionally substituted alkyl, —OR, halogen (e.g., F, Cl, Br, I), —N(R)$_2$, optionally substituted cycloalkyl, and optionally substituted heterocyclyl;
or R' and R" may together form an optionally substituted 3- to 6-membered cycloalkyl or optionally substituted 3- to 6-membered non-aromatic heterocycle;
D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;
E' is selected from the group consisting of a bond, an optionally substituted $C_1$-$C_6$ alkyl, optionally substituted $C_1$-$C_6$ alkenyl, and optionally substituted cycloalkyl; and
F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted $C_1$-$C_6$ alkyl, and optionally substituted cycloalkyl;

$R^6$ is independently selected from the group consisting of alkyl, —$CF_3$, —OR, —CN, —$CO_2R$, halogen, —SR, —SOR, —$SO_2R$, —$SF_5$, and —$NR_2$;

p is 0, 1, or 2;

$R^7$ is independently selected from the group consisting of H, halogen, optionally substituted $C_1$-$C_6$ alkyl, optionally substituted cycloalkyl, —OR, and —N(R); and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

In some embodiments, compounds of the present disclosure include those represented by Formula (Ic):

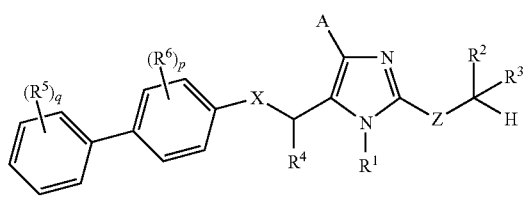

(Ic)

or a pharmaceutically acceptable salt, solvate, or prodrug thereof, wherein:

X is O, $SO_{0-2}$, or NR;

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

Z is O, $SO_{0-2}$, NR, $C(R^7)_2$, alkenyl or alkynyl;

$R^1$ is optionally substituted phenyl, optionally substituted 5- or 6-membered heteroaryl, or optionally substituted non-aromatic heterocyclic;

$R^4$ is H, $C(R^7)_2$, aryl, or heteroaryl;

$R^5$ is independently selected from the group consisting of $NO_2$, optionally substituted alkynyl, optionally substituted alkenyl, $C_{1-6}$ alkyl, —$CF_3$, —OR, —CN, —$CO_2R$, halogen, —SR, —SOR, —$SO_2R$, —$SF_5$, or —$NR_2$;

$R^6$ is independently selected from the group consisting of $NO_2$, optionally substituted alkynyl, optionally substituted alkenyl, alkyl, —$CF_3$, —OR, —CN, —$CO_2R$, halogen, —SR, —SOR, —$SO_2R$, —$SF_5$, and —$NR_2$;

p is 0, 1, or 2;

q is 0, 1, 2, 3, 4, or 5;

R is independently selected from the group consisting of H, optionally substituted $C_1$-$C_6$ alkyl, and optionally substituted cycloalkyl;

$R^7$ is independently selected from the group consisting of H, halogen, optionally substituted $C_1$-$C_6$ alkyl, optionally substituted cycloalkyl, —OR, and —N(R)$_2$; and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR.

In some embodiments of a compound of Formulae (I), (Ia), (Ib), or (Ic), X is O, S, SO, or $SO_2$. In some embodiments, X is O. In some embodiments, X is S. In some embodiments, X is NR. In some embodiments, X is NH. In some embodiments, X is SO. In some embodiments, X is $SO_2$.

In some embodiments of a compound of Formula (I), Y and Y' are not both phenylene.

In some embodiments of a compound of Formula (I), Y' is selected from the group consisting of an alkyne, an optionally substituted heteroaryl, an optionally substituted $C_3$-$C_{10}$ cycloalkyl, and an optionally substituted non-aromatic heterocycle (containing one or more O, S, SO, $SO_2$, N, or NR). In some embodiments, Y' is selected from:

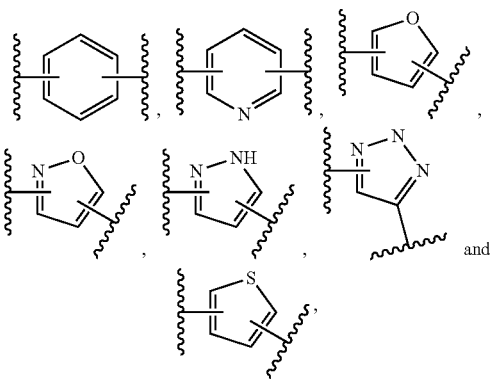

and and each of which may be optionally substituted. In some embodiments, Y' is cyclobutane, cyclobutene, propellane (such as, but not limited to, [1.1.1.0$^{1,3}$] propellane), cubane, or

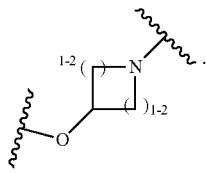

In some embodiments of a compound of Formulae (I) or (Ia), Y is selected from the group consisting of an optionally substituted alkyl, an optionally substituted alkenyl, an optionally substituted aryl, an optionally substituted heteroaryl, an optionally substituted $C_3$-$C_{10}$ cycloalkyl, and an optionally substituted non-aromatic heterocycle (containing one or more O, S, SO, $SO_2$, B, N, or NR). In some embodiments, Y is selected from:

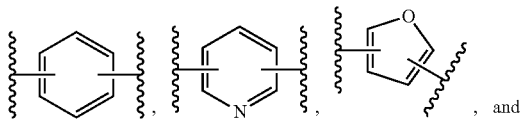

, and

-continued

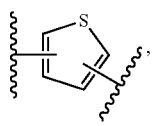

each of which may be optionally substituted. In some embodiments, Y is

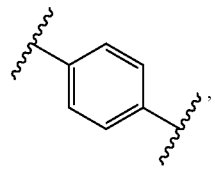 [SMILES: *c1ccc(*)cc1]

which may be optionally substituted; for example, the phenylene may be substituted with $C_1$-$C_6$ alkyl, cycloalkyl, halogen, —$NR_2$, —$SF_5$ or —OR, or a combination of two or more thereof. In some embodiments, Y is phenylene optionally substituted with $C_1$-$C_6$ alkyl, cycloalkyl, —$CF_3$, —OR, —CN, —$CO_2R$, halogen, —SR, —SOR, —$SO_2R$, —$SF_5$, or —$NR_2$, or a combination of two or more thereof. In some embodiments, the phenylene is substituted by methyl or perfluoromethyl. In some embodiments, the substitution is at a position ortho to the alkyne. Other examples within these embodiments, include phenylene moieties substituted by one or more fluoro moiety. For example, the phenylene moieties may be

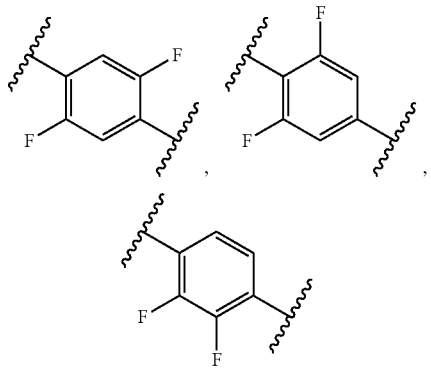

or further substituted variants thereof, e.g.,

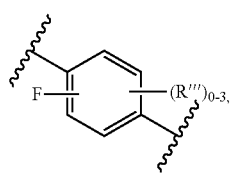

where R''' is a halogen (e.g., F, Cl, I, or Br), nitrile, a $C_1$-$C_6$ alkyl, or O—$C_1$-$C_6$ alkyl. In some embodiments, the phenylene is di-substituted, for example,

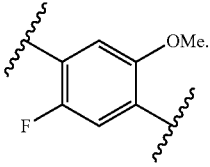 [SMILES: *c1cc(OC)c(*)cc1F]

In some embodiments, Y is phenylene optionally substituted with $C_1$-$C_6$ alkyl, $C_1$-$C_6$ haloalkyl, halogen, $C_1$-$C_6$ alkoxy, nitrile, or a combination of two or more thereof. In some embodiments, Y is cyclobutane, cyclobutene, propellane (such as, but not limited to, [1.1.1.0$^{1,3}$] propellane), cubane, or

In some embodiments of a compound of Formulae (I), (Ia), (Ib), or (Ic), Z is selected from the group consisting of O, S, and $C(R^7)_2$, where $R^7$ is independently H, halogen, optionally substituted alkyl, optionally substituted cycloalkyl, or —$N(R)_2$. In some embodiments, R or $R^7$ is H. In some embodiments, $R^7$ is H. In some embodiments, Z is $CH_2$. In some embodiments, Z is O. In some embodiments, Z is S. In some embodiments, Z is selected from the group consisting of O, S and $CH_2$.

In some embodiments of a compound of Formulae (I), (Ia), or (Ib), $R^5$ is an optionally substituted aryl. In some embodiments, $R^5$ is an unsubstituted or substituted phenyl. In some embodiments, the phenyl is substituted with one or more of alkyl, —OR, —CN, —$CO_2R$, halogen, —SR, —SOR, —$SO_2R$, —$SF_5$, or —$NR_2$, or any combination thereof.

In some embodiments of a compound of Formulae (I), (Ia), or (Ib), $R^5$ is heterocyclyl (e.g., a morpholine or pyridine), optionally substituted with one or more alkyl, —OR, —CN, —$CO_2R$, halogen, —SR, —SOR, —$SO_2R$, —$SF_5$, or —$NR_2$, or any combination thereof.

In some embodiments of a compound of Formulae (I), (Ia), or (Ib), $R^5$ is $C_1$-$C_6$ alkyl optional substituted with alkoxy, hydroxy, amino, non-aromatic heterocyclyl, cycloalkyl, aryl, heteroaryl. In some embodiments, $R^5$ is H.

In some embodiments of a compound of Formulae (I), (Ia), or (Ib), $R^5$ is

where
D' is selected from the group consisting of —O—, —NR—, —OCONR—, —OCO—, —$NRSO_2$—, —NRCO—, —$NRSO_2NR$—, —NRCOO—, —NRCONR—, and —NRC(NR)NR—; E' is selected from the group consisting of a bond, an optionally substituted $C_1$-$C_6$ alkyl, optionally substituted $C_1$-$C_6$ alkenyl, and optionally substituted cycloalkyl; and F' is selected from the group consisting of H, halogen, an optionally substituted cycloalkyl, an optionally substituted non-aromatic heterocycle, an optionally substituted aryl, and an optionally substituted heteroaryl.

In some embodiments, D' is selected from the group consisting of O, NH, OCONH, OCO, NHSO$_2$, NHCO, NHSO$_2$NH, NHCOO, and NHCONH. In some embodiments, D' is —O—, —NH—, —OCONH—, —OCO—, —NHCO—, or —NHCOO—. In some embodiments, D' is —O—. In some embodiments, D' is —NH—. In some embodiments, D' is —OCONH—. In some embodiments, D' is —OCO—. In some embodiments, D' is —NHCO—. In some embodiments, D' is —NHCOO—.

In some embodiments, E' is a bond, an optionally substituted $C_1$-$C_6$ alkyl, or optionally substituted cycloalkyl. In some embodiments, E' is an optionally substituted $C_1$-$C_6$ alkyl. In some embodiments, E' is an optionally substituted $C_1$-$C_6$ alkyl and F' is H. In some embodiments, E' is an optionally substituted $C_3$-$C_6$ cycloalkyl, (e.g., optionally substituted with alkyl, halogen, or —OR). In some embodiments, the cycloalkyl is specifically selected from, e.g., one of the following: cyclopropyl, cyclobutyl, cyclopentyl, and cyclohexyl, each of which may be optionally substituted. In some embodiments, E' is $C_1$-$C_6$ alkyl and F' is H.

In some embodiments, F' is an optionally substituted cycloalkyl, an optionally substituted non-aromatic heterocycle, an optionally substituted aryl, or an optionally substituted heteroaryl, each of which is described below in further detail. In some embodiments, F' is substituted with one or more alkyl, perfluoroalkyl (e.g., CF$_3$), —OR, —CN, —CO$_2$R, halogen, —SR, —SOR, —SO$_2$R, —SF$_5$, or —NR$_2$, or any combination thereof. In some embodiments, F' is not substituted.

In some embodiments, F' is an optionally substituted cycloalkyl. For example, F' may be a $C_3$-$C_6$ cycloalkyl, optionally substituted with alkyl, halogen, or —OR. In some embodiments, the cycloalkyl is specifically selected from, e.g., one of the following: cyclopropyl, cyclobutyl, cyclopentyl, and cyclohexyl, each of which may be optionally substituted. In some embodiments, the cycloalkyl is specifically selected from, e.g., one of the following: cyclopropyl, cyclobutyl, cyclopentyl, cyclohexyl, and propellane, each of which may be optionally substituted. In some embodiments, E' is a bond and F' is an optionally substituted cycloalkyl. In some embodiments, E' is optionally substituted $C_1$-$C_6$ alkyl and F' is an optionally substituted cycloalkyl.

In some embodiments, F' is an optionally substituted heterocycle. For example, F' may be a 4-6 membered non-aromatic heterocycle, optionally substituted with alkyl, halogen, or OR. In some embodiments, the heterocycle contains one or more heteroatom selected from: 0, S, SO, SO$_2$, B, N, and NR. Particular embodiments include, e.g., morpholine, azetidine, alkyl-piperidine, alkyl-piperazine, alkyl-diazepane, thiomorpholine 1,1-dioxide, isoindoline-1,3-dione, tetrahydropyran, and pyrrolidone. In some embodiments, E' is a bond and F' is an optionally substituted non-aromatic heterocycle. In some embodiments, E' is optionally substituted $C_1$-$C_6$ alkyl and F' is an optionally substituted non-aromatic heterocycle.

In some embodiments, F' is an optionally substituted aryl. For example, F' may be a $C_6$-$C_{10}$ aryl, e.g., a phenyl, that is optionally substituted, e.g., with one or more of alkyl, perfluoroalkyl (e.g., CF$_3$), —OR, —CN, —CO$_2$R, halogen, —SR, —SOR, —SO$_2$R, —SF$_5$, or —NR$_2$, or any combination thereof. In some embodiments, E' is a bond and F' is an optionally substituted aryl. In some embodiments, E' is optionally substituted $C_1$-$C_6$ alkyl and F' is an optionally substituted aryl.

In some embodiments, F' is an optionally substituted heteroaryl. For example, F' may be a 5-6 membered heteroaryl, optionally substituted with alkyl, halogen, or OR. In some embodiments, the heteroaryl contains one or more heteroatom selected from O, S, SO, N, and NR. Particular embodiments include, e.g., alkyl-triazole, tetrazole, imidazole, and isoxazole. In some embodiments, E' is a bond and F' is an optionally substituted heteroaryl. In some embodiments, E' is optionally substituted $C_1$-$C_6$ alkyl and F' is an optionally substituted heteroaryl.

In some embodiments of a compound of Formulae (I), (Ia), or (Ib), $R^5$ is:

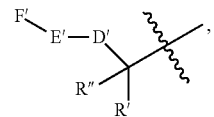

where
R' and R" are each independently selected from the group consisting of H, optionally substituted alkyl, —OR, halogen (e.g., F, Cl, Br, I), —N(R)$_2$, optionally substituted cycloalkyl, and optionally substituted non-aromatic heterocyclyl. In some embodiments, R' and R" are each H, or at least one of R' and R" is methyl and any remaining R' or R" is H. In some embodiments, R' and R" are each H. In some embodiments, at least one of R' and R" is optionally substituted alkyl and any remaining R' or R" is H. In some embodiments, the optionally substituted alkyl is a $C_1$-$C_6$ alkyl or $C_1$-$C_6$ perfluoroalkyl. In some embodiments, the optionally substituted alkyl is methyl. In some embodiments, R' and R" are each independently optionally substituted $C_1$-$C_6$ alkyl.

Alternatively, R' and R" together may form a 3- to 6-membered cycloalkyl or 3- to 6-membered non-aromatic heterocycle that is optionally substituted. In some embodiments, the 3- to 6-membered cycloalkyl or 3- to 6-membered non-aromatic heterocycle is substituted by one or more R$^7$, as defined previously. In additional embodiments, R' and R" form a cyclopropyl, cyclobutyl, cyclopentyl, or cyclohexyl. In other embodiments, R' and R" form an oxetane. In some embodiments, R' and R" form an optionally substituted azetidine, oxetane, pyrrolidone or piperidine. In some embodiments, the nitrogen of the azetidine, pyrrolidone or piperidine may be substituted with R, SO$_2$R, COR, SO$_2$NR$_2$, CONR$_2$ and COOR. In some embodiments, when R' and R" form a ring, e.g., an optionally substituted cyclopropyl, cyclobutyl, cyclopentyl, or cyclohexyl, azetidine, oxetane, pyrrolidone or piperidine, then D'-E'-F' together form an —OH (i.e., D' is —O—, E' is a bond and F' is H).

In some embodiments of a compound of Formulae (I), (Ia), (Ib), or (Ic), $R^1$ is an optionally substituted phenyl or an optionally substituted 5- or 6-membered heteroaryl. For example, in some embodiments, $R^1$ is optionally substituted phenyl or optionally substituted pyridine. In some embodiments, $R^1$ is an unsubstituted phenyl or an unsubstituted pyridine. In some embodiments, $R^1$ is a pyridine. In some embodiments the pyridine is attached at the 2 position, the 3 position or the 4 position. In some embodiments the pyridine is attached at the 3 position. In some embodiments, $R^1$ is optionally substituted non-aromatic heterocyclic.

In some embodiments of a compound of Formulae (I), (Ia), (Ib), or (Ic), $R^2$ and $R^3$ are independently optionally substituted $C_{1-6}$ alkyl. In some embodiments, $R^2$ and $R^3$ are both methyl. In some embodiments, at least one of $R^2$ and $R^3$ is methyl.

In some embodiments of a compound of Formulae (I), (Ia), (Ib), or (Ic), $R^2$ and $R^3$ are independently an optionally substituted $C_{3-9}$ cyclic, optionally substituted $C_{3-9}$ heterocyclic, or halogen, or $R^2$ and $R^3$ together form an optionally substituted $C_{3-9}$ cyclic or optionally substituted 3- to 9-membered heterocyclic ring. In some embodiments, $R^2$ is a $C_1$-$C_6$ alkyl, a $C_3$-$C_{10}$ cycloalkyl (including cycloalkenyl), or a heterocycle, each of which maybe optionally substituted.

In some embodiments of a compound of Formulae (I), (Ia), (Ib), or (Ic), $R^2$ and $R^3$ together form an optionally substituted $C_{3-9}$ cyclic or optionally substituted 3- to 9-membered heterocyclic ring, for example, a $C_3$-$C_{10}$ cycloalkyl (including cycloalkenyl), or a heterocycle, each of which maybe optionally substituted. Exemplary individual embodiments when $R^2$ and $R^3$ together form an optionally substituted $C_{3-9}$ cyclic or optionally substituted 3- to 9-membered heterocyclic ring, include cyclopropyl, cyclobutyl, cyclopentyl, cyclohexyl, cyclopentene, and cyclohexene, each of which may be optionally substituted, for example, by one or more deuterium or fluorine moiety. Other embodiments include bicyclic structures, such as:

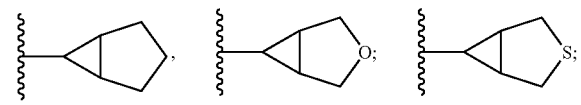

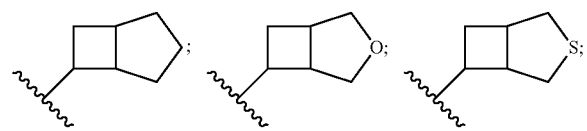

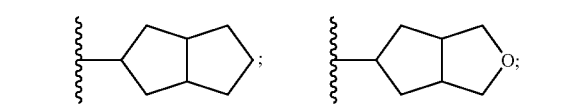

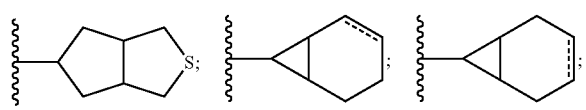

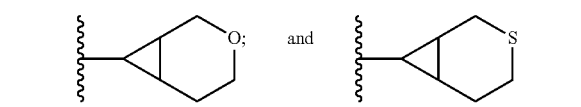

where one or more of the dashed bonds may optionally be a double bond and ⸹ indicates attachment to Z. In some embodiments, $R^2$ and $R^3$ together form a cyclopropyl, cyclopentyl or cyclohexene. In some embodiments, $R^2$ and $R^3$ together form a cyclopropyl. In some embodiments, $R^2$ and $R^3$ together form a cyclopentyl. In some embodiments, $R^2$ and $R^3$ together form a cyclohexene.

In some embodiments of a compound of Formulae (I), (Ia), (Ib), or (Ic), one or more hydrogens in $R^2$ or $R^3$, or in both $R^2$ and $R^3$ are replaced with deuterium. In some embodiments, $R^2$ and $R^3$ form a perdeuterated cycloalkyl ring. In some embodiments, $R^2$ and $R^3$ form a perdeuterated cyclopentane

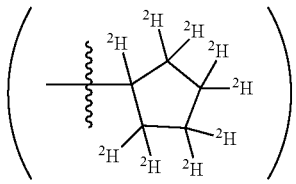

and ⸹ indicates attachment to Z. In some embodiments,

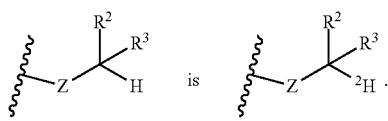

In some embodiments of a compound of Formulae (I), (Ia), (Ib), or (Ic), A is H, halogen, nitrile, optionally substituted alkyl, optionally substituted alkenyl, optionally substituted alkynyl, —CON(R)$_2$, or —COOR. In some embodiments, A is H. In some embodiments, A is halogen. In some embodiments, A is nitrile. In some embodiments, A is optionally substituted alkyl. In some embodiments, A is optionally substituted alkenyl. In some embodiments, A is optionally substituted alkynyl. In some embodiments, A is —COR, —CON(R)$_2$, or —COOR.

In some embodiments, compounds of the present disclosure include those represented by Formula (IIa):

(IIa)

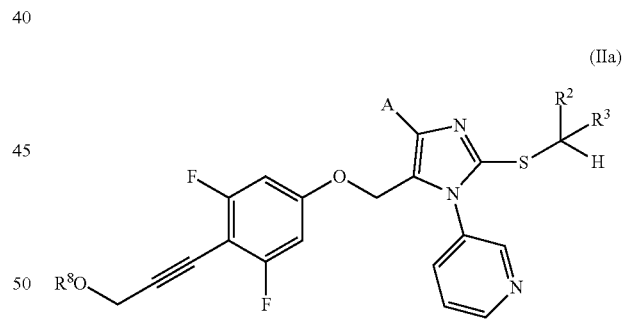

or a pharmaceutically acceptable salt, solvate, or prodrug thereof, wherein:

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

R is independently selected from the group consisting of H, optionally substituted $C_1$-$C_6$ alkyl, and optionally substituted cycloalkyl; and $R^8$ is selected from the group consisting of H,

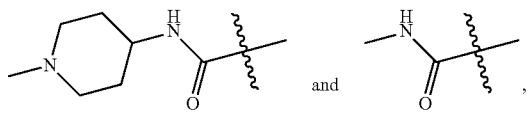

wherein $\xi$ indicates a point of attachment to O.

In some embodiments, compounds of the present disclosure include those represented by Formula (IIb):

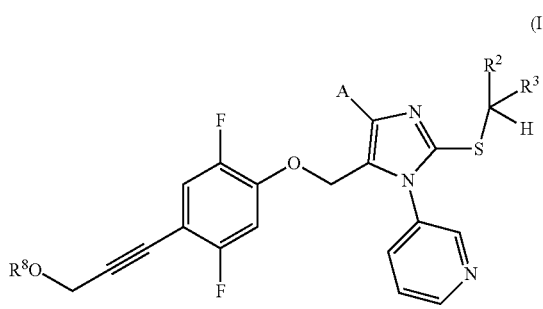

(IIb)

or a pharmaceutically acceptable salt, solvate, or prodrug thereof, wherein:

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

R is independently selected from the group consisting of H, optionally substituted $C_1$-$C_6$ alkyl, and optionally substituted cycloalkyl; and $R^8$ is selected from the group consisting of H,

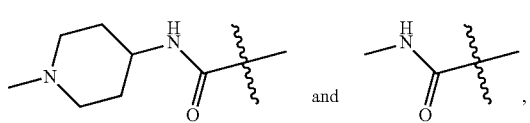

wherein $\xi$ indicates a point of attachment to O.

In some embodiments of a compound of Formulae (IIa) or (IIb), $R^2$ and $R^3$ are independently optionally substituted $C_{1-6}$ alkyl. In some embodiments, $R^2$ and $R^3$ are both methyl. In some embodiments, at least one of $R^2$ and $R^3$ is methyl.

In some embodiments of a compound of Formulae (IIa) or (IIb), $R^2$ and $R^3$ are independently an optionally substituted $C_{1-9}$ cyclic, optionally substituted $C_{3-9}$ heterocyclic, or halogen, or $R^2$ and $R^3$ together form an optionally substituted $C_{3-9}$ cyclic or optionally substituted 3- to 9-membered heterocyclic ring. In some embodiments, $R^2$ is a $C_1$-$C_6$ alkyl, a $C_3$-$C_{10}$ cycloalkyl (including cycloalkenyl), or a heterocycle, each of which maybe optionally substituted.

In some embodiments of a compound of Formulae (IIa) or (IIb), $R^2$ and $R^3$ together form an optionally substituted $C_{3-9}$ cyclic or optionally substituted 3- to 9-membered heterocyclic ring, for example, a $C_3$-$C_{10}$ cycloalkyl (including cycloalkenyl), or a heterocycle, each of which maybe optionally substituted. Exemplary individual embodiments when $R^2$ and $R^3$ together form an optionally substituted $C_{3-9}$ cyclic or optionally substituted 3- to 9-membered heterocyclic ring, include cyclopropyl, cyclobutyl, cyclopentyl, cyclohexyl, cyclopentene, and cyclohexene, each of which may be optionally substituted, for example, by one or more deuterium or fluorine moiety. Other embodiments include bicyclic structures, such as:

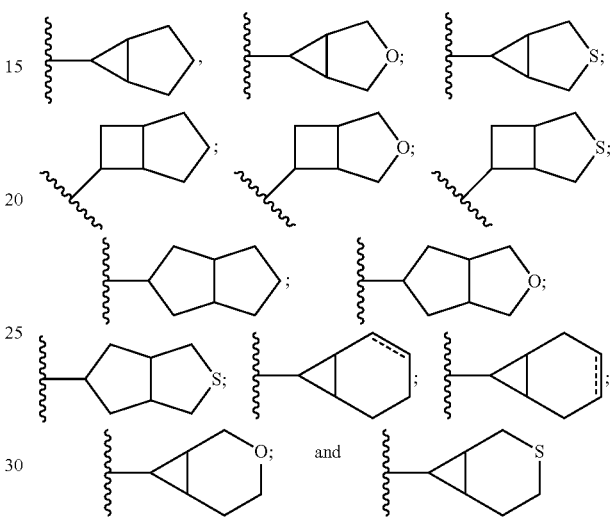

where one or more of the dashed bonds may optionally be a double bond and $\xi$ indicates attachment to S. In some embodiments, $R^2$ and $R^3$ together form a cyclopropyl, cyclopentyl or cyclohexene. In some embodiments, $R^2$ and $R^3$ together form a cyclopropyl. In some embodiments, $R^2$ and $R^3$ together form a cyclopentyl. In some embodiments, $R^2$ and $R^3$ together form a cyclohexene.

In some embodiments of a compound of Formulae (IIa) or (IIb), one or more hydrogens in $R^2$ or $R^3$, or in both $R^2$ and $R^3$ are replaced with deuterium. In some embodiments, $R^2$ and $R^3$ form a perdeuterated cycloalkyl ring. In some embodiments, $R^2$ and $R^3$ form a perdeuterated cyclopentane

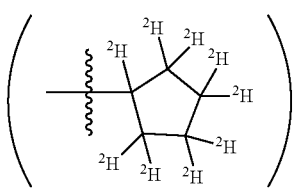

and $\xi$ indicates attachment to S. In some embodiments,

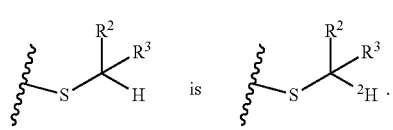

In some embodiments of a compound of Formulae (IIa) or (IIb), A is H, halogen, nitrile, optionally substituted alkyl, optionally substituted alkenyl, optionally substituted alkynyl, CON(R)$_2$, or —COOR. In some embodiments, A is H. In some embodiments, A is halogen. In some embodiments, A is nitrile. In some embodiments, A is optionally substituted alkyl. In some embodiments, A is optionally substituted alkenyl. In some embodiments, A is optionally substituted alkynyl. In some embodiments, A is —COR, —CON(R)$_2$, or —COOR. In some embodiments, R is independently selected from the group consisting of H, optionally substituted C$_1$-C$_6$ alkyl, and optionally substituted cycloalkyl.

In some embodiments, compounds of the present disclosure include those represented by Formula (III):

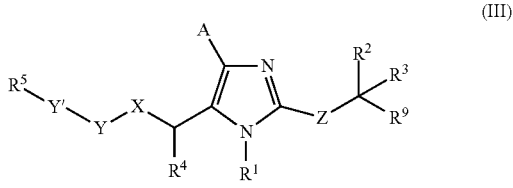

(III)

or a pharmaceutically acceptable salt, solvate, or prodrug thereof, wherein:

X is O, SO$_{0-2}$, NR, or C(R$^7$)$_2$;

Y is optionally substituted aryl, optionally substituted alkyl, optionally substituted alkenyl, alkynyl, optionally substituted heteroaryl, optionally substituted cycloalkyl, or optionally substituted non-aromatic heterocyclyl;

Y' is alkynyl, optionally substituted aryl, optionally substituted heteroaryl, optionally substituted cycloalkyl, optionally substituted non-aromatic heterocyclyl, or a bond;

R$^2$ and R$^3$ are independently H, optionally substituted C$_{1-6}$ alkyl, optionally substituted C$_{1-9}$ cyclic, optionally substituted C$_{3-9}$ heterocyclyl, or halogen, or R$^2$ and R$^3$ together form an optionally substituted C$_{3-9}$ cyclic or optionally substituted 3- to 9-membered heterocyclyl ring;

Z is O, SO$_{0-2}$, NR, C(R$^7$)$_2$, alkenyl or alkynyl;

R$^1$ is optionally substituted phenyl, optionally substituted 5- or 6-membered heteroaryl, or optionally substituted non-aromatic heterocyclic;

R$^4$ is H, C(R$^7$)$_2$, aryl, or heteroaryl;

R$^5$ is H, nitrile, an optionally substituted aryl, an optionally substituted heterocycle, optionally substituted C$_1$-C$_6$ alkyl, optionally substituted C$_3$-C$_9$ cycloalkyl, or

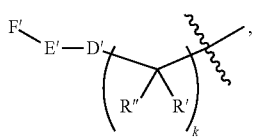

where
k is 1, 2, 3, 4, or 5;
R' and R" are each independently selected from the group consisting of H, optionally substituted alkyl, —OR, halogen (e.g., F, Cl, Br, I), —N(R)$_2$, optionally substituted cycloalkyl, and optionally substituted heterocyclyl;
or R' and R" may together form an optionally substituted 3- to 6-membered cycloalkyl or optionally substituted 3- to 6-membered non-aromatic heterocycle;

D' is selected from the group consisting of —O—, —NR—, —OCONR—, —OCO—, —CO—, —CO(NR)—, —SO$_{0-2}$—, —SO$_{0-2}$NR—, —NRSO$_2$—, —NRCO—, —NRSO$_2$NR—, —NRCOO—, —NRCONR—, and —NRC(NR)NR—;

E' is selected from the group consisting of a bond, an optionally substituted C$_1$-C$_6$ alkyl, optionally substituted C$_1$-C$_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted C$_1$-C$_6$ alkyl, and optionally substituted cycloalkyl;

R$^7$ is independently selected from the group consisting of H, halogen, optionally substituted C$_1$-C$_6$ alkyl, optionally substituted cycloalkyl, —OR, and —N(R); and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

R$^9$ is H, nitrile, halogen, —C(O)(optionally substituted alkyl), optionally substituted heterocycle, optionally substituted cyclic ring, or optionally substituted alkyl; provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

In some embodiments of a compound of Formula (III), X is O, S, SO, or SO$_2$. In some embodiments, X is O. In some embodiments, X is S. In some embodiments, X is NR. In some embodiments, X is NH. In some embodiments, X is SO. In some embodiments, X is SO$_2$.

In some embodiments of a compound of Formula (III), Y and Y' are not both phenylene.

In some embodiments of a compound of Formula (III), Y' is selected from the group consisting of an alkyne, an optionally substituted heteroaryl, an optionally substituted C$_3$-C$_{10}$ cycloalkyl, and an optionally substituted non-aromatic heterocycle (containing one or more O, S, SO, SO$_2$, N, or NR). In some embodiments, Y' is selected from:

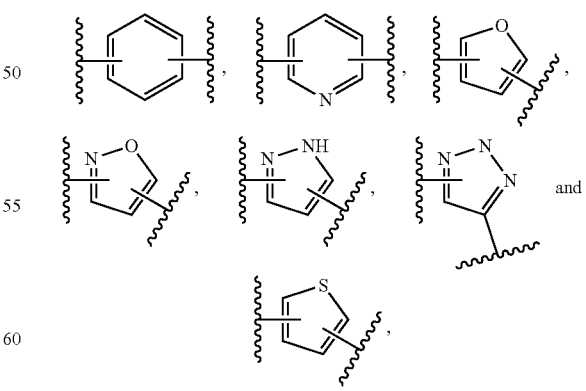

each of which may be optionally substituted. In some embodiments, Y' is cyclobutane, cyclobutene, propellane (such as, but not limited to, [1.1.1.0$^{1,3}$] propellane), cubane, or

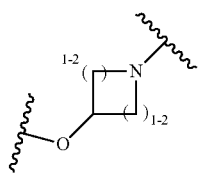

In some embodiments of a compound of Formula (III), Y is selected from the group consisting of an optionally substituted alkyl, an optionally substituted alkenyl, an optionally substituted aryl, an optionally substituted heteroaryl, an optionally substituted $C_3$-$C_{10}$ cycloalkyl, and an optionally substituted non-aromatic heterocycle (containing one or more O, S, SO, $SO_2$, B, N, or NR). In some embodiments, Y is selected from:

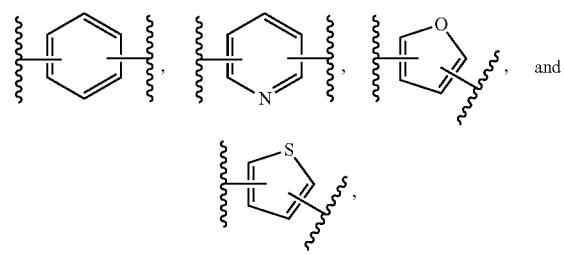

each of which may be optionally substituted. In some embodiments, Y is

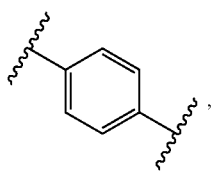 [SMILES: *c1ccc(*)cc1]

which may be optionally substituted; for example, the phenylene may be substituted with $C_1$-$C_6$ alkyl, cycloalkyl, halogen, —$NR_2$, —$SF_5$ or —OR, or a combination of two or more thereof. In some embodiments, Y is phenylene optionally substituted with $C_1$-$C_6$ alkyl, cycloalkyl, —$CF_3$, —OR, —CN, —$CO_2R$, halogen, —SR, —SOR, —$SO_2R$, —$SF_5$, or —$NR_2$, or a combination of two or more thereof. In some embodiments, the phenylene is substituted by methyl or perfluoromethyl. In some embodiments, the substitution is at a position ortho to the alkyne. Other examples within these embodiments, include phenylene moieties substituted by one or more fluoro moiety. For example, the phenylene moieties may be

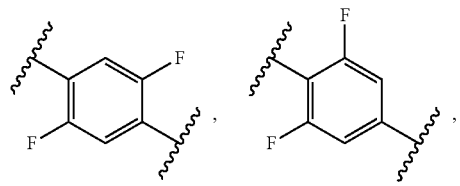

-continued

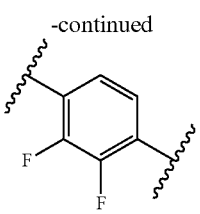

or further substituted variants thereof, e.g.,

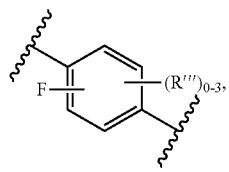

where R''' is a halogen (e.g., F, Cl, I, or Br), nitrile, a $C_1$-$C_6$ alkyl, or O—$C_1$-$C_6$ alkyl. In some embodiments, the phenylene is di-substituted, for example,

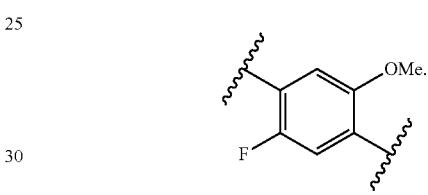

In some embodiments, Y is phenylene optionally substituted with $C_1$-$C_6$ alkyl, $C_1$-$C_6$ haloalkyl, halogen, $C_1$-$C_6$ alkoxy, nitrile, or a combination of two or more thereof. In some embodiments, Y is cyclobutane, cyclobutene, propellane (such as, but not limited to, $[1.1.1.0^{1,3}]$ propellane), cubane, or

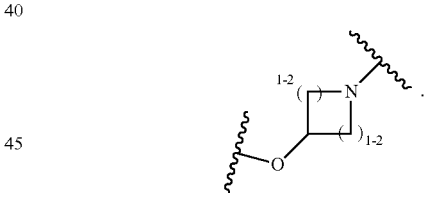

In some embodiments of a compound of Formula (III), Z is selected from the group consisting of O, S, and $C(R^7)_2$, where $R^7$ is independently H, halogen, optionally substituted alkyl, optionally substituted cycloalkyl, or —$N(R)_2$. In some embodiments, R or $R^7$ is H. In some embodiments, $R^7$ is H. In some embodiments, Z is $CH_2$. In some embodiments, Z is O. In some embodiments, Z is S. In some embodiments, Z is selected from the group consisting of O, S and $CH_2$.

In some embodiments of a compound of Formula (III), $R^5$ is an optionally substituted aryl. In some embodiments, $R^5$ is an unsubstituted or substituted phenyl. In some embodiments, the phenyl is substituted with one or more of alkyl, —OR, —CN, —$CO_2R$, halogen, —SR, —SOR, —$SO_2R$, —$SF_5$, or —$NR_2$, or any combination thereof.

In some embodiments of a compound of Formula (III), $R^5$ is heterocyclyl (e.g., a morpholine or pyridine), optionally substituted with one or more alkyl, —OR, —CN, —$CO_2R$, halogen, —SR, —SOR, —$SO_2R$, —$SF_5$, or —$NR_2$, or any combination thereof.

In some embodiments of a compound of Formula (III), R⁵ is C₁-C₆ alkyl optional substituted with alkoxy, hydroxy, amino, non-aromatic heterocyclyl, cycloalkyl, aryl, heteroaryl. In some embodiments, R⁵ is H.

In some embodiments of a compound of Formula (III), R⁵ is

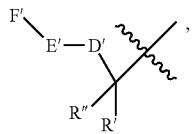

where
D' is selected from the group consisting of —O—, —NR—, —OCONR—, —OCO—, —NRSO₂—, —NRCO—, —NRSO₂NR—, —NRCOO—, —NRCONR—, and —NRC(NR)NR—; E' is selected from the group consisting of a bond, an optionally substituted C₁-C₆ alkyl, optionally substituted C₁-C₆ alkenyl, and optionally substituted cycloalkyl; and F' is selected from the group consisting of H, halogen, an optionally substituted cycloalkyl, an optionally substituted non-aromatic heterocycle, an optionally substituted aryl, and an optionally substituted heteroaryl.

In some embodiments of a compound of Formula (III), D' is selected from the group consisting of O, NH, OCONH, OCO, NHSO₂, NHCO, NHSO₂NH, NHCOO, and NHCONH. In some embodiments, D' is —O—, —NH—, —OCONH—, —OCO—, —NHCO—, or —NHCOO—. In some embodiments, D' is —O—. In some embodiments, D' is —NH—. In some embodiments, D' is —OCONH—. In some embodiments, D' is —OCO—. In some embodiments, D' is —NHCO—. In some embodiments, D' is —NHCOO—.

In some embodiments of a compound of Formula (III), E' is a bond, an optionally substituted C₁-C₆ alkyl, or optionally substituted cycloalkyl. In some embodiments, E' is an optionally substituted C₁-C₆ alkyl. In some embodiments, E' is an optionally substituted C₁-C₆ alkyl and F' is H. In some embodiments, E' is an optionally substituted C₃-C₆ cycloalkyl, (e.g., optionally substituted with alkyl, halogen, or —OR). In some embodiments, the cycloalkyl is specifically selected from, e.g., one of the following: cyclopropyl, cyclobutyl, cyclopentyl, and cyclohexyl, each of which may be optionally substituted. In some embodiments, E' is C₁-C₆ alkyl and F' is H.

In some embodiments of a compound of Formula (III), F' is an optionally substituted cycloalkyl, an optionally substituted non-aromatic heterocycle, an optionally substituted aryl, or an optionally substituted heteroaryl, each of which is described below in further detail. In some embodiments, F' is substituted with one or more alkyl, perfluoroalkyl (e.g., CF₃), —OR, —CN, —CO₂R, halogen, —SR, —SOR, —SO₂R, —SF₅, or —NR₂, or any combination thereof. In some embodiments, F' is not substituted.

In some embodiments of a compound of Formula (III), F' is an optionally substituted cycloalkyl. For example, F' may be a C₃-C₆ cycloalkyl, optionally substituted with alkyl, halogen, or —OR. In some embodiments, the cycloalkyl is specifically selected from, e.g., one of the following: cyclopropyl, cyclobutyl, cyclopentyl, and cyclohexyl, each of which may be optionally substituted. In some embodiments, the cycloalkyl is specifically selected from, e.g., one of the following: cyclopropyl, cyclobutyl, cyclopentyl, cyclohexyl, and propellane, each of which may be optionally substituted. In some embodiments, E' is a bond and F' is an optionally substituted cycloalkyl. In some embodiments, E' is optionally substituted C₁-C₆ alkyl and F' is an optionally substituted cycloalkyl.

In some embodiments of a compound of Formula (III), F' is an optionally substituted heterocycle. For example, F' may be a 4-6 membered non-aromatic heterocycle, optionally substituted with alkyl, halogen, or OR. In some embodiments, the heterocycle contains one or more heteroatom selected from: O, S, SO, SO₂, B, N, and NR. Particular embodiments include, e.g., morpholine, azetidine, alkyl-piperidine, alkyl-piperazine, alkyl-diazepane, thiomorpholine 1,1-dioxide, isoindoline-1,3-dione, tetrahydropyran, and pyrrolidone. In some embodiments, E' is a bond and F' is an optionally substituted non-aromatic heterocycle. In some embodiments, E' is optionally substituted C₁-C₆ alkyl and F' is an optionally substituted non-aromatic heterocycle.

In some embodiments of a compound of Formula (III), F' is an optionally substituted aryl. For example, F' may be a C₆-C₁₀ aryl, e.g., a phenyl, that is optionally substituted, e.g., with one or more of alkyl, perfluoroalkyl (e.g., CF₃), —OR, —CN, —CO₂R, halogen, —SR, —SOR, —SO₂R, —SF₅, or —NR₂, or any combination thereof. In some embodiments, E' is a bond and F' is an optionally substituted aryl. In some embodiments, E' is optionally substituted C₁-C₆ alkyl and F' is an optionally substituted aryl.

In some embodiments of a compound of Formula (III), F' is an optionally substituted heteroaryl. For example, F' may be a 5-6 membered heteroaryl, optionally substituted with alkyl, halogen, or OR. In some embodiments, the heteroaryl contains one or more heteroatom selected from O, S, SO, N, and NR. Particular embodiments include, e.g., alkyl-triazole, tetrazole, imidazole, and isoxazole. In some embodiments, E' is a bond and F' is an optionally substituted heteroaryl. In some embodiments, E' is optionally substituted C₁-C₆ alkyl and F' is an optionally substituted heteroaryl.

In some embodiments of a compound of Formula (III), R⁵ is:

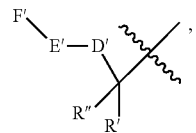

where
R' and R" are each independently selected from the group consisting of H, optionally substituted alkyl, —OR, halogen (e.g., F, Cl, Br, I), —N(R)₂, optionally substituted cycloalkyl, and optionally substituted non-aromatic heterocyclyl. In some embodiments, R' and R" are each H, or at least one of R' and R" is methyl and any remaining R' or R" is H. In some embodiments, R' and R" are each H. In some embodiments, at least one of R' and R" is optionally substituted alkyl and any remaining R' or R" is H. In some embodiments, the optionally substituted alkyl is a C₁-C₆ alkyl or C₁-C₆ perfluoroalkyl. In some embodiments, the optionally substituted alkyl is methyl. In some embodiments, R' and R" are each independently optionally substituted C₁-C₆ alkyl.

Alternatively, R' and R" together may form a 3- to 6-membered cycloalkyl or 3- to 6-membered non-aromatic heterocycle that is optionally substituted. In some embodiments, the 3- to 6-membered cycloalkyl or 3- to 6-membered non-aromatic heterocycle is substituted by one or more R⁷, as defined previously. In additional embodiments, R' and R" form a cyclopropyl, cyclobutyl, cyclopentyl, or cyclohexyl. In other embodiments, R' and R" form an oxetane. In some embodiments, R' and R" form an optionally substituted azetidine, oxetane, pyrrolidone or piperidine. In some embodiments, the nitrogen of the azetidine, pyrrolidone or piperidine may be substituted with R, $SO_2R$, COR, $SO_2NR_2$, $CONR_2$ and COOR. In some embodiments, when R' and R" form a ring, e.g., an optionally substituted cyclopropyl, cyclobutyl, cyclopentyl, or cyclohexyl, azetidine, oxetane, pyrrolidone or piperidine, then D'-E'-F' together form an —OH (i.e., D' is —O—, E' is a bond and F' is H).

In some embodiments of a compound of Formula (III), R' and R" are both H, D' is —CO—, E' is a bond, and F' is an optionally substituted non-aromatic heterocycle. In some embodiments of a compound of Formula (III), R' and R" are both H, D' is —CO—, E' is a bond, and F' is an optionally substituted pyrrolidine, an optionally substituted piperidine, an optionally substituted piperazine, an optionally substituted homopiperazine, or an optionally substituted azepane.

In some embodiments of a compound of Formula (III), R' and R" are both H, k is 1, D' is —CO—, E' is a bond, and F' is an optionally substituted non-aromatic heterocycle. In some embodiments of a compound of Formula (III), R' and R" are both H, D' is —CO—, E' is a bond, and F' is an optionally substituted pyrrolidine, an optionally substituted piperidine, an optionally substituted piperazine, an optionally substituted homopiperazine, or an optionally substituted azepane.

In some embodiments of a compound of Formula (III), $R^1$ is an optionally substituted phenyl or an optionally substituted 5- or 6-membered heteroaryl. For example, in some embodiments, $R^1$ is optionally substituted phenyl or optionally substituted pyridine. In some embodiments, $R^1$ is an unsubstituted phenyl or an unsubstituted pyridine. In some embodiments, R' is a pyridine. In some embodiments the pyridine is attached at the 2 position, the 3 position or the 4 position. In some embodiments the pyridine is attached at the 3 position. In some embodiments, $R^1$ is optionally substituted non-aromatic heterocyclic.

In some embodiments of a compound of Formula (III), $R^2$ and $R^3$ are both H and $R^9$ is optionally substituted alkyl. In some embodiments of a compound of Formula (III), $R^2$ and $R^3$ are both H and $R^9$ is —C(O)(optionally substituted alkyl). In some embodiments of a compound of Formula (III), $R^2$ and $R^3$ are both H and $R^9$ is optionally substituted cyclic ring. In some embodiments of a compound of Formula (III), $R^2$ and $R^3$ are both H and $R^9$ is —C(O)(optionally substituted alkyl).

In some embodiments of a compound of Formula (III), $R^2$ and $R^3$ are independently an optionally substituted $C_{1-9}$ cyclic, optionally substituted $C_{3-9}$ heterocyclic, or halogen, or $R^2$ and $R^3$ together form an optionally substituted $C_{3-9}$ cyclic or optionally substituted 3- to 9-membered heterocyclic ring; and $R^9$ is nitrile, halogen, or optionally substituted alkyl. In some embodiments, $R^2$ is a $C_1$-$C_6$ alkyl, a $C_3$-$C_{10}$ cycloalkyl (including cycloalkenyl), or a heterocycle, each of which maybe optionally substituted; and $R^9$ is nitrile, halogen, or optionally substituted alkyl.

In some embodiments of a compound of Formula (III), $R^2$ and $R^3$ together form an optionally substituted $C_{3-9}$ cyclic or optionally substituted 3- to 9-membered heterocyclic ring, for example, a $C_3$-$C_{10}$ cycloalkyl (including cycloalkenyl), or a heterocycle, each of which maybe optionally substituted; and $R^9$ is nitrile, halogen, or optionally substituted alkyl. Exemplary individual embodiments when $R^2$ and $R^3$ together form an optionally substituted $C_{3-9}$ cyclic or optionally substituted 3- to 9-membered heterocyclic ring, include cyclopropyl, cyclobutyl, cyclopentyl, cyclohexyl, cyclopentene, and cyclohexene, each of which may be optionally substituted, for example, by one or more deuterium or fluorine moiety. Other embodiments include bicyclic structures, such as:

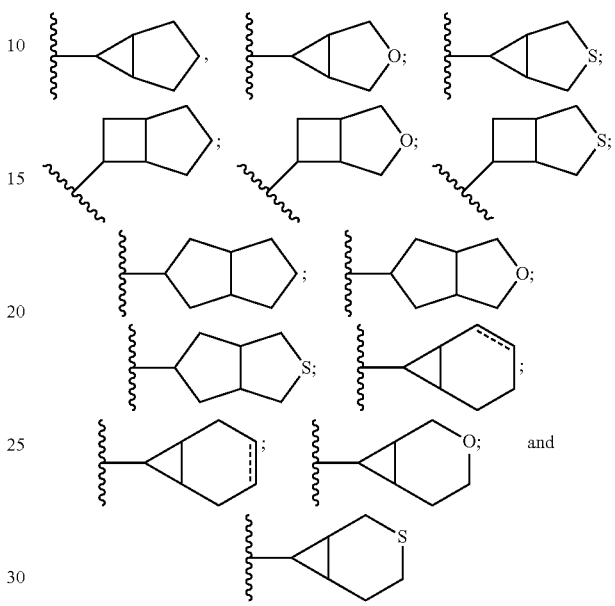

where
one or more of the dashed bonds may optionally be a double bond and ⸳⸳⸳ indicates attachment to Z. In some embodiments, $R^2$ and $R^3$ together form a cyclopropyl, cyclopentyl or cyclohexene, and $R^9$ is nitrile, halogen, or optionally substituted alkyl. In some embodiments, $R^2$ and $R^3$ together form a cyclopropyl, and $R^9$ is nitrile, halogen, or optionally substituted alkyl. In some embodiments, $R^2$ and $R^3$ together form a cyclopentyl, and $R^9$ is nitrile, halogen, or optionally substituted alkyl. In some embodiments, $R^2$ and $R^3$ together form a cyclohexene, and $R^9$ is nitrile, halogen, or optionally substituted alkyl.

In some embodiments of a compound of Formula (III), one or more hydrogens in $R^2$ or $R^3$, or in both $R^2$ and $R^3$ are replaced with deuterium. In some embodiments, $R^2$ and $R^3$ form a perdeuterated cycloalkyl ring. In some embodiments, $R^2$ and $R^3$ form a perdeuterated cyclopentane

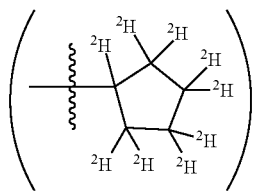

and ⸳⸳⸳ indicates attachment to Z.

In some embodiments of a compound of Formula (III), A is H, halogen, nitrile, optionally substituted alkyl, optionally substituted alkenyl, optionally substituted alkynyl, —CON$(R)_2$, or —COOR. In some embodiments, A is H. In some embodiments, A is halogen. In some embodiments, A is nitrile. In some embodiments, A is optionally substituted alkyl. In some embodiments, A is optionally substituted alkenyl. In some embodiments, A is optionally substituted alkynyl. In some embodiments, A is —COR, —CON(R)$_2$, or —COOR.

In some embodiments of a compound of Formula (III), $R^2$, $R^3$, and $R^9$ cannot all be H.

In some embodiments, the compounds of the present disclosure are selected from the compounds of Table I or a pharmaceutically acceptable salt or prodrug thereof.

TABLE I**

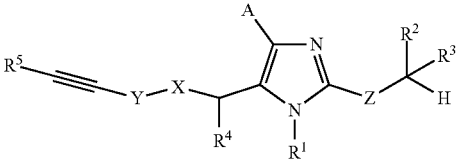

| $R^5$ | Y | X | $R^4$ | $R^1$ | Z | $R^2$ | $R^3$ |
|---|---|---|---|---|---|---|---|
| H | alkyl or alkenyl | O | H | optionally substituted 5- or 6-membered heteroaryl | S | a $C_{3-9}$ cyclic or $C_{3-9}$ heterocyclic ring | |
| nitrile | alkyl or alkenyl | O | H | optionally substituted 5- or 6-membered heteroaryl | S | a $C_{3-9}$ cyclic or $C_{3-9}$ heterocyclic ring | |
| optionally substituted aryl | alkyl or alkenyl | O | H | optionally substituted 5- or 6-membered heteroaryl | S | a $C_{3-9}$ cyclic or $C_{3-9}$ heterocyclic ring | |
| optionally substituted heterocycle | alkyl or alkenyl | O | H | optionally substituted 5- or 6-membered heteroaryl | S | a $C_{3-9}$ cyclic or $C_{3-9}$ heterocyclic ring | |
| optionally substituted $C_1$-$C_6$ alkyl | alkyl or alkenyl | O | H | optionally substituted 5- or 6-membered heteroaryl | S | a $C_{3-9}$ cyclic or $C_{3-9}$ heterocyclic ring | |
| optionally substituted $C_3$-$C_9$ cycloalkyl | alkyl or alkenyl | O | H | optionally substituted 5- or 6-membered heteroaryl | S | a $C_{3-9}$ cyclic or $C_{3-9}$ heterocyclic ring | |
| 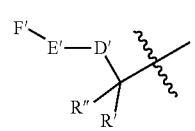 | alkyl or alkenyl | O | H | optionally substituted 5- or 6-membered heteroaryl | S | a $C_{3-9}$ cyclic or $C_{3-9}$ heterocyclic ring | |
| H | optionally substituted aryl | O | H | optionally substituted 5- or 6-membered heteroaryl | S | a $C_{3-9}$ cyclic or $C_{3-9}$ heterocyclic ring | |
| nitrile | optionally substituted aryl | O | H | optionally substituted 5- or 6-membered heteroaryl | S | a $C_{3-9}$ cyclic or $C_{3-9}$ heterocyclic ring | |
| optionally substituted aryl | optionally substituted aryl | O | H | optionally substituted 5- or 6-membered heteroaryl | S | a $C_{3-9}$ cyclic or $C_{3-9}$ heterocyclic ring | |
| optionally substituted heterocycle | optionally substituted aryl | O | H | optionally substituted 5- or 6-membered heteroaryl | S | a $C_{3-9}$ cyclic or $C_{3-9}$ heterocyclic ring | |
| optionally substituted $C_1$-$C_6$ alkyl | optionally substituted aryl | O | H | optionally substituted 5- or 6-membered heteroaryl | S | a $C_{3-9}$ cyclic or $C_{3-9}$ heterocyclic ring | |
| optionally substituted $C_3$-$C_9$ cycloalkyl | optionally substituted aryl | O | H | optionally substituted 5- or 6-membered heteroaryl | S | a $C_{3-9}$ cyclic or $C_{3-9}$ heterocyclic ring | |
| 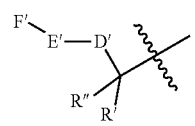 | optionally substituted aryl | O | H | optionally substituted 5- or 6-membered heteroaryl | S | a $C_{3-9}$ cyclic or $C_{3-9}$ heterocyclic ring | |
| H | optionally substituted aryl | O | H | optionally substituted 5- or 6-membered heteroaryl | S | a $C_{3-9}$ cyclic or $C_{3-9}$ heterocyclic ring | |
| nitrile | optionally substituted aryl | O | H | optionally substituted 5- or 6-membered heteroaryl | S | a $C_{3-9}$ cyclic or $C_{3-9}$ heterocyclic ring | |
| optionally substituted aryl | optionally substituted aryl | O | H | optionally substituted 5- or 6-membered heteroaryl | S | a $C_{3-9}$ cyclic or $C_{3-9}$ heterocyclic ring | |

TABLE I**-continued

| R⁵ | Y | X | R⁴ | R¹ | Z | R² | R³ |
|---|---|---|---|---|---|---|---|
| optionally substituted heterocycle | optionally substituted aryl | O | H | optionally substituted 5- or 6-membered heteroaryl | S | a $C_{3-9}$ cyclic or $C_{3-9}$ heterocyclic ring | |
| optionally substituted $C_1$-$C_6$ alkyl | optionally substituted aryl | O | H | optionally substituted 5- or 6-membered heteroaryl | S | a $C_{3-9}$ cyclic or $C_{3-9}$ heterocyclic ring | |
| optionally substituted $C_3$-$C_9$ cycloalkyl | optionally substituted aryl | O | H | optionally substituted 5- or 6-membered heteroaryl | S | a $C_{3-9}$ cyclic or $C_{3-9}$ heterocyclic ring | |
| 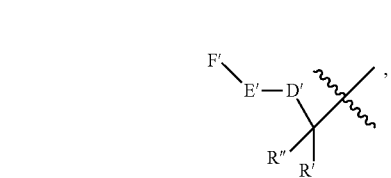 | optionally substituted aryl | O | H | optionally substituted 5- or 6-membered heteroaryl | S | a $C_{3-9}$ cyclic or $C_{3-9}$ heterocyclic ring | |

**A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)₂, or —COOR.

In some embodiments, when R⁵ is the moiety can be, for example, one of the following of Table II. In some embodiments, one or more of the moieties in Table II are substituted (e.g., E' is an optionally substituted $C_1$-$C_6$ alkyl).

TABLE II

| F' | E' | D' | R' | R" |
|---|---|---|---|---|
| H | $C_1$-$C_6$ alkyl | —O— | H | H |
| H | $C_1$-$C_6$ alkyl | —NR— | H | H |
| H | $C_1$-$C_6$ alkyl | —OCONR— | H | H |
| H | $C_1$-$C_6$ alkyl | —OCO— | H | H |
| H | $C_1$-$C_6$ alkyl | —NRSO₂— | H | H |
| H | $C_1$-$C_6$ alkyl | —NRCO— | H | H |
| H | $C_1$-$C_6$ alkyl | —NRSO₂NR— | H | H |
| H | $C_1$-$C_6$ alkyl | —NRCOO— | H | H |
| H | $C_1$-$C_6$ alkyl | —NRCONR— | H | H |
| H | $C_1$-$C_6$ alkyl | —NRC(NR)NR— | H | H |
| optionally substituted cycloalkyl | $C_1$-$C_6$ alkyl | —O— | H | H |
| optionally substituted cycloalkyl | $C_1$-$C_6$ alkyl | —NR— | H | H |
| optionally substituted cycloalkyl | $C_1$-$C_6$ alkyl | —OCONR— | H | H |
| optionally substituted cycloalkyl | $C_1$-$C_6$ alkyl | —OCO— | H | H |
| optionally substituted cycloalkyl | $C_1$-$C_6$ alkyl | —NRSO₂— | H | H |
| optionally substituted cycloalkyl | $C_1$-$C_6$ alkyl | —NRCO— | H | H |
| optionally substituted cycloalkyl | $C_1$-$C_6$ alkyl | —NRSO₂NR— | H | H |
| optionally substituted cycloalkyl | $C_1$-$C_6$ alkyl | —NRCOO— | H | H |
| optionally substituted cycloalkyl | $C_1$-$C_6$ alkyl | —NRCONR— | H | H |
| optionally substituted cycloalkyl | $C_1$-$C_6$ alkyl | —NRC(NR)NR— | H | H |
| optionally substituted heterocycle | $C_1$-$C_6$ alkyl | —O— | H | H |
| optionally substituted heterocycle | $C_1$-$C_6$ alkyl | —NR— | H | H |
| optionally substituted heterocycle | $C_1$-$C_6$ alkyl | —OCONR— | H | H |
| optionally substituted heterocycle | $C_1$-$C_6$ alkyl | —OCO— | H | H |
| optionally substituted heterocycle | $C_1$-$C_6$ alkyl | —NRSO₂— | H | H |
| optionally substituted heterocycle | $C_1$-$C_6$ alkyl | —NRCO— | H | H |
| optionally substituted heterocycle | $C_1$-$C_6$ alkyl | —NRSO₂NR— | H | H |
| optionally substituted heterocycle | $C_1$-$C_6$ alkyl | —NRCOO— | H | H |
| optionally substituted heterocycle | $C_1$-$C_6$ alkyl | —NRCONR— | H | H |
| optionally substituted heterocycle | $C_1$-$C_6$ alkyl | —NRC(NR)NR— | H | H |
| optionally substituted aryl | $C_1$-$C_6$ alkyl | —O— | H | H |
| optionally substituted aryl | $C_1$-$C_6$ alkyl | —NR— | H | H |

TABLE II-continued

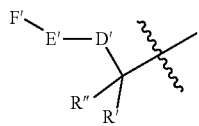

| F' | E' | D' | R' | R" |
|---|---|---|---|---|
| optionally substituted aryl | C₁-C₆ alkyl | —OCONR— | H | H |
| optionally substituted aryl | C₁-C₆ alkyl | —OCO— | H | H |
| optionally substituted aryl | C₁-C₆ alkyl | —NRSO₂— | H | H |
| optionally substituted aryl | C₁-C₆ alkyl | —NRCO— | H | H |
| optionally substituted aryl | C₁-C₆ alkyl | —NRSO₂NR— | H | H |
| optionally substituted aryl | C₁-C₆ alkyl | —NRCOO— | H | H |
| optionally substituted aryl | C₁-C₆ alkyl | —NRCONR— | H | H |
| optionally substituted aryl | C₁-C₆ alkyl | —NRC(NR)NR— | H | H |
| optionally substituted heteroaryl | C₁-C₆ alkyl | —O— | H | H |
| optionally substituted heteroaryl | C₁-C₆ alkyl | —NR— | H | H |
| optionally substituted heteroaryl | C₁-C₆ alkyl | —OCONR— | H | H |
| optionally substituted heteroaryl | C₁-C₆ alkyl | —OCO— | H | H |
| optionally substituted heteroaryl | C₁-C₆ alkyl | —NRSO₂— | H | H |
| optionally substituted heteroaryl | C₁-C₆ alkyl | —NRCO— | H | H |
| optionally substituted heteroaryl | C₁-C₆ alkyl | —NRSO₂NR— | H | H |
| optionally substituted heteroaryl | C₁-C₆ alkyl | —NRCOO— | H | H |
| optionally substituted heteroaryl | C₁-C₆ alkyl | —NRCONR— | H | H |
| optionally substituted heteroaryl | C₁-C₆ alkyl | —NRC(NR)NR— | H | H |
| optionally substituted cycloalkyl | bond | —O— | H | H |
| optionally substituted cycloalkyl | bond | —NR— | H | H |
| optionally substituted cycloalkyl | bond | —OCONR— | H | H |
| optionally substituted cycloalkyl | bond | —OCO— | H | H |
| optionally substituted cycloalkyl | bond | —NRSO₂— | H | H |
| optionally substituted cycloalkyl | bond | —NRCO— | H | H |
| optionally substituted cycloalkyl | bond | —NRSO₂NR— | H | H |
| optionally substituted cycloalkyl | bond | —NRCOO— | H | H |
| optionally substituted cycloalkyl | bond | —NRCONR— | H | H |
| optionally substituted cycloalkyl | bond | —NRC(NR)NR— | H | H |
| optionally substituted heterocycle | bond | —NR— | H | H |
| optionally substituted heterocycle | bond | —OCONR— | H | H |
| optionally substituted heterocycle | bond | —OCO— | H | H |
| optionally substituted heterocycle | bond | —NRSO₂— | H | H |
| optionally substituted heterocycle | bond | —NRCO— | H | H |
| optionally substituted heterocycle | bond | —NRSO₂NR— | H | H |
| optionally substituted heterocycle | bond | —NRCOO— | H | H |

TABLE II-continued

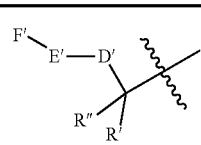

| F' | E' | D' | R' | R" |
|---|---|---|---|---|
| optionally substituted heterocycle | bond | —NRCONR— | H | H |
| optionally substituted heterocycle | bond | —NRC(NR)NR— | H | H |
| optionally substituted aryl | bond | —NR— | H | H |
| optionally substituted aryl | bond | —OCONR— | H | H |
| optionally substituted aryl | bond | —OCO— | H | H |
| optionally substituted aryl | bond | —NRSO₂— | H | H |
| optionally substituted aryl | bond | —NRCO— | H | H |
| optionally substituted aryl | bond | —NRSO₂NR— | H | H |
| optionally substituted aryl | bond | —NRCOO— | H | H |
| optionally substituted aryl | bond | —NRCONR— | H | H |
| optionally substituted aryl | bond | —NRC(NR)NR— | H | H |
| optionally substituted heteroaryl | bond | —NR— | H | H |
| optionally substituted heteroaryl | bond | —OCONR— | H | H |
| optionally substituted heteroaryl | bond | —OCO— | H | H |
| optionally substituted heteroaryl | bond | —NRSO₂— | H | H |
| optionally substituted heteroaryl | bond | —NRCO— | H | H |
| optionally substituted heteroaryl | bond | —NRSO₂NR— | H | H |
| optionally substituted heteroaryl | bond | —NRCOO— | H | H |
| optionally substituted heteroaryl | bond | —NRCONR— | H | H |
| optionally substituted heteroaryl | bond | —NRC(NR)NR— | H | H |

In some embodiments, the compounds of the present disclosure are selected from the compounds of Table III (shown below) or a pharmaceutically acceptable salt or prodrug thereof. It should be noted that the moieties of the compounds of Table III fall within the scope of compounds of Formulae (I), (Ia), (Ib), (Ic), (IIa), (IIb), or (III). The present disclosure includes embodiments where one or more of the variable moieties of Formulae (I), (Ia), (Ib), (Ic), (IIa), (IIb), or (III) are represented by the equivalent moiety of one or more of the compounds of Table III without requiring the other specific moieties of the same compound of Table III.

Additional species within the scope of the disclosure are presented in Table III.

TABLE III
| No | Compound | Analytical Data; M + H (LC-HRMS) |
|---|---|---|
| 1 | 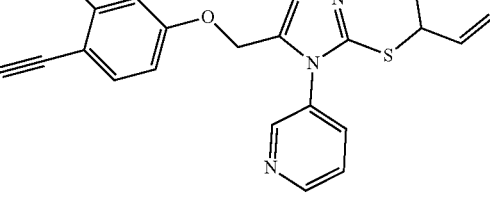 | 432.1740 |
| 2 | 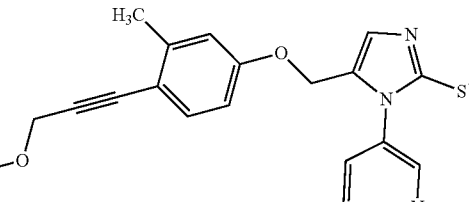 | 559.2375 |
| 3 | 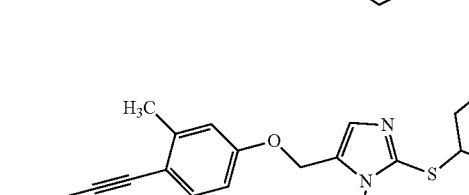 | 533.2220 |
| 4 | 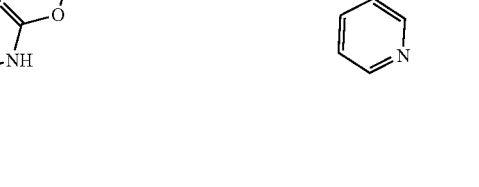 | 588.2645 |
| 5 | 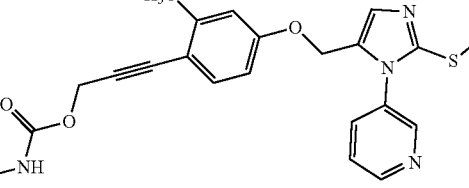 | 591.3118 |

TABLE III-continued

| No | Compound | Analytical Data; M + H (LC-HRMS) |
|---|---|---|
| 6 | | 476.1998 |
| 7 | | 490.2158 |
| 8 | | 473.2003 |
| 9 | | 528.2789 |
| 10 | | 502.2630 |

TABLE III-continued

| No | Compound | Analytical Data; M + H (LC-HRMS) |
|---|---|---|
| 11 | | 601.2956 |
| 12 | | 510.0842 |
| 13 | | 707.2370 |
| 14 | | 517.2268 |
| 15 | | 572.2689 |

TABLE III-continued

| No | Compound | Analytical Data; M + H (LC-HRMS) |
|---|---|---|
| 16 | | 412.1321 |
| 17 | | 392.1431 |
| 18 | | 466.1347 |
| 19 | | 624.1642 |
| 20 | | 507.1410 |

TABLE III-continued

| No | Compound | Analytical Data; M + H (LC-HRMS) |
|---|---|---|
| 21 | | 704.2937 |
| 22 | | 445.1691 |
| 23 | | 474.1843 |
| 24 | | 492.1949 |

TABLE III-continued

| No | Compound | Analytical Data; M + H (LC-HRMS) |
|---|---|---|
| 25 | | 463.1799 |
| 26 | | 542.3126 |
| 27 | | 504.1951 |
| 28 | | 478.2158 |
| 29 | | 529.2285 |

TABLE III-continued
| No | Compound | Analytical Data; M + H (LC-HRMS) |
|---|---|---|
| 30 | 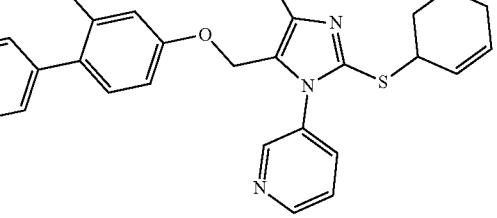 | 610.0829 |
| 31 | 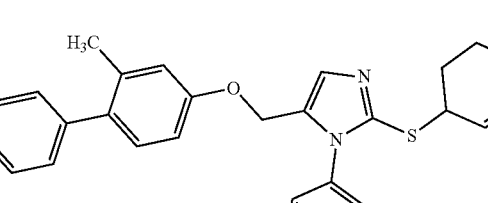 | 532.1720 |
| 32 | 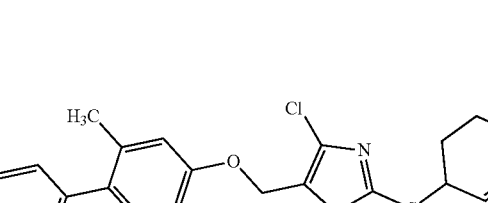 | 566.1334 |
| 33 | 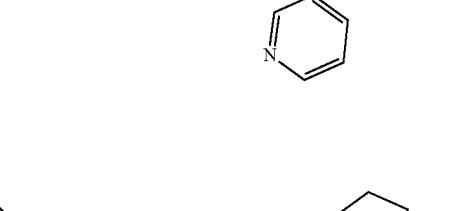 | 460.0486 |
| 34 | 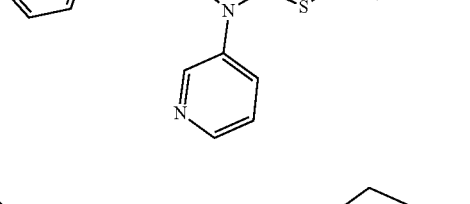 | 412.1242 |

TABLE III-continued
| No | Compound | Analytical Data; M + H (LC-HRMS) |
|---|---|---|
| 35 | 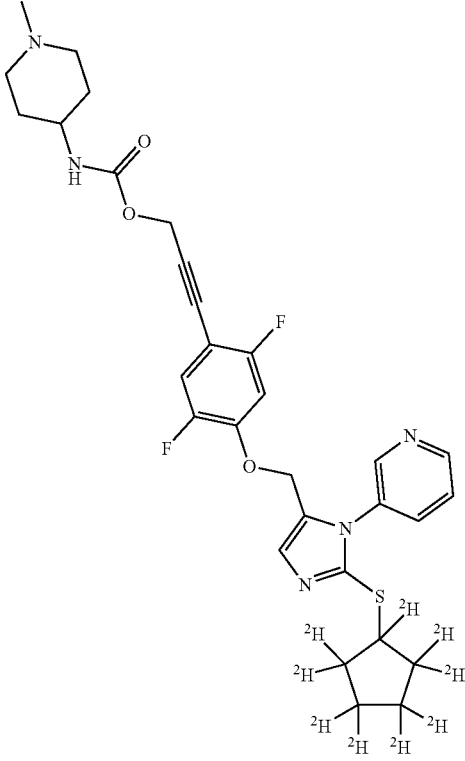 [SMILES: [2H]C1([2H])C([2H])([2H])C([2H])([2H])C([2H])(Sc2ncc(COc3cc(F)c(C#CCOC(=O)NC4CCN(C)CC4)cc3F)n2-c2cccnc2)C1([2H])[2H]] | 591.2907 |
| 36 | 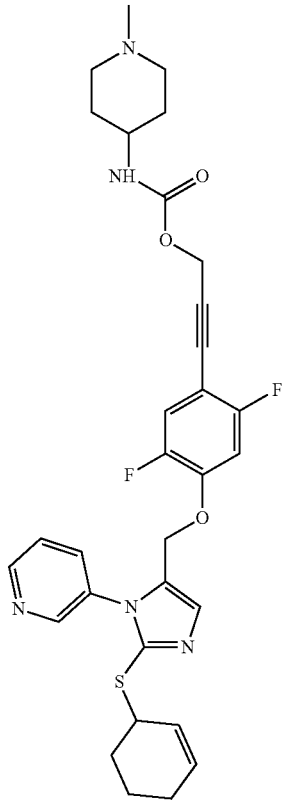 [SMILES: CN1CCC(NC(=O)OCC#Cc2cc(F)c(OCc3cnc(SC4C=CCCC4)n3-c3cccnc3)cc2F)CC1] | 594.2341 |

TABLE III-continued
| No | Compound | Analytical Data; M + H (LC-HRMS) |
|---|---|---|
| 37 | 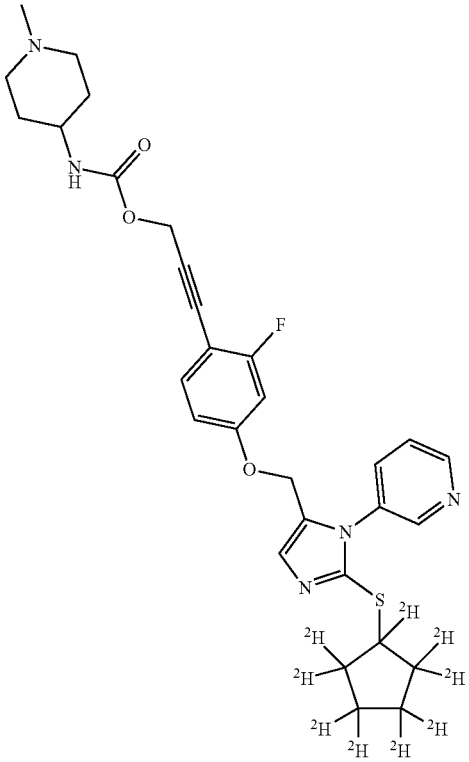 [SMILES: [2H]C1([2H])C([2H])([2H])C([2H])([2H])C([2H])(Sc2ncc(COc3ccc(C#CCOC(=O)NC4CCN(C)CC4)c(F)c3)n2-c2cccnc2)C1([2H])[2H]] | 573.2999 |
| 38 | 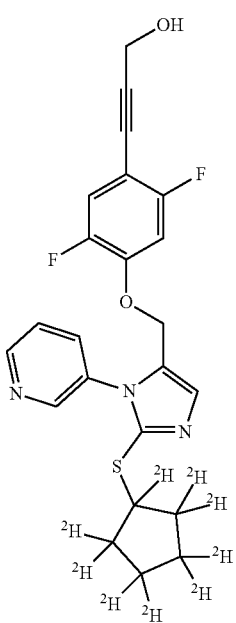 [SMILES: [2H]C1([2H])C([2H])([2H])C([2H])([2H])C([2H])(Sc2ncc(COc3cc(F)c(C#CCO)cc3F)n2-c2cccnc2)C1([2H])[2H]] | 451.1960 |

TABLE III-continued
| No | Compound | Analytical Data; M + H (LC-HRMS) |
|----|----------|----------------------------------|
| 39 | 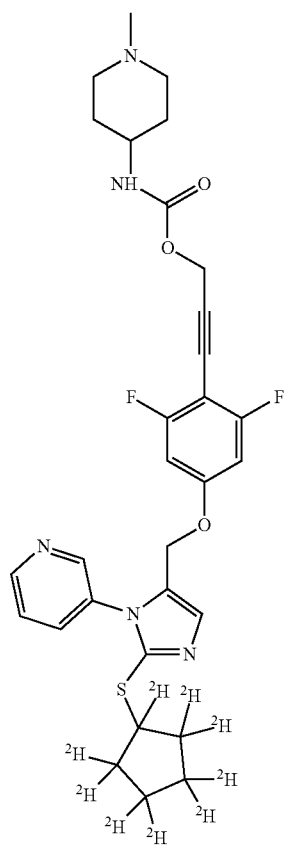 [SMILES: [2H]C1([2H])C([2H])([2H])C([2H])([2H])C([2H])(Sc2ncc(COc3cc(F)c(C#CCOC(=O)NC4CCN(C)CC4)c(F)c3)n2-c2cccnc2)C1([2H])[2H]] | 591.2912 |

TABLE III-continued

| No | Compound | Analytical Data; M + H (LC-HRMS) |
|---|---|---|
| 40 | | 620.2500 |
| 41 | | 480.1551 |

TABLE III-continued
| No | Compound | Analytical Data; M + H (LC-HRMS) |
|---|---|---|
| 42 | 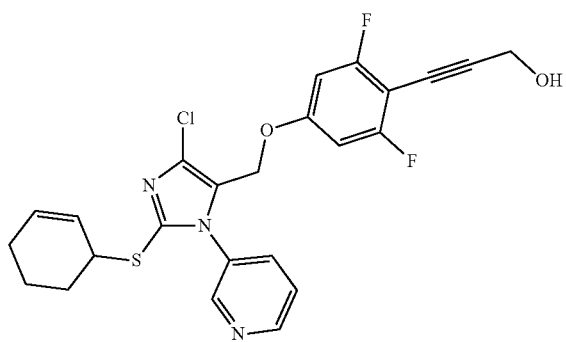 [SMILES: OCC#Cc1c(F)cc(OCc2c(Cl)nc(SC3C=CCCC3)n2-c2cccnc2)cc1F] | 488.1009 |
| 43 | 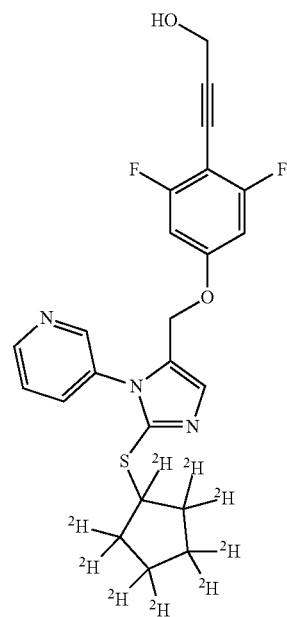 [SMILES: [2H]C1([2H])C([2H])([2H])C([2H])([2H])C([2H])(Sc2ncc(COc3cc(F)c(C#CCO)c(F)c3)n2-c2cccnc2)C1([2H])[2H]] | 451.1960 |

TABLE III-continued
| No | Compound | Analytical Data; M + H (LC-HRMS) |
|---|---|---|
| 44 | 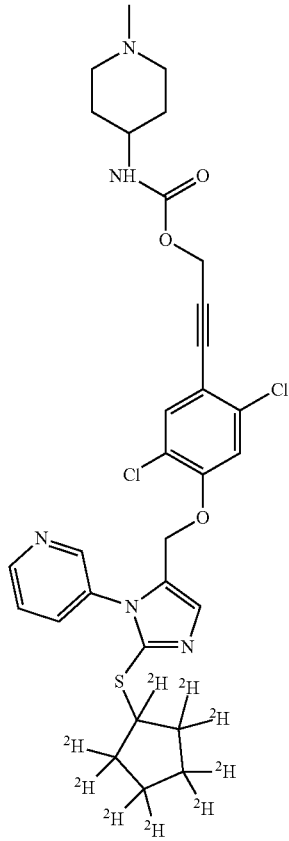 [SMILES: [2H]C1([2H])C([2H])([2H])C([2H])([2H])C([2H])(Sc2ncc(COc3cc(Cl)c(C#CCOC(=O)NC4CCN(C)CC4)cc3Cl)n2-c2cccnc2)C1([2H])[2H]] | 623.2320 |
| 45 | 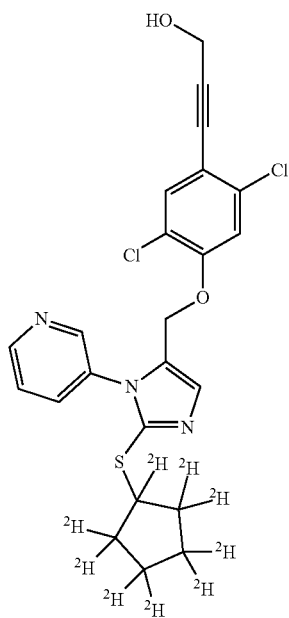 [SMILES: [2H]C1([2H])C([2H])([2H])C([2H])([2H])C([2H])(Sc2ncc(COc3cc(Cl)c(C#CCO)cc3Cl)n2-c2cccnc2)C1([2H])[2H]] | 483.1369 |

II. Methods of Treatment

In some embodiments, the compounds of the present disclosure have a Biomol Green™ $IC_{50}$ value of less than about 25 µM, meaning that at a concentration of 25 µM, the compounds inhibit the activity of p97 by at least about half. In other embodiments, the compounds inhibit the activity of p97 in the assay by more than half. Biomol Green (Enzo) is a bioluminescent, homogeneous assay that measures ADP formed from a biochemical reaction. Because of its high sensitivity, the assay is suitable for monitoring enzyme activities at very early substrate conversions requiring very low amount of enzymes. This is critical since inhibitor potency has to be demonstrated at the cellular level where ATP is present at millimolar concentrations. The assay procedure used may be the same as in Zhang et al., "Altered cofactor regulation with disease-associated p97/VCP mutations," *Proc. Natl. Acad. Sci. USA*, 112(14), E1705-E1714 (2015).

One aspect of the present technology includes methods of modulating p97 in a subject in need thereof. In some embodiments, the treatment of the subject in need thereof comprises administering a compound of the present disclosure (e.g., a compound of Formulae (I), (Ia), (Ib), (Ic), (IIa), (IIb), or (III), or Tables I or III) to the subject suspected of, or already suffering from elevated activity of p97, in an amount sufficient to cure, or at least partially arrest, the symptoms of elevated activity of p97. As such, some embodiments of the disclosure include methods of treating a subject in need thereof who is suffering from, suspected as having, or at risk of having elevated activity of p97.

In some embodiments, modulation of p97 includes allosteric modulation of p97. In some embodiments, modulation of p97 can be understood as activation of p97 or inhibition of p97. In some embodiments, modulation of p97 leads to at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, including increments therein, increase or decrease in p97 activity. In some embodiments, modulation of p97 leads to at least 2-, 3-, 4-, 5-, 6-, 7-, 8-, 9-, 10-, 15-, 20-, 25-, 30-, 35-, 40-, 45-, 50-, 55-, 60-, 65-, 70-, 75-, 80-, 85-, 90-, 95-, 100-, 200-, 300-, 400-, 500-, 600-, 700-, 800-, 900-, or 1000-fold, including increments therein, increase or decrease in p97 activity.

Another aspect of the present technology includes methods of inhibiting p97 in a subject in need thereof. In some embodiments, the treatment of the subject in need thereof comprises administering a compound of the present disclosure (e.g., a compound of Formulae (I), (Ia), (Ib), (Ic), (IIa), or (IIb), or Tables I or III) to the subject suspected of, or already suffering from elevated activity of p97, in an amount sufficient to cure, or at least partially arrest, the symptoms of elevated activity of p97. As such, some embodiments of the disclosure include methods of treating a subject in need thereof who is suffering from, suspected as having, or at risk of having elevated activity of p97.

Another aspect of the present technology includes methods of treating cancers or neurodegenerative disorders susceptible to treatment by p97 inhibition in a subject diagnosed as having, suspected as having, or at risk of having cancer or a neurodegenerative disorder susceptible to treatment by p97 inhibition. As such, some embodiments of the disclosure include methods of treating a subject in need thereof who is suffering from, suspected as having, or at risk of having cancer or a neurodegenerative disorder susceptible to treatment by p97 inhibition. In some embodiments, the treatment of the subject in need thereof comprises administering a compound of the present disclosure (e.g., a compound of Formulae (I), (Ia), (Ib), (Ic), (IIa), (IIb), or (III), or Tables I or III) to the subject suspected of, or already suffering from cancer or a neurodegenerative disorder susceptible to treatment by p97 inhibition, in an amount sufficient to cure, or at least partially arrest, the symptoms of the disease, including its complications and intermediate pathological phenotypes in development of the disease.

Another aspect of the present technology includes methods of treating cancers or neurodegenerative disorders susceptible to treatment by p97 modulation in a subject diagnosed as having, suspected as having, or at risk of having cancer or a neurodegenerative disorder susceptible to treatment by p97 modulation. As such, some embodiments of the disclosure include methods of treating a subject in need thereof who is suffering from, suspected as having, or at risk of having cancer or a neurodegenerative disorder susceptible to treatment by p97 modulation. In some embodiments, the treatment of the subject in need thereof comprises administering a compound of the present disclosure (e.g., a compound of Formulae (I), (Ia), (Ib), (Ic), (IIa), (IIb), or (III), or Tables I or III) to the subject suspected of, or already suffering from cancer or a neurodegenerative disorder susceptible to treatment by p97 modulation, in an amount sufficient to cure, or at least partially arrest, the symptoms of the disease, including its complications and intermediate pathological phenotypes in development of the disease.

In some embodiments, cancers susceptible to treatment by p97 inhibition or p97 modulation include but are not limited to solid tumor cancers, non-small cell lung carcinoma, multiple myeloma, or mantle cell lymphoma. In some embodiments, cancers susceptible to treatment by p97 inhibition or p97 modulation include a solid tumor. See Valle et al., "Critical Role of VCP/p97 in the Pathogenesis and Progression of Non-Small Cell Lung Carcinoma," *PlosOne*, 6(12): e29073 (2011) and Deshaies, "Proteotoxic crisis, the ubiquitin-proteasome system, and cancer therapy," *BMC Biology* 12(94), 1 (2014).

In some embodiments, neurodegenerative disorders susceptible to treatment by p97 inhibition or p97 modulation include but are not limited to inclusion body myopathy (IBM), Paget's disease of the bone (PDB), frontotemporal dementia (FTD) and amyotrophic lateral sclerosis (ALS)). Neurodegenerative disorders also include subjects having p97 mutations, and symptoms manifesting as, for example, Parkinsonism, ataxia, cataracts, dilated cardiomyopathy, hepatic fibrosis, and hearing loss.

Another aspect of the present technology includes methods of treating antibacterial and/or antiviral infection susceptible to treatment by p97 modulation in a subject diagnosed as having, suspected as having, or at risk of having antibacterial and/or antiviral infection susceptible to treatment by p97 modulation. As such, some embodiments of the disclosure include methods of treating a subject in need thereof who is suffering from, suspected as having, or at risk of having antibacterial and/or antiviral infection susceptible to treatment by p97 modulation. In some embodiments, the treatment of the subject in need thereof comprises administering a compound of the present disclosure (e.g., a compound of Formulae (Ia), (Ib), (IIa), (IIb), or (III), or Tables I or III) to the subject suspected of, or already suffering from antibacterial and/or antiviral infection susceptible to treatment by p97 modulation, in an amount sufficient to cure, or at least partially arrest, the symptoms of the disease, including its complications and intermediate pathological phenotypes in development of the disease.

The compound may be included in a pharmaceutical formulation, such as those disclosed herein, and may be administered in any pharmaceutically acceptable manner, including methods of administration described herein.

The compounds useful in the methods of the present technology are administered to a mammal in an amount effective in treating or preventing elevated activity of p97, cancers susceptible to treatment by p97 inhibition or p97 modulation, or neurodegenerative disorders susceptible to treatment by p97 inhibition or p97 modulation. The therapeutically effective amount can be determined by methods known in the art.

An effective amount of a compound useful in the methods of the present technology, for example in a pharmaceutical composition, may be administered to a mammal in need thereof by any of a number of well-known methods for administering pharmaceutical compounds. The compound may be administered systemically or locally. In one embodiment, the compound is administered intravenously. For example, the compounds useful in the methods of the present technology may be administered via rapid intravenous bolus injection. In some embodiments, the compound is administered as a constant rate intravenous infusion. The compound may also be administered orally, topically, intranasally, intramuscularly, subcutaneously, or transdermally. Other routes of administration include intracerebroventricularly or intrathecally. Intracerebroventiculatly refers to administration into the ventricular system of the brain. Intrathecally refers to administration into the space under the arachnoid membrane of the spinal cord.

The compounds useful in the methods of the present technology may also be administered to mammals by sustained or controlled release, as is known in the art. Sustained release administration is a method of drug delivery to achieve a certain level of the drug over a particular period of time. The level typically is measured by serum or plasma concentration.

In one preferred embodiment, the compounds are administered orally. In one preferred embodiment, the compounds are administered intravenously. In one preferred embodiment, the compounds are administered at less than about 1 gram per day. In other embodiments of the present technology, the compounds are administered at less than about 10, at less than about 9, at less than about 8, at less than about 7, at less than about 6, at less than about 5, at less than about 4, less than about 3, less than about 2, less than about 1, less than about 0.9, less than about 0.8, less than about 0.7, less than about 0.6, less than about 0.5, less than about 0.4, less than about 0.3, less than about 0.2, or less than about 0.1 grams per day, or any amount in between these values.

III. Pharmaceutical Formulations

For oral administration, liquid or solid dose formulations may be used. Some non-limiting examples of oral dosage formulations include tablets, gelatin capsules, pills, troches, elixirs, suspensions, syrups, wafers, chewing gum and the like. The compounds can be mixed with a suitable pharmaceutical carrier (vehicle) or excipient as understood by practitioners in the art. Non-limiting examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the compounds useful in the methods of the present technology may utilize conventional diluents, carriers, or excipients etc., such as are known in the art can be employed to deliver the compounds. For example, the formulations may comprise one or more of the following: a stabilizer, a surfactant (such as a nonionic, ionic, anionic, cationic, or zwitterionic surfactant), and optionally a salt and/or a buffering agent. The compound may be delivered in the form of a solution or in a reconstituted lyophilized form.

In some embodiments, the stabilizer may, for example, be an amino acid, such as for instance, glycine or an oligosaccharide, such as for example, sucrose, tetralose, lactose or a dextran. Alternatively, the stabilizer may be a sugar alcohol, such as for instance, mannitol, sorbitol, xylitol, or a combination thereof. In some embodiments, the stabilizer or combination of stabilizers constitutes from about 0.1% to about 10% by weight of the formulation, or any percentage in between these two values.

In some embodiments, the surfactant is a nonionic surfactant, such as a polysorbate. Some examples of suitable surfactants include polysorbates (e.g., Tween20, Tween80); a polyethylene glycol or a polyoxyethylene polyoxypropylene glycol, such as Pluronic F-68 at from about 0.001% (w/v) to about 10% (w/v), or any percentage in between these two values.

A salt or buffering agent may be any salt or buffering agent, such as for example, sodium chloride, or sodium/potassium phosphate, respectively. In certain embodiments, the buffering agent maintains the pH of the pharmaceutical composition in the range of about 5.5 to about 7.5, or any pH in between these two values. The salt and/or buffering agent is also useful to maintain the osmolality at a level suitable for administration to a human or an animal. In some embodiments, the salt or buffering agent is present at a roughly isotonic concentration of about 150 mM to about 300 mM.

The formulations of the compounds useful in the methods of the present technology may additionally comprise one or more conventional additives. Some non-limiting examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The mammal can be any mammal, including, for example, farm animals, such as sheep, pigs, cows, and horses; pet animals, such as dogs and cats; laboratory animals, such as rats, mice and rabbits. In some embodiments, the mammal is a human.

IV. Combination Therapy

In some embodiments, the compounds of the present disclosure may be combined with one or more additional therapies for the prevention or treatment of a disease or condition amenable to treatment by inhibition of p97 or modulation of p97, including but not limited to inclusion body myopathy (IBM), Paget's disease of the bone (PDB), frontotemporal dementia (FTD), and amyotrophic lateral sclerosis (ALS). Additional therapeutic agents or active agents include, but are not limited to, alkylating agents, nitrosoureas, antimetabolites, antitumor antibiotics, plant *vinca* alkaloids, and steroid hormones.

The multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

For example, drugs useful in treating inclusion body myopathy (IBM) include, but are not limited to, Arimoclomol, medications that suppress the immune system, such as corticosteroids (e.g., prednisone), immunosuppressants (e.g., methotrexate, azathioprine, cyclophosphamide, and cyclosporine), oxandrolone, Acthar (preparation of ACTH in 16% gelatin formulation), intravenous immune globulin (IVIG), biological agents (e.g., an antibody against myostatin, MYO-029), anti-TNF agents, Rituximab (rituxan), and Alemtuzumab (campath).

Drugs useful in treating Paget's disease of the bone (PDB) include, but are not limited to, Calcitonin (salmon and human), Bisphosphonates (e.g., etidronate, clodronate, aminobisphosphonates, alendronate, risedronate, pamidronate, zoledronate, tiludronate), zoledronic acid, densosumab, calcium, vitamin D, and painkillers (e.g., ibuprofen and paracetamol).

Drugs useful in treating frontotemporal dementia (FTD) include, but are not limited to, Cholinesterase inhibitors, such as donepezil (Aricept®), rivastigmine (Exelon®) and galantamine (Razadyne®), antidepressants (e.g., fluoxetine (Prozac®), sertraline (Zoloft®), paroxetine (Paxil®), fluvoxamine (Luvox®), citalopram (Celexa®), escitalopram (Lexapro®), trazodone (Desyrel®), venlafaxine (Effexor®), duloxetine (Cymbalta®), bupropion (Wellbutrin®), mirtazepine (Remeron®)), antipsychotics (e.g., olanzepine (Zyprexa®), quetiapine (Seroquel® or Ketipinor®), risperidone (Risperdal®), ziprasidone (Geodon®), aripiprazole (Abilify®), paliperidone (INVEGA®)), valproic acid and divalproex sodium (Depacon™, Depakene®, Depakote®, Depakote® ER), carbamazepine (Tegretol®), gabapentin (Neurontin®), and Memantine (Namenda®).

Drugs useful in treating amyotrophic lateral sclerosis (ALS) include, but are not limited to, riluzole (Rilutek), Radicava (edaravone), pain relievers or muscle relaxants such as baclofen (Gablofen, Kemstro, Lioresal) or diazepam (Diastat, Valium).

In some embodiments, the compounds of the present disclosure can be combined with proteosome inhibitors. In another embodiment, the compounds of the present disclosure can be combined with other anti-cancer agents. In some embodiments, the compounds of the present disclosure can be combined with heat shock protein (HSP) inhibitors. In some embodiments, the compounds of the present disclosure can be combined with two or more of proteasome inhibitors, HSP inhibitors, and other anti-cancer agents.

V. Definitions

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Generally, reference to a certain element such as hydrogen or H is meant to include all isotopes of that element. For example, if a group is defined to include hydrogen or H, it also includes deuterium and tritium. Hence, isotopically labeled compounds are within the scope of the present technology. In some embodiments, one or more of the H in Formulae (I), (Ia), (Ib), (Ic), (IIa), (IIb), or (III), is replaced with a deuterium.

In general, "substituted" refers to an organic group (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. The present disclosure is understood to include embodiments where, for instance a "substituted alkyl" optionally contains one or more alkene and/or alkyne. A substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); alkyl; haloalkyl (such as, but not limited to, trifluoroalkyl); hydroxyls; alkoxy, alkenoxy, alkynoxy, aryloxy, aralkyloxy, heterocyclyloxy, and heterocyclylalkoxy groups; aryl groups; heteroaryl groups; cycloalkyl groups; heterocyclyl groups; carbonyls (oxo); carboxyls; esters; urethanes; oximes; carbamates, hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocycle and heteroaryl groups also include rings and fused ring systems in which a bond to a hydrogen atom is replaced with a bond to a carbon atom. Therefore, substituted cycloalkyl, aryl, heterocycle and heteroaryl groups may also be substituted with substituted or unsubstituted alkyl, alkenyl, and alkynyl groups as defined below.

Alkyl groups include straight chain and branched alkyl groups having from 1 to about 20 carbon atoms, and typically from 1 to 12 carbons or, in some embodiments, from 1 to 8, 1 to 6, or 1 to 4 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above. As stated above, the present disclosure is understood to include embodiments where, for instance a "substituted alkyl" optionally contains one or more alkene and/or alkyne.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-di-substituted cyclohexyl groups, which may be substituted with substituents such as those listed above. In some embodiments, a cycloalkyl group has one or more alkene bonds, but is not aromatic.

Bridged cycloalkyl groups are cycloalkyl groups in which two or more hydrogen atoms are replaced by an alkylene bridge, wherein the bridge can contain 2 to 6 carbon atoms if two hydrogen atoms are located on the same carbon atom, or 1 to 5 carbon atoms, if the two hydrogen atoms are located on adjacent carbon atoms, or 2 to 4 carbon atoms if the two hydrogen atoms are located on carbon atoms separated by 1 or 2 carbon atoms. Bridged cycloalkyl groups can be bicyclic, such as, for example bicyclo[2.1.1]hexane, or tricyclic, such as, for example, adamantyl. Representative bridged cycloalkyl groups include bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl groups. Substituted bridged cycloalkyl groups may be substituted one or more times with non-hydrogen and non-carbon groups as defined above. Representative substituted bridged cycloalkyl groups may be mono-substituted or substituted more than once, such as, but not limited to, mono-, di- or tri-substituted adamantyl groups, which may be substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Heterocycle groups include aromatic (also referred to as heteroaryl) and non-aromatic ring compounds containing 3 or more ring members, of which one or more is a heteroatom such as, but not limited to, N, O, S or B. In some embodiments, heterocycle groups include 3 to 20 ring members, whereas other such groups have 3 to 6, 3 to 10, 3 to 12, or 3 to 15 ring members. Heterocycle groups encompass unsaturated, partially saturated and saturated ring systems, such as, for example, imidazolyl, imidazolinyl and imidazolidinyl groups. The phrase "heterocycle group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocycle groups that have other groups, such as alkyl, oxo or halo groups, bonded to one of the ring members. Rather, these are referred to as "substituted heterocycle groups". Heterocycle groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocycle groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, S or B. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The term "amine" (or "amino") as used herein refers to —NHR* and —NR*R* groups, wherein R* are independently hydrogen, or a substituted or unsubstituted alkyl, alkenyl, alkynyl, cycloalkyl, aryl, aralkyl, heterocyclylalkyl or heterocycle group as defined herein. In some embodiments, the amine is $NH_2$, methylamino, dimethylamino, ethylamino, diethylamino, propylamino, isopropylamino, phenylamino, or benzylamino. In some embodiments, the two R* groups together with the nitrogen to which they are attached form an optionally substituted heterocyclic ring. In further embodiments, the optionally substituted ring is an optionally substituted piperazine, optionally substituted piperidine, or optionally substituted pyrrolidine.

The term "amide" refers to a —NR*R*C(O)— group wherein R* each independently refer to a hydrogen, ($C_1$-$C_8$)alkyl, or ($C_3$-$C_6$)aryl or the two R* together with the nitrogen to which they are attached form an optionally substituted heterocyclic ring.

Those of skill in the art will appreciate that compounds of the present technology may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the present technology encompasses any tautomeric, conformational isomeric, optical isomeric and/or geometric isomeric forms of the compounds having one or more of the utilities described herein, as well as mixtures of these various different forms.

As readily understood by one skilled in the art, a wide variety of functional groups and other structures may exhibit tautomerism, and all tautomers of compounds as described herein are within the scope of the present technology.

Stereoisomers of compounds, also known as "optical isomers," include all chiral, diastereomeric, and racemic forms of a structure, unless the specific stereochemistry is expressly indicated. Thus, compounds used in the present technology include enriched or resolved optical isomers at any or all stereogenic atoms as are apparent from the depictions. Both racemic and diastereomeric mixtures, as well as the individual optical isomers can be isolated or synthesized so as to be substantially free of their enantiomeric or diastereomeric partners, and these are all within the scope of the present technology.

By "pharmaceutically acceptable" is meant a material that is not biologically or otherwise undesirable, e.g., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

By "patient" is meant any animal for which treatment is desirable. Patients may be mammals, and typically, as used herein, a patient is a human individual.

The term "pharmaceutically acceptable salt," as used herein, represents salts or zwitterionic forms of the compounds of the present technology which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present technology can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present technology contemplates sodium, potassium, magnesium, and calcium salts of the compounds of the compounds of the present technology and the like.

The term "solvates" is used in its broadest sense. For example, the term solvates includes hydrates formed when a compound of the present technology contains one or more bound water molecules.

The compound named "3-(4-((2-(cyclohex-2-en-1-yl-thio)-1-(pyridin-3-yl)-1H-imidazol-5-yl)methoxy)-2-methylphenyl)prop-2-yn-1-yl (2-(4-isopropylpiperazin-1-yl) ethyl)carbamate" has the structure of:

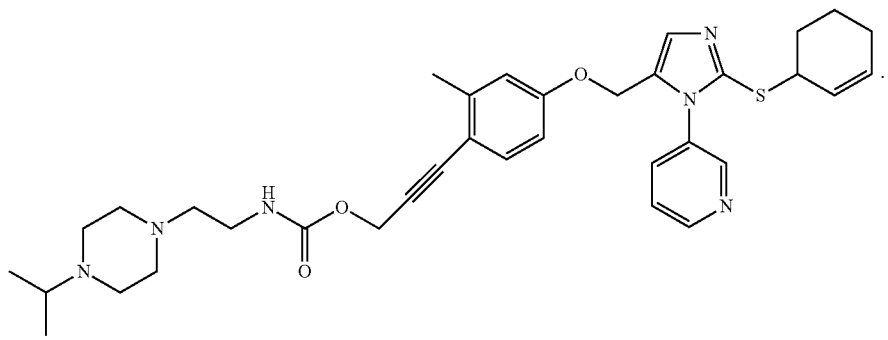 [SMILES: Cc1cc(OCc2cnc(SC3C=CCCC3)n2-c2cccnc2)ccc1C#CCOC(=O)NCCN1CCN(C(C)C)CC1]

Certain compounds within the scope of the disclosure are derivatives referred to as prodrugs. The expression "prodrug" denotes a derivative of a known direct acting drug, e.g. esters and amides, which derivative has enhanced delivery characteristics and therapeutic value as compared to the drug, and is transformed into the active drug by an enzymatic or chemical process; see Notari, R. E., "Theory and Practice of Prodrug Kinetics," Methods in Enzymology 112: 309-23 (1985); Bodor, N., "Novel Approaches in Prodrug Design," Drugs of the Future, 6: 165-82 (1981); and Bundgaard, H., "Design of Prodrugs: Bioreversible-Derivatives for Various Functional Groups and Chemical Entities," in DESIGN OF PRODRUGS (H. Bundgaard, ed.), Elsevier (1985), Goodman and Gilmans, THE PHARMACOLOGICAL BASIS OF THERAPEUTICS, 8th ed., McGraw-Hill (1992). In some embodiments, the "prodrug" is a compound that generally converts to an active compound of the present disclosure within a physiological environment (e.g., stomach, colon, blood). Pro-drugs include esters, carbonates, carbamates, oximes of active alcohols (and/or acids for esters), amides, carbamates, ureas, oximes, Mannich bases, imines of amines (and/or acids for amides), carbondithianes of active thiols, conjugates of reactive species such as a,b-unsaturated carbonyl derivatives. The selection and synthesis of prodrugs include strategies such as those in: Karaman, R., "Prodrugs design based on inter- and intramolecular chemical processes," Chem. Biol. Drug Des., 82: 643-668 (2013); Huttunen et al., "Prodrugs—from serendipity to rational design," Pharmacol. Rev., 63, 750-771 (2011); Blencowe et al., "Self-immolative linkers in polymeric delivery systems," Polym. Chem., 2: 773-790 (2011); Arpicco et al., "Anticancer prodrugs: An overview of major strategies and recent developments," Curr. Top. Med. Chem. (Sharjah, United Arab Emirates), 11: 2346-2381 (2011); Tietze et al., "Antibody-directed enzyme prodrug therapy: A promising approach for a selective treatment of cancer based on prodrugs and monoclonal antibodies" Chem. Biol. Drug Des., 74: 205-211 (2009); Simplicio et al., "Prodrugs for amines," Molecules, 13: 519-547 (2008); Rautio et al., "Prodrugs: Design and clinical applications," Nat. Rev. Drug Discovery, 7: 255-270 (2008); Lee et al., "Pro-drug and Antedrug: Two Diametrical Approaches in Designing Safer Drugs," Arch. Pharm. Res., 25: 111-136 (2002); and Lee, Chem. Biol. Drug Des., 82: 643-668 (2013).

Generally, reference to a certain moiety capable of being protected (such as hydroxy, amine, carbonyl, etc.) includes the protected groups in some embodiments of the disclosure. For example, in some embodiments, an —OH moiety as included herein also includes —OP, where P is a protecting group. Protecting groups, as referred to herein may be selected by one of ordinary skill in the art, and include the groups and strategies set forth in the art, for example, those such as described in R. Larock, Comprehensive Organic Transformations, VCH Publishers (1989); T. W. Greene and P. G. M. Wuts, *Greene's protective groups in organic synthesis*, John Wiley & Sons (2006); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Unless defined otherwise, all technical and scientific terms used herein have the same meaning as commonly understood by one of ordinary skill in the art to which this present technology belongs. Although any methods and materials similar or equivalent to those described herein can also be used in the practice or testing of the present technology, representative illustrative methods and materials are now described.

Where a range of values is provided, it is understood that each intervening value, to the tenth of the unit of the lower limit unless the context clearly dictates otherwise, between the upper and lower limit of that range and any other stated or intervening value in that stated range, is encompassed within the present technology. The upper and lower limits of these smaller ranges may independently be included in the smaller ranges and are also encompassed within the present technology, subject to any specifically excluded limit in the stated range. Where the stated range includes one or both of the limits, ranges excluding either or both of those included limits are also included in the present technology.

This disclosure is not limited to particular embodiments described, as such may, of course, vary. It is also to be understood that the terminology used herein is for the purpose of describing particular embodiments only, and is not intended to be limiting, since the scope of the present technology will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present technology. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present technology is not entitled to antedate such publication by virtue of prior invention. Further, the dates of publication provided may be different from the actual publication dates which may need to be independently confirmed.

VI. WORKING EXAMPLES

The present technology is further illustrated by the following examples, which should not be construed as limiting in any way.

General information. All non-aqueous reactions were carried out under a nitrogen atmosphere in oven- or flame-dried glassware unless otherwise noted. Anhydrous tetrahydrofuran and diethyl ether were distilled from sodium benzophenone ketyl; anhydrous dichloromethane and toluene were distilled from $CaH_2$; alternatively, the same solvents were obtained from a solvent purification system using alumina columns. All other solvents and reagents were used as obtained from commercial sources without further purification unless noted. Reactions were monitored via TLC using 250 μm pre-coated silica gel 60 $F_{254}$ plates, which were visualized with 254 nm and/or 365 nm UV light and by staining with $KMnO_4$ (1.5 g $KMnO_4$, 10 g $K_2CO_3$, and 1.25 mL 10% NaOH in 200 mL water), cerium molybdate (0.5 g $Ce(NH_4)_2(NO_3)_6$, 12 g $(NH_4)_6Mo_7O_{24} \cdot 4H_2O$, and 28 mL conc. $H_2SO_4$ in 235 mL water), or vanillin (6 g vanillin and 1.5 mL conc. H2SO4 in 100 mL EtOH). Flash chromatography was performed with SiliCycle silica gel 60 (230-400 mesh) or with ISCO MPLC. $^1$H and $^{13}$C NMR spectra were recorded on Bruker Avance 300, 400, or 500 MHz spectrometers, using the residual solvent as an internal standard. IR spectra were obtained on a Smiths IdentifyIR or PerkinElmer Spectrum 100. HRMS data were obtained on a Thermo Scientific Exactive HRMS coupled to a Thermo Scientific Accela HPLC system using a 2.1×50 mm 3.5 μm Waters XTerra C18 column eluting with MeCN/$H_2O$ containing 0.1% formic acid. Purity of compounds was assessed using the same HPLC system with either the PDA or an Agilent 385 ELSD. All final screening samples passed QC based on >95% purity by LC/MS/ELSD analysis.

General Synthetic Methods

The compounds of the present disclosure can be prepared using the following general methods and procedures. The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley, and Sons, 1991), *Rodd's Chemistry of Carbon Compounds*, Volumes 1-5, and Supplementals (Elsevier Science Publishers, 1989), *Organic Reactions*, Volumes 1-40 (John Wiley, and Sons, 1991), *March's Advanced Organic Chemistry*, (John Wiley, and Sons, 5$^{th}$ Edition, 2001), and *Larock's Comprehensive Organic Transformations* (VCH Publishers Inc., 1989).

More specifically, compounds provided herein can be synthesized as shown in the following Examples, and following adaptations of the methods described therein and/or methods known to a skilled artisan and/or by using different commercially available starting materials.

Example 1. Ethyl 2-mercapto-1-(pyridin-3-yl)-1H-imidazole-5-carboxylate

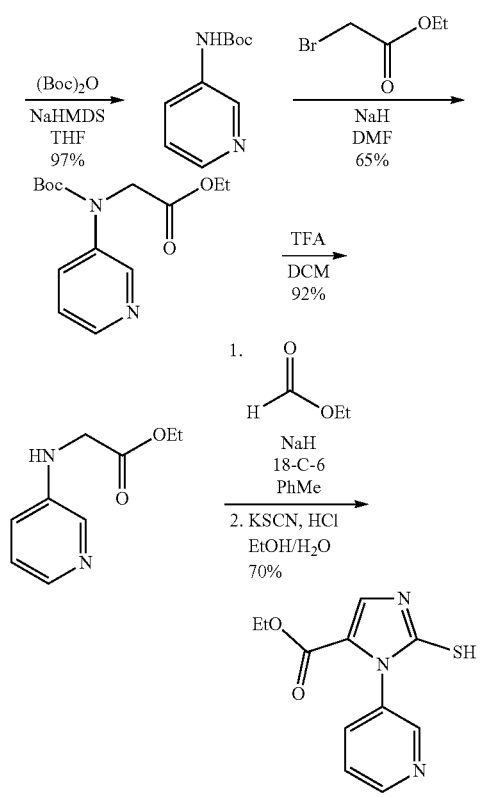

A. tert-Butyl pyridin-3-ylcarbamate

To a flame-dried 500 mL round-bottom flask purged with N2 was added 3-aminopyridine (10.0 g, 105 mmol) and THF (109 mL). NaHMDS (210 mL, 1.0 M solution in THF, 210 mmol) was added dropwise over 1 h and the resulting red solution was stirred for 30 min. Di-tert-butyl dicarbonate (24.3 mL, 105 mmol) was added dropwise over 2 min. After 19 h, the dark red solution was concentrated to 100 mL and $H_2O$ (1.0 L) was added. The mixture was extracted with EtOAc (3×500 mL). The combined organic layers were washed with brine, dried ($MgSO_4$) and concentrated to give product (19.9 g, 102 mmol, 97%) as a brown solid: $^1$H NMR (CDCl$_3$, 400 MHz) 8.46 (d, J=2.5 Hz, 1H), 8.31 (dd, J=4.7, 1.4 Hz, 1H), 8.00 (d, J=6.7 Hz, 1H), 7.26 (dd, J=8.4, 4.7 Hz, 1H), 6.65-6.66 (m, 1H) 1.55 (s, 9H).

B. Ethyl N-(tert-butoxycarbonyl)-N-(pyridin-3-yl)glycinate

A solution of tert-butyl pyridin-3-ylcarbamate (1.00 g, 4.89 mmol) in dry DMF (17.7 mL) under N2 was treated with NaH (60% dispersion, 295 mg, 7.39 mmol) at 0° C. After 10 min, the solution was warmed to room temperature. After 30 min, the solution was cooled to 0° C. and ethyl bromoacetate (0.61 mL, 5.39 mmol) was added. After 10 min, the solution was warmed to room temperature and allowed to stir for 3 h. The reaction mixture was then quenched with H$_2$O (10 mL) and extracted with EtOAc (100 mL). The organic layer was washed sequentially with H$_2$O (3×100 mL) and brine, dried (MgSO$_4$), and concentrated. The crude material was purified by chromatography on SiO$_2$ (1:1 hexanes/EtOAc) to give product (1.07 g, 3.19 mmol, 65%) as a yellow oil: $^1$H NMR (CDCl$_3$, 400 MHz) 8.58 (d, J=2.0 Hz, 1H), 8.47 (dd, J=4.8, 1.5 Hz, 1H), 7.69 (s, 1H), 7.29-7.31 (m, 1H), 4.31 (s, 2H), 4.25 (q, J=7.1 Hz, 2H), 1.46 (s, 9H) 1.29-1.33 (m, 3H).

C. Ethyl pyridin-3-ylglycinate

A solution of ethyl N-(tert-butoxycarbonyl)-N-(pyridin-3-yl)glycinate (1.07 g, 3.81 mmol) in CH$_2$Cl$_2$ (14.5 mL) was cooled to 0° C. and treated with TFA (3.4 mL, 45.8 mmol). After 10 min, the solution was warmed to room temperature and allowed to stir for 4 h. The reaction mixture was then concentrated, dissolved in EtOAc (100 mL) and washed with satd. NaHCO$_3$ (3×75 mL). The aqueous layer was re-extracted with EtOAc (100 mL) and the combined organic layers were washed with brine, dried (MgSO$_4$) and concentrated to give product (633 mg, 3.52 mmol, 92%) as a yellow-brown oil: $^1$H NMR (CDCl$_3$, 400 MHz) 8.07 (d, J=2.8 Hz, 1H), 8.03 (dd, J=4.7, 1.2 Hz, 1H), 7.12 (dd, J=8.3, 4.7 Hz, 1H), 6.89 (ddd, J=8.3, 2.9, 1.3 Hz, 1H), 4.41 (s, 1H), 4.28 (q, J=7.1 Hz, 2H), 3.93 (s, 2H) 1.32 (t, J=7.1 Hz, 3H).

D. Ethyl 2-mercapto-1-(pyridin-3-yl)-1H-imidazole-5-carboxylate

A solution of ethyl pyridin-3-ylglycinate (10.2 g, 51.0 mmol), 18-crown-6 (1.37 g, 5.15 mmol), and ethyl formate (8.2 mL, 102 mmol) in dry toluene (40 mL) was cooled to 0° C. and slowly treated with NaH (60% dispersion, 5.39 g, 135 mmol). The resultant mixture was gradually warmed to room temperature, heated at 60° C. for 20 min, and cooled back down to room temperature. The reaction mixture was then quenched with EtOH (4.0 mL) and H$_2$O (51 mL) and charged with potassium thiocyanate (24.8 g, 255 mmol). The mixture was then acidified using conc. HCl (33.5 mL) and stirred at reflux for 1.5 h. The reaction mixture was then cooled to room temperature and extracted with EtOAc (3×500 mL). The combined organic layers were dried with minimal Na$_2$SO$_4$ and concentrated directly onto SiO$_2$. Purification by flash chromatography on SiO$_2$ (9:1 EtOAc/hexanes) gave product (8.88 g, 35.6 mmol, 70%) as an orange solid: $^1$H NMR (DMSO-d$_6$, 400 MHz) 13.26 (s, 1H), 8.69 (d, J=19.2 Hz, 2H), 8.03 (d, J=2.9 Hz, 1H), 7.99 (ddd, J=8.1, 2.3, 1.5 Hz, 1H), 7.67-7.70 (m, 1H), 4.07 (q, J=7.1 Hz, 2H) 1.08 (t, J=7.1 Hz, 3H).

Example 2. 3-(5-(((tert-Butyldimethylsilyl)oxy)methyl)-2-(cyclopentylthio)-4-iodo-1H-imidazol-1-yl)pyridine (17)

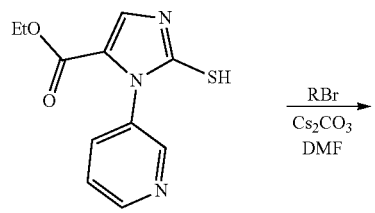

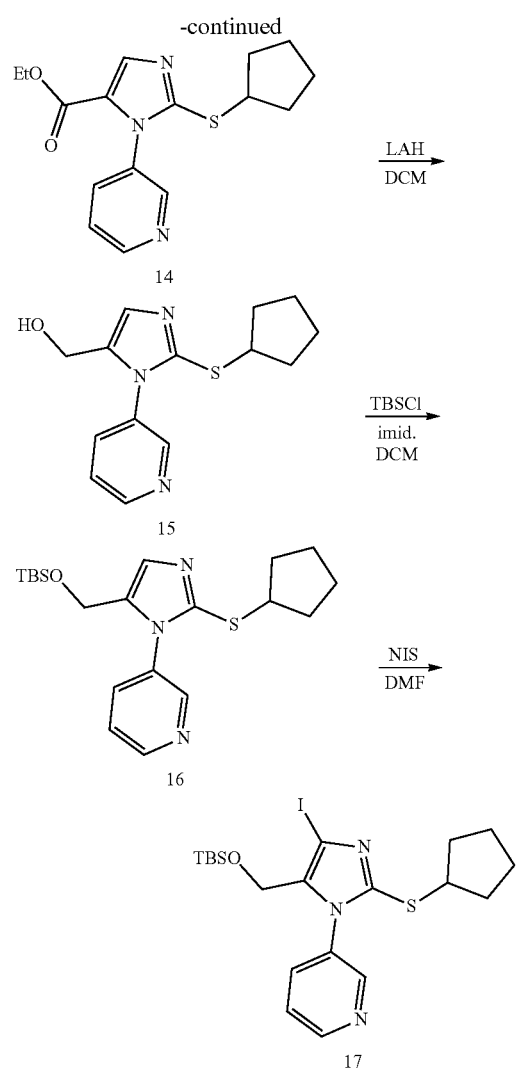

A. Ethyl 2-(cyclopentylthio)-1-(pyridin-3-yl)-1H-imidazole-5-carboxylate (14)

To a solution of ethyl 2-mercapto-1-(pyridin-3-yl)-1H-imidazole-5-carboxylate (0.25 g, 1.0 mmol) in DMF (3.0 mL) was added bromo-cyclopentane (0.12 mL, 1.1 mmol) followed by Cs$_2$CO$_3$ (0.689 g, 2.11 mmol) at room temperature. After 22 h, the reaction mixture was extracted with EtOAc, washed with brine, dried, (Na$_2$SO$_4$), filtered and concentrated. The residue was purified by chromatography on SiO$_2$ (ISCO-Rf, 0-100% EtOAc/hexanes) to give product (14, 0.238 g, 75%) as an off-white solid. $^1$H NMR (CDCl$_3$, 500 MHz) 8.65 (d, J=1.0, 4.6 Hz, 1H), 8.47 (d, J=2.2 Hz, 1H), 7.79 (s, 1H), 7.59-7.56 (m, 1H), 7.38 (dd, J=4.8, 7.9 Hz, 1H), 4.07 (q, J=7.1 Hz, 2H), 3.94 (pent, J=6.7 Hz, 1H), 2.13-2.06 (m, 2H), 1.64-1.56 (m, 2H), 1.53-1.49 (m, 4H), 1.12 (t, J=7.2 Hz, 3H); $^{13}$C NMR (CDCl$_3$, 125 MHz) 158.9, 151.2, 149.9, 148.3, 137.8, 134.9, 132.9, 125.3, 123.3, 60.3, 45.8, 33.5, 24.4, 13.9; HRMS (LCMS ESI+) m/z calcd for C$_{16}$H$_{20}$N$_3$O$_2$S [M+H] 318.1271, found 318.1268.

B. (2-(Cyclopentylthio)-1-(pyridin-3-yl)-1H-imidazol-5-yl)methanol (15)

A solution of LAH (0.330 mL, 4.0 M Et$_2$O) in dry Et$_2$O (4.0 mL) was cooled to −40° C. and treated with ethyl 2-(cyclopentylthio)-1-(pyridin-3-yl)-1H-imidazole-5-carboxylate (14, 0.238 g, 0.750 mmol) in CH$_2$Cl$_2$ 4.0 mL). After 10 min, the solution was warmed to 0° C. and quenched with H$_2$O (0.5 mL), NaOH (0.5 M, 0.5 mL), followed by H$_2$O (0.5 mL). The mixture was treated with Na$_2$SO$_4$, filtered and concentrated to give product (15, 0.189 g, 92%) as a light yellow oil that solidified upon standing and was used without further purification. IR (neat) 3219, 2954, 2865, 1482, 1429, 1287, 1207, 1192, 1023, 1001, 813, 707 cm$^{-1}$; $^1$H NMR (CDCl$_3$, 500 MHz) 8.61 (dd, J=1.5, 4.8 Hz, 1H), 8.54 (d, J=2.0 Hz, 1H), 7.76-7.74 (m, 1H), 7.45-7.42 (m, 1H), 7.01 (s, 1H), 4.38 (s, 2H), 4.20 (br s, 1H), 3.69 (pent, J=6.2 Hz, 1H), 2.00-1.93 (m, 2H), 1.3-1.51 (m, 2H), 1.48-1.45 (m, 4H); $^{13}$C NMR (CDCl$_3$, 125 MHz) 149.8, 1486, 144.7, 135.7, 134.2, 132.6, 129.1, 123.7, 53.7, 46.9, 33.5, 24.4; HRMS (LCMS ESI+) m/z calcd for C$_{14}$H$_{18}$N$_3$OS [M+H] 276.1165, found 276.1170.

C. 3-(5-(((tert-Butyldimethylsilyl)oxy)methyl)-2-(cyclopentylthio)-1H-imidazol-1-yl)pyridine (16)

To a solution of (2-(cyclopentylthio)-1-(pyridin-3-yl)-1H-imidazol-5-yl)methanol (15, 0.189 g, 0.686 mmol) in CH$_2$Cl$_2$ (2.0 mL) was added TBSCl (0.121 g, 0.80 mmol) followed by imidazole (0.053 g, 0.78 mmol) followed by TEA (0.050 mL, 0.36 mmol) at room temperature. After 17 h, the solution was extracted with CH$_2$Cl$_2$, washed with brine, dried (Na$_2$SO$_4$), filtered and concentrated. The residual oil was purified by chromatography on SiO$_2$ (0-100% EtOAc/hexanes) to give product (16, 0.253 g, 95%) as a white solid. M.p. 71-72° C.; IR (neat) 2952, 2925, 1477, 1339, 1384, 1289, 1252, 1230, 1194, 1057, 1040, 982, 838, 817, 775, 712, 669 cm$^{-1}$; $^1$H NMR (CDCl$_3$, 500 MHz) 8.66 (dd, J=1.4, 4.8 Hz, 1H), 8.57 (d, J=2.1 Hz, 1H), 7.67-7.65 (m, 1H), 7.40 (dd, J=4.6, 7.8 Hz, 1H), 7.07 (s, 1H), 4.37 (s, 2H), 3.75 (pent, J=6.0 Hz, 1H), 2.02-1.96 (m, 2H), 1.64-1.62 (m, 2H), 1.54-1.48 (m, 4H), 0.75 (s, 9H), 0.13 (s, 6H); $^{13}$C NMR (CDCl$_3$, 125 MHz) 149.8, 148.8, 144.6, 135.5, 133.5, 132.7, 129.1, 123.4, 54.7, 46.7, 33.5, 25.6, 24.4, 18.0, −5.7; HRMS (LCMS ESI+) m/z calcd for C$_{20}$H$_{32}$N$_3$OSSi [M+H] 390.2030, found 390.2059.

D. 3-(5-(((tert-Butyldimethylsilyl)oxy)methyl)-2-(cyclopentylthio)-4-iodo-1H-imidazol-1-yl)pyridine (17)

A solution of 3-(5-(((tert-butyldimethylsilyl)oxy)methyl)-2-(cyclopentylthio)-1H-imidazol-1-yl)pyridine (16, 1.99 g, 5.10 mmol) in dry DMF (20.0 mL) was wrapped with foil and cooled to 0° C. To this solution was added N-iodosuccinimide (2.29 g, 9.97 mmol). After 1 h, the solution was warmed to room temperature. After 2 d, the solution was extracted with EtOAc, washed with satd. sodium thiosulfate, brine, dried (Na$_2$SO$_4$), filtered and concentrated. The residue was purified by chromatography on SiO$_2$ (ISCO-Rf, 0-100% EtOAc/hexanes) to give product as a yellow solid (17, 1.62 g, 62%). $^1$H NMR (CDCl$_3$, 500 MHz) 8.71 (d, J=4.0 Hz, 1H), 8.59 (d, J=2.0 Hz, 1H), 7.70-7.68 (m, 1H), 7.44 (dd, J=4.8, 8.0 Hz, 1H), 4.38 (s, 2H), 3.83 (pent, J=6.6 Hz, 1H), 2.08-2.02 (m, 2H), 1.66-1.61 (m, 2H), 1.59-1.49 (m, 4H), 0.80 (s, 9H), −0.02 (s, 6H); HRMS (LCMS ESI+) m/z calcd for C$_{20}$H$_{31}$N$_3$OSSiI [M+H] 516.0996, found 516.0994.

Example 3. 3-(4-((2-(Cyclopentylthio)-4-(3-hydroxyprop-1-yn-1-yl)-1-(pyridin-3-yl)-1H-imidazol-5-yl)methoxy)-2-methylphenyl)prop-2-yn-1-ol

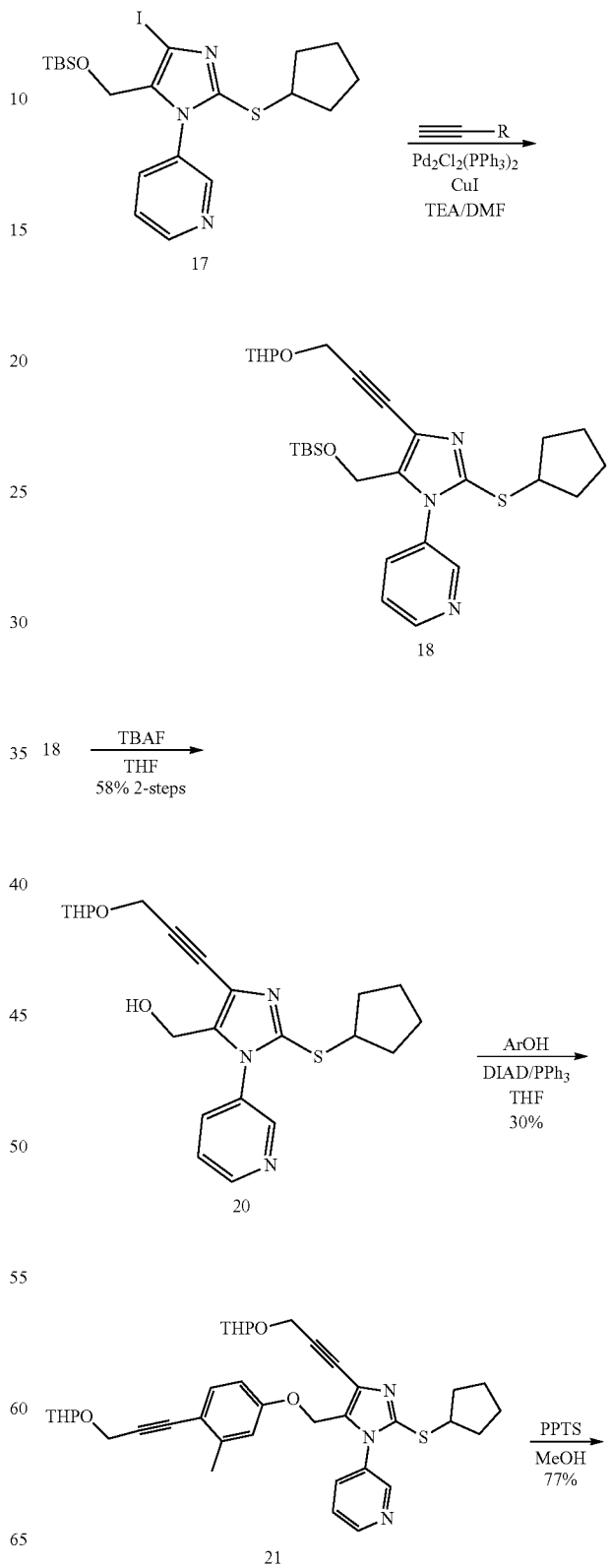

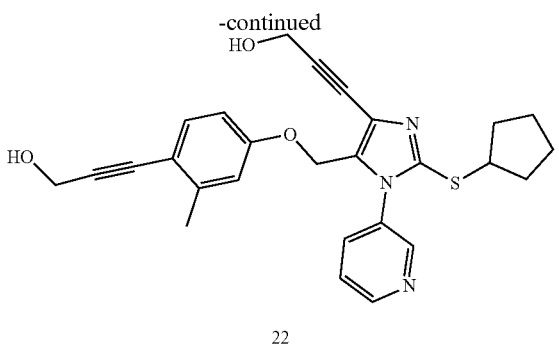

22

A. 3-(5-(((tert-Butyldimethylsilyl)oxy)methyl)-2-(cyclopentylthio)-4-iodo-1H-imidazol-1-yl)pyridine (17)

A solution of 3-(5-(((tert-butyldimethylsilyl)oxy)methyl)-2-(cyclopentylthio)-1H-imidazol-1-yl)pyridine (16, 1.99 g, 5.10 mmol) in dry DMF (20.0 mL) was wrapped with foil and cooled to 0° C. To this solution was added N-iodosuccinimide (2.29 g, 9.97 mmol). After 1 h, the solution was warmed to room temperature. After 2 d, the solution was extracted with EtOAc, washed with satd. sodium thiosulfate, brine, dried ($Na_2SO_4$), filtered and concentrated. The residue was purified by chromatography on $SiO_2$ (ISCO-Rf, 0-100% EtOAc/hexanes) to give product as a yellow solid (17, 1.62 g, 62%). $^1$H NMR (CDCl$_3$, 500 MHz) 8.71 (d, J=4.0 Hz, 1H), 8.59 (d, J=2.0 Hz, 1H), 7.70-7.68 (m, 1H), 7.44 (dd, J=4.8, 8.0 Hz, 1H), 4.38 (s, 2H), 3.83 (pent, J=6.6 Hz, 1H), 2.08-2.02 (m, 2H), 1.66-1.61 (m, 2H), 1.59-1.49 (m, 4H), 0.80 (s, 9H), −0.02 (s, 6H); HRMS (LCMS ESI+) m/z calcd for $C_{20}H_{31}N_3OSSiI$ [M+H] 516.0996, found 516.0994.

B. 3-(5-(((tert-Butyldimethylsilyl)oxy)methyl)-2-(cyclopentylthio)-4-(3-((tetrahydro-2H-pyran-2-yl)oxy)prop-1-yn-1-yl)-1H-imidazol-1-yl)pyridine (18)

To a solution of 3-(5-(((tert-Butyldimethylsilyl)oxy)methyl)-2-(cyclopentylthio)-4-iodo-1H-imidazol-1-yl)pyridine (17, 0.120 g, 0.23 mmol) in degassed DMF (1.0 mL) was added 2-(prop-2-yn-1-yloxy)tetrahydro-2H-pyran (0.210 g, 1.49 mmol) in DMF (0.5 mL). The solution was degassed and PdCl$_2$(PPh$_3$)$_2$ (0.031 g, 0.044 mmol) and CuI (0.009 g, 0.046 mmol) was added. The solution was further degassed and TEA (0.30 mL, 2.11 mmol) was added. The solution was degassed (5 min) and the reaction vial was sealed and submerged into preheated oil bath at 90° C. and kept at this temperature overnight. The reaction mixture was cooled to room temperature, extracted with EtOAc, washed with brine (2×), dried ($Na_2SO_4$), filtered and concentrated. The residue was purified by chromatography on $SiO_2$ (ISCO-Rf, 0-100% EtOAc/hexanes) to give semi-pure product (18, 0.144 g, >theoretical) as an orange oil that was used without further purification. HRMS (LCMS ESI+) m/z calcd for $C_{28}H_{42}N_3O_3SSi$ [M+H] 528.2711, found 528.2713.

C. (2-(Cyclopentylthio)-1-(pyridin-3-yl)-4-(3-((tetrahydro-2H-pyran-2-yl)oxy)prop-1-yn-1-yl)-1H-imidazol-5-yl)methanol (20)

A solution of 3-(5-(((tert-butyldimethylsilyl)oxy)methyl)-2-(cyclopentylthio)-4-(3-((tetrahydro-2H-pyran-2-yl)oxy)prop-1-yn-1-yl)-1H-imidazol-1-yl)pyridine (18, 0.144 g, crude, theoretical 0.23 mmol) in THF (2.0 mL) was cooled to 0° C. and treated with TBAF (0.25 mL, 1M THF). After 1 h, the solution was extracted with EtOAc, washed with brine, dried ($Na_2SO_4$), filtered and concentrated. The residue was purified by chromatography on $SiO_2$ (ISCO-Rf, 0-100% EtOAc/hexanes) to give product (20, 0.055 g, 58% 2-steps) as a light orange oil. IR (neat) 3266, 2943, 2866, 1483, 1429, 1385, 1283, 1200, 1117, 1020, 901, 870, 814, 728, 707 cm$^{-1}$; $^1$H NMR (CDCl$_3$, 500 MHz) 8.68 (d, J=2.5 Hz, 1H), 8.59 (s, 1H), 7.76 (d, J=8.1 Hz, 1H), 7.45 (dd, J=4.5, 8.0 Hz, 1H), 4.87 (t, J=3.3 Hz, 1H), 4.47 (d, J=7.5 Hz, 2H), 3.91-3.83 (m, 2H), 3.54-3.52 (m, 1H), 2.92 (br s, 1H), 2.09-2.06 (m, 2H), 1.82-1.49 (m, 14H); $^{13}$C NMR (CDCl$_3$, 125 MHz) 150.4, 148.7, 145.6, 137.7, 135.7, 132.3, 124.2, 124.0, 97.1, 88.7, 78.3, 62.2, 55.1, 53.4, 46.6, 33.8, 30.4, 25.5, 24.7, 19.2; HRMS (LCMS ESI+) m/z calcd for $C_{22}H_{28}N_3O_3S$ [M+H] 414.1846, found 414.1843.

D. 3-(2-(Cyclopentylthio)-5-((3-methyl-4-(3-((tetrahydro-2H-pyran-2-yl)oxy)prop-1-yn-1-yl)phenoxy)methyl)-4-(3-((tetrahydro-2H-pyran-2-yl)oxy)prop-1-yn-1-yl)-1H-imidazol-1-yl)pyridine (21)

To a solution of (2-(cyclopentylthio)-1-(pyridin-3-yl)-4-(3-((tetrahydro-2H-pyran-2-yl)oxy)prop-1-yn-1-yl)-1H-imidazol-5-yl)methanol (20, 0.034 g, 0.082 mmol), PPh$_3$ (0.042 g, 0.15 mmol), 3-methyl-4-(3-((tetrahydro-2H-pyran-2-yl)oxy)prop-1-yn-1-yl)phenol (0.042 g, 0.17 mmol) in THF (0.4 mL) was added DIAD (0.040 mL, 0.20 mmol) at room temperature. After 2 d, the solution was extracted with EtOAc, washed with satd. NaHCO$_3$, brine, dried (Na$_2$SO$_4$), filtered and concentrated. The residue was purified by chromatography on SiO$_2$ (ISCO-Rf, 0-100% EtOAc/hexanes) to give product (21, 0.016 g, 30%) as an orange oil. IR (neat) 2941, 2867, 1717, 1603, 1495, 1483, 1385, 1287, 1228, 1116, 1055, 1020, 901, 869, 814, 729, 708 cm$^{-1}$; $^1$H NMR (CDCl$_3$, 600 MHz) 8.69 (br s, 1H), 8.59 (br s, 1H), 7.66 (d, J=7.8 Hz, 1H), 7.42 (s, 1H), 7.28 (d, J=8.4 Hz, 1H), 6.68 (d, J=1.8 Hz, 1H), 6.59 (dd, J=2.4, 9.0 Hz, 1H), 4.91 (t, J=3.6 Hz, 1H), 4.88 (t, J=3.0 Hz, 1H), 4.85 (s, 2H), 4.56-4.46 (m, overlapping signals, 4H), 3.94 (pent, J=7.2 Hz, 1H), 3.88-3.83 (m, 2H), 3.57-3.50 (m, 2H), 2.36 (s, 3H), 2.14-2.11 (m, 2H), 1.85-1.75 (m, 2H), 1.71-1.52 (m, 16H); $^{13}$C NMR (CDCl$_3$, 151 MHz) 157.3, 150.6, 148.7, 146.6, 142.3, 135.4, 133.5, 132.8, 125.8, 115.7, 115.6, 112.1, 96.9, 96.6, 89.3, 87.7, 84.3, 77.9, 68.0, 62.1, 58.6, 54.8, 54.7, 46.2, 33.7, 30.3, 30.2, 25.4, 25.3, 24.5, 21.9, 20.9, 19.1, 19.0; HRMS (LCMS ESI+) m/z calcd for $C_{37}H_{44}N_3O_5S$ [M+H] 642.2996, found 642.2998.

E. 3-(4-((2-(Cyclopentylthio)-4-(3-hydroxyprop-1-yn-1-yl)-1-(pyridin-3-yl)-1H-imidazol-5-yl)methoxy)-2-methylphenyl)prop-2-yn-1-ol (22)

A solution of 3-(2-(cyclopentylthio)-5-((3-methyl-4-(3-((tetrahydro-2H-pyran-2-yl)oxy)prop-1-yn-1-yl)phenoxy)methyl)-4-(3-((tetrahydro-2H-pyran-2-yl)oxy)prop-1-yn-1-yl)-1H-imidazol-1-yl)pyridine (21, 0.060 g, 0.093 mmol) in MeOH (1.0 mL) was treated with PPTS (0.023 g, 0.092 mmol) at room temperature. The reaction mixture was heated at 40° C. After 2 h, the solution was extracted with CH$_2$Cl$_2$, washed with satd. NaHCO$_3$, brine, dried (Na$_2$SO$_4$), filtered and concentrated. The residue was purified by chromatography on SiO$_2$ (ISCO-Rf, 0-100% EtOAc/hexanes) to give product (22, 0.034 g, 77%) as a light yellow oil. IR (neat) 3215, 2942, 2859, 1602, 1483, 1431, 1380, 1289, 1227, 1165, 1025, 994, 958, 820, 707 cm$^1$; $^1$H NMR (CDCl₃, 600 MHz) 8.68 (d, J=3.6 Hz, 1H), 8.61 (s, 1H), 7.66 (d, J=7.8 Hz, 1H), 7.42 (dd, J=4.8, 7.2 Hz, 1H), 7.15 (d, J=8.4 Hz, 1H), 6.64 (d, J=1.8 Hz, 1H), 6.54 (dd, J=1.8, 8.4 Hz, 1H), 4.84 (s, 2H), 4.56 (s, 2H), 4.49 (s, 2H), 3.91 (pent, J=6.6 Hz, 1H), 3.83 (br s, 1H), 3.20 (br s, 1H), 2.28 (s, 3H), 2.10-2.06 (m, 2H), 1.64-1.56 (m, 2H), 1.53-1.49 (m, 4H); ¹³C NMR (CDCl₃, 151 MHz) 157.1, 150.4, 148.6, 146.7, 142.1, 135.5, 133.3, 132.5, 131.9, 125.6, 123.9, 115.6, 115.6, 112.0, 92.4, 90.4, 83.8, 58.4, 51.4, 51.3, 46.2, 33.6, 24.5, 20.8; HRMS (LCMS ESI+) m/z calcd for C₂₇H₂₈N₃O₃S [M+H] 474.1846, found 474.1843; ELS purity (99.3%).

Example 4. N-(3-(4-((2-(cyclohex-2-en-1-ylthio)-1-(pyridin-3-yl)-1H-imidazol-5-yl)methoxy)-2-methylphenyl)prop-2-yn-1-yl)-1-methylpiperidin-4-amine (7)

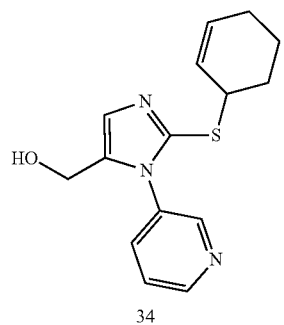

34

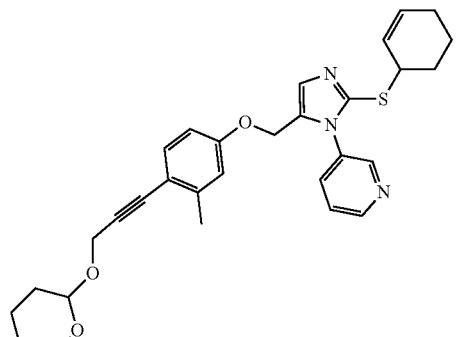

35

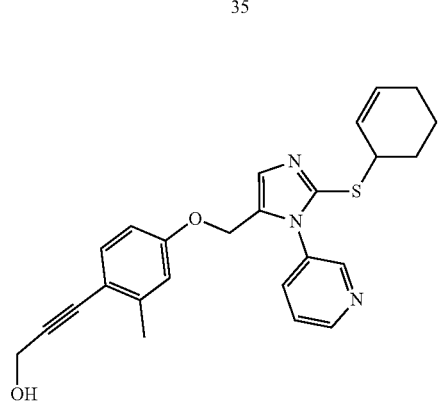

36

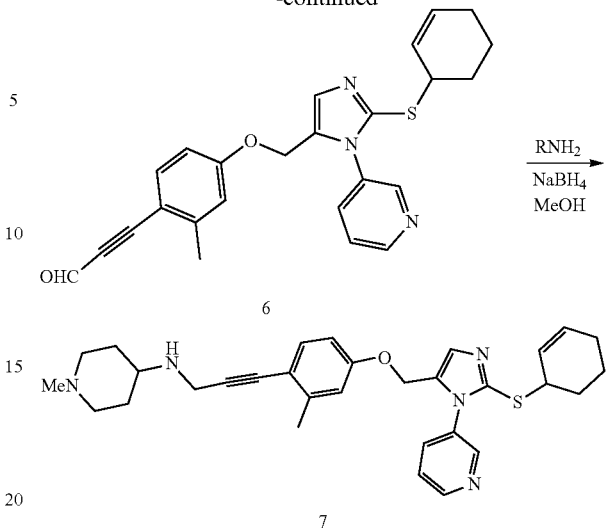

A. 3-(2-(Cyclohex-2-en-1-ylthio)-5-((3-methyl-4-(3-((tetrahydro-2H-pyran-2-yl)oxy)prop-1-yn-1-yl)phenoxy)methyl)-1H-imidazol-1-yl)pyridine (35)

A solution of alcohol (34, 0.036 g, 0.13 mmol), 3-methyl-4-(3-((tetrahydro-2H-pyran-2-yl)oxy)prop-1-yn-1-yl)phenol (0.033 g, 0.13 mmol), PPh₃ (0.047 g, 0.18 mmol) in dry THF (2.0 mL) was degassed with N2 (10 min). To this solution was added DIAD (0.030 mL, 0.15 mmol) and the solution was stirred at room temperature overnight. The reaction mixture was concentrated. The residue was purified by chromatography on SiO₂ (ISCO-Rf, 0-100% EtOAc/hexanes) to give product (35, 0.020 g, 31%) as a colorless oil: ¹H NMR (CDCl₃, 500 MHz) 8.67-8.62 (m, 2H), 7.70 (d, J=7.5 Hz, 1H), 7.39 (dd, J=5.0, 7.5 Hz, 1H), 7.30-7.26 (m, 2H), 6.61 (s, 1H), 6.55 (d, J=8.5 Hz, 1H), 5.82-5.80 (m, 1H), 5.69-5.67 (m, 1H), 4.90 (br s, 1H), 4.74 (app q, J=12.5 Hz, 2H), 4.49 (app q, J=15.5 Hz, 2H), 4.33 (br s, 1H), 3.87 (app t, J=9.5 Hz, 1H), 3.55 (app t, J=5.0 Hz, 1H), 2.35 (s, 3H), 1.99-1.88 (m, 4H), 1.85-1.83 (m, 2H), 1.66-1.54 (m, 8H), 1.26-1.17 (m, 4H); ¹³C NMR (CDCl₃, 125 MHz) 157.6, 150.2, 148.8, 145.5, 142.3, 135.4, 133.5, 132.2, 131.5, 131.3, 129.4, 125.9, 123.6, 115.7, 111.8, 96.6, 87.8, 84.3, 62.0, 59.4, 54.8, 44.4, 30.3, 29.2, 25.4, 24.8, 21.7, 20.9, 19.1, 19.0; HRMS (LCMS ESI+) m/z calcd for C₃₀H₃₄O₃N₃S [M+H] 516.2315, found 516.2313.

B. 3-(4-((2-(Cyclohex-2-en-1-ylthio)-1-(pyridin-3-yl)-1H-imidazol-5-yl)methoxy)-2-methylphenyl)prop-2-yn-1-ol (36)

To a solution of 3-(2-(cyclohex-2-en-1-ylthio)-5-((3-methyl-4-(3-((tetrahydro-2H-pyran-2-yl)oxy)prop-1-yn-1-yl)phenoxy)methyl)-1H-imidazol-1-yl)pyridine (35, 0.020 g, 0.39 mmol) in MeOH (0.5 mL) was added PPTS (0.007 g, 0.03 mmol) at room temperature. After 2 d, SM remaining (TLC) additional PPTS (0.007 g, 0.03 mmol) added. After 2 more days (4 total), TLC indicates SM remaining. An additional PPTS (0.010 g, mmol) was added and the solution was warmed to 40-45° C. After 2 h, the reaction was completed. The solution was concentrated, extracted with EtOAc, washed with satd. NaHCO₃, brine, dried (Na₂SO₄), filtered and concentrated. The residue was purified by chromatography on SiO₂ (ISCO-Rf, 0-100% EtOAc/hexanes) to give product (36, 0.011 g, 66%) as an off-white foamy solid: IR (neat) 3225, 2924, 1603, 1494, 1483, 1431, 1290, 1227, 1029, 986, 868, 814, 733, 707 cm⁻¹; ¹H NMR (CDCl₃, 400 MHz) 8.67-8.64 (m, 2H), 7.70 (d, J=8.0 Hz, 1H), 7.41 (dd, J=4.4, 8.0 Hz, 1H), 7.31 (s, 1H), 7.27-7.25 (m, 1H), 6.61 (d, J=2.4 Hz, 1H), 6.55 (dd, J=2.4, 8.4 Hz, 1H), 5.83-5.80 (m, 1H), 5.71-5.68 (m, 1H), 4.74 (d, J=2.0 Hz, 2H), 4.51 (s, 2H), 4.33-4.32 (m, 1H), 2.35 (s, 3H), 2.04-1.90 (m, 3H), 1.89-1.86 (m, 2H), 1.72-1.62 (m, 2H); ¹³C NMR (CDCl₃, 100 MHz) 157.6, 150.3, 148.8, 145.6, 142.2, 135.5, 133.4, 131.6, 131.3, 129.4, 125.9, 123.7, 115.8, 115.5, 111.9, 90.1, 84.1, 59.3, 51.7, 44.4, 29.2, 24.8, 20.9, 19.1; HRMS (LCMS ESI+) m/z calcd for C₂₅H₂₆O₂N₃S [M+H] 432.1740, found 432.1740; ELS purity (100%).

C. 3-(4-((2-(Cyclohex-2-en-1-ylthio)-1-(pyridin-3-yl)-1H-imidazol-5-yl)methoxy)-2-methylphenyl)propiolaldehyde (6)

A solution of 3-(4-((2-(cyclohex-2-en-1-ylthio)-1-(pyridin-3-yl)-1H-imidazol-5-yl)methoxy)-2-methylphenyl)prop-2-yn-1-ol (0.165 g, 0.382 mmol) in CH₂Cl₂ (3.0 mL) was cooled to 0° C. and treated with Dess-Martin periodinane (0.226 g, 0.53 mmol). After 1.5 h at 0° C., the solution was extracted with CH₂Cl₂, washed with 5% NaHSO₃, satd. NaHCO₃, brine, dried (Na₂SO₄), filtered and concentrated. The residue was purified by chromatography on SiO₂ (ISCO-Rf, 0-100% EtOAc/hexanes) to give product (6, 0.121 g, 74%) as a light yellow oil. IR (neat) 2928, 2173, 1648, 1598, 1481, 1431, 1282, 1230, 1119, 977, 868, 815, 705 cm⁻¹; ¹H NMR (CDCl₃, 500 MHz) 9.40 (s, 1H), 8.66 (d, J=4.5 Hz, 1H), 8.61 (d, J=1.5 Hz, 1H), 7.70-7.68 (m, 1H), 7.43 (d, J=8.5 Hz, 1H), 7.42-7.39 (m, 1H), 7.31 (s, 1H), 6.67 (d, J=2.5H, 1H), 6.64 (d, J=2.5 Hz, 1H), 5.82-5.79 (m, 1H), 5.70-5.67 (m, 1H), 4.78 (s, 2H), 4.34-4.32 (m, 1H), 2.42 (s, 3H), 2.03-1.97 (m, 3H), 1.89-1.86 (m, 1H), 1.69-1.61 (m, 2H); ¹³C NMR (CDCl₃, 125 MHz) 176.7, 160.1, 150.5, 148.9, 146.0, 145.3, 135.9, 135.5, 132.2, 131.7, 131.6, 129.0, 126.0, 123.9, 116.2, 112.5, 112.2, 95.1, 92.5, 59.5, 44.4, 29.3, 24.9, 20.9, 19.2; (LCMS ESI+) m/z calcd for C₂₅H₂₄N₃O₂S [M+H] 430.1584, found 430.1583.

D. N-(3-(4-((2-(cyclohex-2-en-1-ylthio)-1-(pyridin-3-yl)-1H-imidazol-5-yl)methoxy)-2-methylphenyl)prop-2-yn-1-yl)-1-methylpiperidin-4-amine (7)

A solution of 3-(4-((2-(cyclohex-2-en-1-ylthio)-1-(pyridin-3-yl)-1H-imidazol-5-yl)methoxy)-2-methylphenyl)propiolaldehyde (6, 0.060 g, 0.14 mmol) in dry MeOH (1.5 mL) was cooled to 0° C. and treated with 4-amino-1-Me-piperidine (0.020 mL, 0.16 mmol). After 5 min, the solution was warmed to room temperature. After 2 h, the solution was treated with NaBH₄ (0.008 g, 0.21 mmol) at room temperature. After 16 h, the solution was concentrated and the residue was diluted with H₂O, extracted with EtOAc, washed with brine, dried (Na₂SO₄), filtered and concentrated. The residue was purified by chromatography on C18 (ISCO-Companion, 10-90% MeCN/H₂O) to give product (7, 0.042 g, 57%) as an orange oil. IR (neat) 2929, 2851, 1603, 1494, 1482, 1432, 1380, 1279, 1228, 1166, 1111, 1028, 987, 909, 813, 728, 707 cm⁻¹; ¹H NMR (CDCl₃, 500 MHz) 8.62 (dd, J=1.5, 5.0 Hz, 1H), 8.59 (d, J=2.5 Hz, 1H), 7.67-7.65 (m, 1H), 7.35 (dd, J=5.0, 8.0 Hz, 1H), 7.22 (s, 1H), 7.21-7.19 (m, 1H), 6.58 (d, J=2.5 Hz, 1H), 6.50 (dd, J=2.5, 8.5H, 1H), 5.79-5.76 (m, 1H), 5.66-5.64 (m, 1H), 4.70 (d, J=3.0 Hz, 2H), 4.29-4.26 (m, 1H), 3.65 (s, 2H), 2.87-2.84 (m, 4H), 2.31 (s, 3H), 2.24 (s, 3H), 2.00-1.94 (m, 6H), 1.86-1.83 (m, 3H), 1.69-1.64 (m, 1H), 1.59-1.56 (m, 1H), 1.47-1.39 (m, 2H); ¹³C NMR (CDCl₃, 100 MHz) 157.4, 150.4, 149.0, 145.7, 142.0, 135.6, 133.3, 132.3, 131.7, 131.5, 129.6, 126.1, 123.8, 116.3, 115.9, 112.0, 90.4, 82.9, 59.5, 54.2, 46.1, 44.5, 36.2, 32.1, 29.3, 25.0, 21.1, 19.3; HRMS (LCMS ESI+) m/z calcd for C₃₁H₃₈N₅OS [M+H] 528.2792, found 528.2789; ELS purity (99.2%).

Example 5. 3-(4-((2-((Cyclopentyl-d₉)thio)-1-(pyridin-3-yl)-1H-imidazol-5-yl)methoxy)-2-fluorophenyl)prop-2-yn-1-yl (1-methylpiperidin-4-yl)carbamate

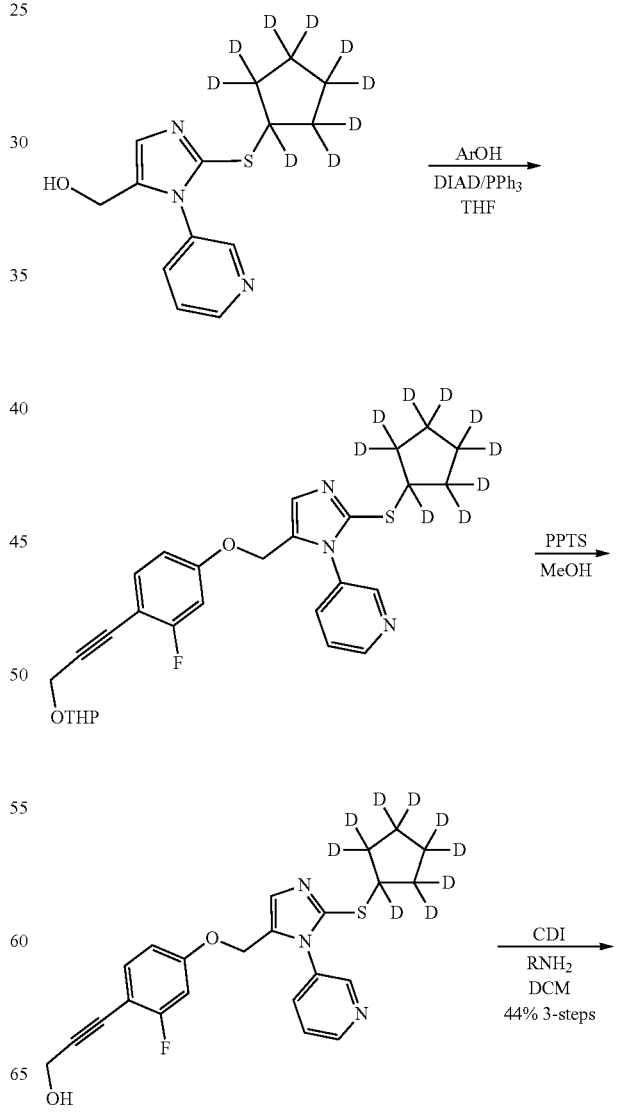

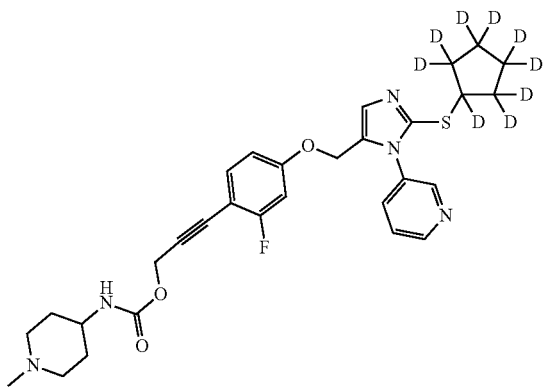

A. 3-(2-((Cyclopentyl-d₉)thio)-5-((3-fluoro-4-(3-((tetrahydro-2H-pyran-2-yl)oxy)prop-1-yn-1-yl)phenoxy)methyl)-1H-imidazol-1-yl)pyridine A solution of (2-((cyclopentyl-d₉)thio)-1-(pyridin-3-yl)-1H-imidazol-5-yl)methanol (0.220 g, 0.77 mmol, prepared similarly as shown in Example 2), 3-fluoro-4-(3-((tetrahydro-2H-pyran-2-yl)oxy)prop-1-yn-1-yl)phenol (0.235 g, 0.94 mmol), PPh₃ (0.247 g, 0.93 mmol), in THF (3.0 mL) was cooled to 0° C. and treated with DIAD (0.18 mL, 0.88 mmol). After 10 min, the solution was warmed to room temperature and kept at this temperature overnight. The solution was extracted with EtOAc, washed with brine, dried (Na₂SO₄), filtered and concentrated. The residual oil was purified by chromatography on SiO₂ (ISCO-Rf, 0-100% EtOAc/hexanes) to give product that was used without further purification: HRMS (LCMS ESI+) m/z calcd for C₂₈H₂₂D₉O₃N₃SF [M+H] 517.2630, found 517.2628.

B. 3-(4-((2-((Cyclopentyl-d₉)thio)-1-(pyridin-3-yl)-1H-imidazol-5-yl)methoxy)-2-fluorophenyl)prop-2-yn-1-ol To a solution of 3-(2-((cyclopentyl-d₉)thio)-5-((3-fluoro-4-(3-((tetrahydro-2H-pyran-2-yl)oxy)prop-1-yn-1-yl)phenoxy)methyl)-1H-imidazol-1-yl)pyridine (0.772 mmol, theoretical) in MeOH (5.0 mL) was added PPTS (0.21 g, 0.84 mmol) at room temperature and kept at this temperature overnight. The solution was heated to reflux for 1 h, cooled to room temperature, extracted with EtOAc, washed with satd. NaHCO₃, brine, dried (Na₂SO₄), filtered and concentrated. The residual oil was purified by chromatography on SiO₂ (ISCO-Rf, 0-100% EtOAc/hexanes) to give product (0.168 g) that was used without further purification: HRMS (LCMS ESI+) m/z calcd for C₂₃H₁₄D₉O₂N₃SF [M+H] 433.2054, found 433.1878.

C. 3-(4-((2-((Cyclopentyl-d₉)thio)-1-(pyridin-3-yl)-1H-imidazol-5-yl)methoxy)-2-fluorophenyl)prop-2-yn-1-yl (1-methylpiperidin-4-yl)carbamate To a solution of 3-(4-((2-((cyclopentyl-d₉)thio)-1-(pyridin-3-yl)-1H-imidazol-5-yl)methoxy)-2-fluorophenyl)prop-2-yn-1-ol (0.168 g) in CH₂Cl₂ (2.5 mL) was added CDI (0.067 g, 0.41 mmol) at room temperature. After 2.5 h, 1-methylpiperidin-4-amine (0.107 g, 0.94 mmol) in CH₂Cl₂ (0.3 mL) was added dropwise at room temperature. After 16 h, the solution was extracted with CH₂Cl₂, washed with brine. The aqueous was back-extracted with EtOAc. The combined organic layer was dried (Na₂SO₄), filtered and concentrated. The residual oil was purified by chromatography on SiO₂ (ISCO-Rf, 0-10% MeOH/CH₂Cl₂) to give product (0.078 g, 44%-3-steps) as an orangish foamy solid residue: IR (neat) 2937, 2790, 1708, 1619, 1504, 1431, 1272, 1224, 1161, 1116, 1043, 999, 813, 708 cm⁻¹; ¹H NMR (CDCl₃, 600 MHz) 8.68 (app t, J=3.6 Hz, 1H), 8.61 (d, J=1.8 Hz, 1H), 7.69-7.67 (m, 1H), 7.41 (dd, J=4.8, 7.8 Hz, 1H), 7.31-7.29 (m, overlapping signals, 2H), 6.54-6.49 (m, 2H), 4.90 (s, 2H), 4.75 (s, 3H), 3.58-3.55 (m, 1H), 2.84-2.81 (m, 2H), 2.31 (s, 3H), 2.18-2.14 (m, 2H), 1.98-1.96 (m, 2H), 1.55-1.52 (m, 2H); ¹³C NMR (CDCl₃, 151 MHz) 164.5, 162.8, 159.2, 159.1, 154.7, 150.4, 148.7, 146.7, 135.3, 134.4, 134.3, 132.1, 131.6, 128.5, 123.8, 110.6, 110.5, 103.7, 103.6, 102.6, 102.4, 87.5, 79.4, 59.8, 54.2, 53.2, 45.9, 32.1. ¹⁹F NMR (CDCl₃, 376 MHz) −106.9; HRMS (LCMS ESI+) m/z calcd for C₃₀H₂₆D₉O₃N₅SF [M+H] 573.3004, found 573.2999; ELS purity (100%).

Example 6. N-(3-(4-((2-(Cyclohex-2-en-1-ylthio)-1-(pyridin-3-yl)-1H-imidazol-5-yl)methoxy)-2-methylphenyl)-prop-2-yn-1-yl)acetamide

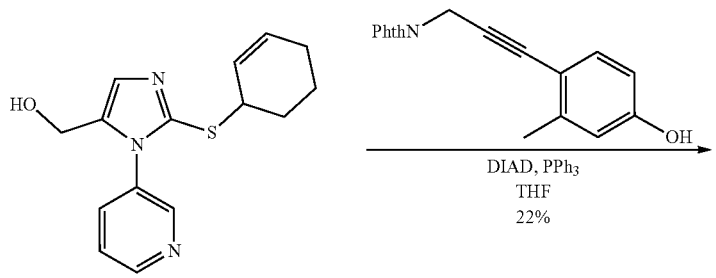

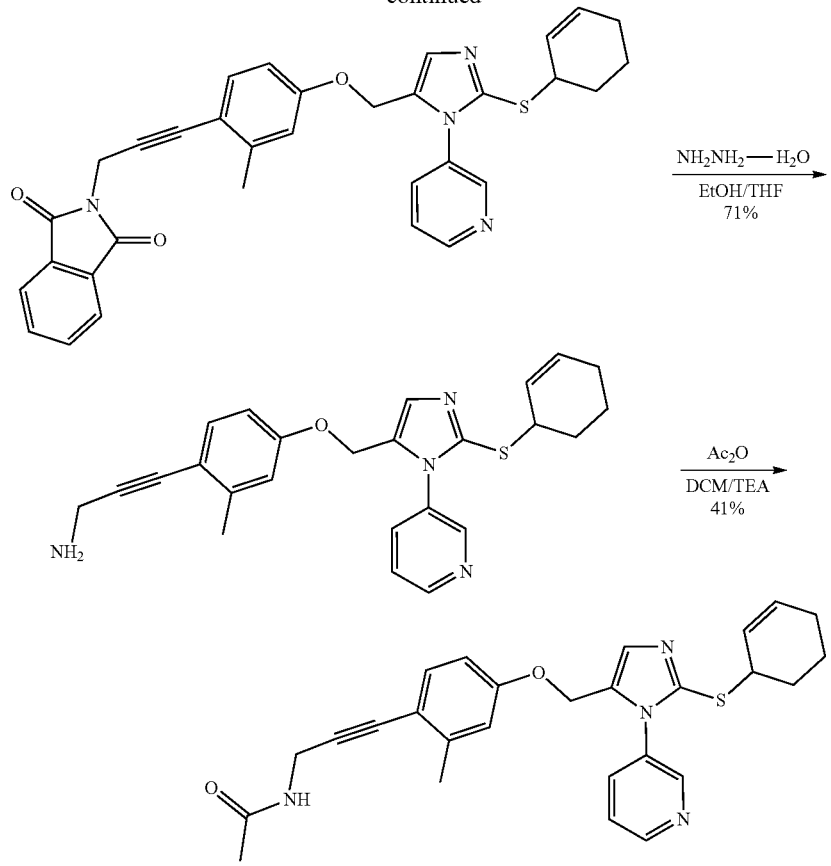

A. 2-(3-(4-((2-(Cyclohex-2-en-1-ylthio)-1-(pyridin-3-yl)-1H-imidazol-5-yl)methoxy)-2-methyl-phenyl)prop-2-yn-1-yl)isoindoline-1,3-dione To a solution of (2-(cyclohex-2-en-1-ylthio)-1-(pyridin-3-yl)-1H-imidazol-5-yl)methanol (0.098 g, 0.34 mmol, prepared similarly as shown in Example 2), triphenylphosphine (0.11 g, 0.41 mmol) and 2-(3-(4-hydroxy-2-methylphenyl)prop-2-yn-1-yl)isoindoline-1,3-dione (0.12 g, 0.41 mmol) in dry THF (1.0 mL) was added DIAD (0.081 ml, 0.41 mmol) dropwise at 0° C. The solution was stirred overnight at rt. The reaction was poured into water and extracted with EtOAc. The organic layer was washed with brine, dried (Na$_2$SO$_4$), filtered and concentrated. The crude residue was purified by chromatography on SiO$_2$ (20% EtOAc/CH$_2$Cl$_2$) followed by chromatography on C18 (10-95% MeCN/H$_2$O) to give product (0.041 g, 22%) as a colorless oil: $^1$H NMR (CDCl$_3$, 300 MHz) 8.68 (s, 2H), 7.91 (dd, J=5.5, 3.1 Hz, 2H), 7.76 (dd, J=5.5, 3.1 Hz, 2H), 7.71 (d, J=7.9 Hz, 1H), 7.47-7.38 (m, 1H), 7.33 (s, 1H), 7.26 (d, J=8.5 Hz, 1H), 6.60 (d, J=2.5 Hz, 1H), 6.54 (dd, J=8.5, 2.6 Hz, 1H), 5.89-5.79 (m, 1H), 5.75-5.66 (m, 1H), 4.80-4.74 (m, 2H), 4.70 (s, 2H), 4.36 (m, 1H), 2.35 (s, 3H), 2.05-1.53 (m, 6H).

B. 3-(4-((2-(Cyclohex-2-en-1-ylthio)-1-(pyridin-3-yl)-1H-imidazol-5-yl)methoxy)-2-methylphenyl)prop-2-yn-1-amine Hydrazine monohydrate (0.059 mL, 1.23 mmol) was added to a solution of 2-(3-(4-((2-(cyclohex-2-en-1-ylthio)-1-(pyridin-3-yl)-1H-imidazol-5-yl)methoxy)-2-methylphenyl)prop-2-yn-1-yl)isoindoline-1,3-dione (0.078 g, 0.12 mmol) in ethanol (1.25 mL) and THF (0.63 mL). After 2 h, the reaction mixture was filtered through Celite and rinsed with EtOAc and concentrated to give product (0.042 g, 71%) as an off white solid: $^1$H NMR (CDCl$_3$, 300 MHz) 8.59 (dd, J=4.8, 1.6 Hz, 1H), 8.55 (d, J=2.5 Hz, 1H), 7.64 (dt, J=8.2, 2.0 Hz, 1H), 7.33 (dd, J=8.1, 4.7 Hz, 1H), 7.23 (s, 1H), 7.17 (d, J=8.4 Hz, 1H), 6.54 (d, J=2.6 Hz, 1H), 6.48 (dd, J=8.4, 2.7 Hz, 1H), 5.81-5.69 (m, 1H), 5.61 (ddt, J=9.5, 4.1, 2.1 Hz, 1H), 4.83-4.55 (m, 2H), 3.58-3.55 (m, 2H), 2.71 (s, 2H), 2.27 (s, 3H), 1.96-1.44 (m, 6H).

C. N-(3-(4-((2-(Cyclohex-2-en-1-ylthio)-1-(pyridin-3-yl)-1H-imidazol-5-yl)methoxy)-2-methylphenyl)prop-2-yn-1-yl)acetamide To a solution of 3-(4-((2-(cyclohex-2-en-1-ylthio)-1-(pyridin-3-yl)-1H-imidazol-5-yl)methoxy)-2-methylphenyl)prop-2-yn-1-amine (0.0546 g, 0.127 mmol) in CH$_2$Cl$_2$ (1.0 mL) at −40° C. were added triethylamine (0.018 mL, 0.13 mmol) followed by acetic anhydride (0.010 mL, 0.11 mmol). The solution was warmed to 0° C. After 1 h, the reaction mixture was concentrated and purified by chromatography on SiO$_2$ (100% EtOAc) to give product (0.018 g, 41%) as a clear oil: $^1$H NMR (CDCl$_3$, 300 MHz) 8.68-8.65 (m, 2H), 7.73 (d, J=8.1 Hz, 1H), 7.45 (d, J=6.6 Hz, 1H), 7.35 (s, 1H), 7.26 (d, J=8.4 Hz, 1H), 6.63 (d, J=2.6 Hz, 1H), 6.57 (dd, J=8.6, 2.6 Hz, 1H), 5.97-5.80 (m, 2H), 5.77-5.66 (m, 1H), 4.76 (s, 2H), 4.40-4.36 (m, 1H), 4.30 (d, J=5.2 Hz, 2H), 2.35 (s, 3H), 2.10-1.56 (m, 9H); $^{13}$C NMR (CDCl$_3$, 101 MHz) 169.6, 157.5, 150.3, 148.7, 145.6, 142.2, 135.4, 133.4, 132.2, 131.7, 130.7, 129.4, 125.7, 123.7, 115.7, 115.4, 111.8, 87.34, 81.8, 59.2, 44.5, 30.2, 29.1, 24.8, 23.1, 20.9, 19.03; HRMS (LCMS ESI+) m/z calcd for $C_{27}H_{29}N_4O_2S$ [M+H] 473.2006, found 473.2003.

Example 7. 4-Halo-2-(cyclohex-2-en-1-ylthio)-1-(pyridin-3-yl)-1H-imidazol-5-yl)methanol

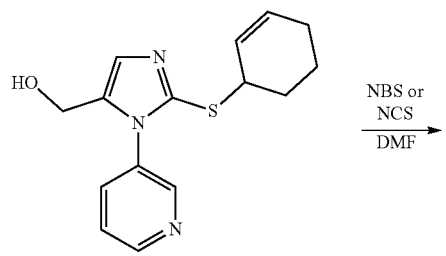

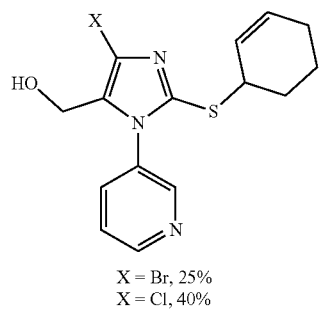

X = Br, 25%
X = Cl, 40%

4-Bromo-2-(cyclohex-2-en-1-ylthio)-1-(pyridin-3-yl)-1H-imidazol-5-yl)methanol

To a solution of (2-(cyclohex-2-en-1-ylthio)-1-(pyridin-3-yl)-1H-imidazol-5-yl)methanol (1.07 g, 3.72 mmol) in dry DMF (20 mL) at −40° C. was added N-bromosuccinimide (0.696 g, 3.91 mmol) dissolved in DMF (15 mL) dropwise. The reaction was warmed to 0° C. and stirred at this temperature until complete as evidenced by LCMS. Additional N-bromosuccinimide (0.200 g, 1.12 mmol) was added to achieve complete conversion. The reaction was then diluted with EtOAc, washed with $H_2O$ (2×), brine, dried ($Na_2SO_4$), filtered and concentrated. The product was purified by chromatography on $SiO_2$ (30-60% $CH_2Cl_2$/EtOAc) to give product (0.38 g, 25%) as an orangish-white foam: $^1$H NMR (CDCl$_3$, 300 MHz) 8.74-8.64 (m, 1H), 8.60 (s, 1H), 7.79 (dt, J=8.1, 1.9 Hz, 1H), 7.48 (dd, J=8.2, 4.8 Hz, 1H), 5.80 (ddt, J=10.8, 4.7, 2.3 Hz, 1H), 5.64 (ddd, J=10.0, 4.3, 2.2 Hz, 1H), 4.40 (d, J=1.6 Hz, 2H), 4.27 (m, 1H), 3.09 (s, 1H), 2.02-1.50 (m, 6H); $^{13}$C NMR (CDCl$_3$, 101 MHz) 150.0, 148.3, 144.1, 135.8, 132.2, 131.77, 131.1, 125.5, 123.9, 117.1, 53.2, 44.7, 29.0, 24.7, 18.9; HRMS (LCMS ESI+) m/z calcd for $C_{15}H_{17}BrN_3OS$ [M+H] 366.0270, found 366.0077.

(4-Chloro-2-(cyclohex-2-en-1-ylthio)-1-(pyridin-3-yl)-1H-imidazol-5-yl)methanol

To a solution of (2-(cyclohex-2-en-1-ylthio)-1-(pyridin-3-yl)-1H-imidazol-5-yl)methanol (1.23 g, 4.28 mmol) in DMF (20 mL) was added NCS (0.64 g, 4.71 mmol) in one portion. The reaction was heated to 60° C. and stirred for 3 h. The reaction was diluted with Et$_2$O, washed with H$_2$O (2×), brine, dried (Na$_2$SO$_4$), filtered and concentrated. The crude mixture was purified by chromatography on SiO$_2$ (30-60% CH$_2$Cl$_2$/EtOAc) to give product (0.058 g, 40%) as a colorless oil: $^1$H NMR (CDCl$_3$, 300 MHz) 8.68-8.65 (m, 2H), 7.73 (d, J=8.1 Hz, 1H), 7.45 (d, J=6.6 Hz, 1H), 7.35 (s, 1H), 7.26 (d, J=8.4 Hz, 1H), 6.63 (d, J=2.6 Hz, 1H), 6.57 (dd, J=8.6, 2.6 Hz, 1H), 5.97-5.80 (m, 2H), 5.77-5.66 (m, 1H), 4.76 (s, 2H), 4.40-4.37 (m, 1H), 4.30 (d, J=5.2 Hz, 2H), 2.35 (s, 3H), 2.10-1.56 (m, 9H); $^{13}$C NMR (CDCl$_3$, 101 MHz) 169.6, 157.5, 150.3, 148.7, 145.6, 142.2, 135.4, 133.4, 132.2, 131.7, 130.7, 129.4, 125.7, 123.7, 115.7, 115.4, 111.8, 87.4, 81.8, 59.2, 44.5, 30.2, 29.1, 24.8, 23.1, 20.8, 19.0; HRMS (LCMS ESI+) m/z calcd for $C_{15}H_{17}ClN_3OS$ [M+H] 322.0775, found 322.0772.

Example 8. 3-(4-((2-(Ethylsulfonyl)-1-(pyridin-3-yl)-1H-imidazol-5-yl)methoxy)-2-methylphenyl)prop-2-yn-1-ol

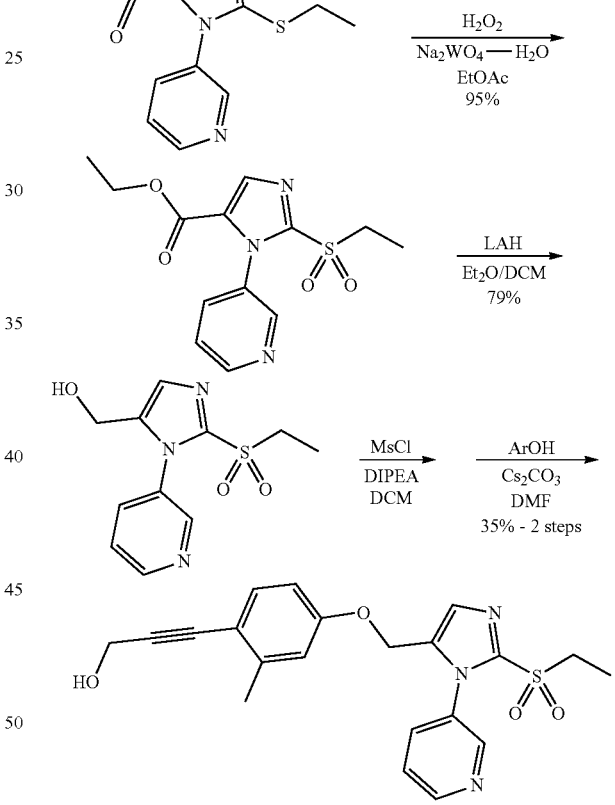

A. Ethyl 2-(ethylthio)-1-(pyridin-3-yl)-1H-imidazole-5-carboxylate

A solution of ethyl 2-mercapto-1-(pyridin-3-yl)-1H-imidazole-5-carboxylate (0.166 g, 0.667 mmol) in DMF (2.5 mL) was treated with Cs$_2$CO$_3$ (0.327 g, 1.00 mmol) followed by iodoethane (0.060 mL, 0.74 mmol) at room temperature. After 1.5 h, the solution was extracted with EtOAc, washed with brine, dried (Na$_2$SO$_4$), filtered and concentrated. The residue was purified by chromatography on SiO$_2$ (ISCO-Rf, 0-100% EtOAc/hexanes) to give product (0.177 g, 96%, small amount residual solvent) as a light yellow solid: M.p. 64-66° C.; IR (neat) 2982, 1707, 1535, 1480, 1429, 1368, 1275, 1156, 1142, 1016, 953, 814, 763, 708, 693 cm$^{-1}$; $^1$H NMR (CDCl$_3$, 500 MHz) 8.66 (d, J=4.5 Hz, 1H), 8.48 (d, J=2.5 Hz, 1H), 7.79 (s, 1H), 7.60-7.57 (m, 1H), 7.38 (dd, J=4.5, 8.0 Hz, 1H), 4.08 (q, J=7.0 Hz, 2H), 3.15 (q, J=7.5 Hz, 2H), 1.30 (t, J=7.0 Hz, 3H), 1.12 (t, J=7.0 Hz, 3H); $^{13}$C NMR (CDCl$_3$, 125 MHz) 159.0, 151.0, 150.2, 148.4, 137.9, 135.1, 133.0, 125.7, 123.5, 60.5, 26.9, 14.7, 14.1; HRMS (LCMS ESI+) m/z calcd for C$_{13}$H$_{16}$N$_3$O$_2$S [M+H] 278.0958, found 278.0953.

B. Ethyl 2-(ethylsulfonyl)-1-(pyridin-3-yl)-1H-imidazole-5-carboxylate

A solution of ethyl 2-(ethylthio)-1-(pyridin-3-yl)-1H-imidazole-5-carboxylate (0.078 g, 0.28 mmol) in EtOAc (1.0 mL) was treated with H$_2$O (0.10 mL) followed by Na$_2$WO$_4$.2 H$_2$O (0.011 g, 0.033 mmol). The solution was cooled to 0° C. and treated with H$_2$O$_2$ (0.10 mL, 30% aqueous). After 1 h, the solution was warmed to room temperature. After 23 h, the solution was treated with satd. NaHCO$_3$, extracted with EtOAc, washed with brine, dried (Na$_2$SO$_4$), filtered and concentrated. The residue was purified by chromatography on SiO$_2$ (ISCO-Rf, 0-100% EtOAc/hexanes) to give product (0.083 g, 95%) as a white solid: M.p. 92-93° C.; IR (neat) 3111, 2985, 1718, 1583, 1522, 1481, 1431, 1324, 1289, 1276, 1175, 1135, 1015, 816, 772, 736, 706 cm$^{-1}$; $^1$H NMR (CDCl$_3$, 500 MHz) 8.73 (dd, J=1.5, 5.0 Hz, 1H), 8.59 (d, J=2.0 Hz, 1H), 7.86 (s, 1H), 7.77-7.74 (m, 1H), 7.44 (dd, J=5.0, 8.5 Hz, 1H), 4.16 (q, J=7.0 Hz, 2H), 3.47-3.45 (m, 2H), 1.37 (t, J=7.5 Hz, 3H), 1.17 (t, J=7.0 Hz, 3H); $^{13}$C NMR (CDCl$_3$, 125 MHz) 158.3, 151.0, 147.9, 147.0, 135.8, 135.2, 132.0, 128.0, 123.3, 61.6, 49.5, 14.0, 6.9; HRMS (LCMS ESI+) m/z calcd for C$_{13}$H$_{16}$N$_3$O$_4$S [M+H] 310.0856, found 310.0862.

C. (2-(Ethylsulfonyl)-1-(pyridin-3-yl)-1H-imidazol-5-yl)methanol

A solution of LAH (0.10 mL, 1.0 M Et$_2$O, diluted 4M solution) in dry Et$_2$O (3.0 mL) was cooled to −40° C. and treated with ethyl 2-(ethylsulfonyl)-1-(pyridin-3-yl)-1H-imidazole-5-carboxylate (0.025 g, 0.081 mmol) in CH$_2$Cl$_2$ (2.0 mL). After 5 min, the reaction mixture was treated with H$_2$O (0.3 mL), 0.5M NaOH (0.3 mL) and H$_2$O (0.3 mL). The mixture was diluted with EtOAc and warmed to room temperature. To the solution was added Na$_2$SO$_4$ and the mixture was filtered and concentrated. The residue was purified by chromatography on SiO$_2$ (ISCO-Rf, 0-10% MeOH/CH$_2$Cl$_2$) to give product (0.017 g, 79%) as a light yellow oil: IR (neat) 3281, 2924, 2855, 1482, 1435, 1322, 1277, 1152, 1131, 1027, 910, 815, 775, 728, 705 cm$^1$; $^1$H NMR (CDCl$_3$, 500 MHz) 8.72 (br s, 1H), 8.65 (br s, 1H), 7.85 (d, J=8.5 Hz, 1H), 7.49 (dd, J=4.5, 7.0 Hz, 1H), 7.27 (s, 1H), 4.45 (s, 2H), 3.41 (q, J=7.5 Hz, 2H), 2.19 (br s, 1H), 1.35 (t, J=7.5 Hz, 3H); $^{13}$C NMR (CDCl$_3$, 125 MHz) 157.1, 151.0, 148.2, 144.1, 137.0, 136.0, 128.9, 123.9, 53.7, 49.7, 6.9; HRMS (LCMS ESI+) m/z calcd for C$_{11}$H$_{14}$N$_3$O$_3$S [M+H] 268.0750, found 268.0748.

D. 3-(5-(Chloromethyl)-2-(ethylsulfonyl)-1H-imidazol-1-yl)pyridine

A solution of (2-(ethylsulfonyl)-1-(pyridin-3-yl)-1H-imidazol-5-yl)methanol (0.017 g, 0.064 mmol) in CH$_2$Cl$_2$ (1.5 mL) was cooled to 0° C. and treated with DIPEA (0.015 mL, 0.091 mmol) followed by methane sulfonylchloride (0.010 mL, 0.13 mmol). After 10 min, the solution was warmed to room temperature. After 2 h, the solution was extracted with CH$_2$Cl$_2$, washed with brine, dried (Na$_2$SO$_4$), filtered and concentrated to give crude product (0.014 g) that was used without further purification. HRMS (LCMS ESI+) m/z calcd for C$_{11}$H$_{13}$N$_3$O$_2$SCl [M+H] 286.0412, found 286.0409.

E. 3-(4-((2-(Ethylsulfonyl)-1-(pyridin-3-yl)-1H-imidazol-5-yl)methoxy)-2-methylphenyl)prop-2-yn-1-ol A solution of 3-(5-(chloromethyl)-2-(ethylsulfonyl)-1H-imidazol-1-yl)pyridine (0.014 g, 0.049 mmol, crude) in DMF (2.0 mL) was treated with 4-(3-hydroxyprop-1-yn-1-yl)-3-methylphenol (0.015 g, 0.092 mmol) followed by Cs$_2$CO$_3$ (0.026 g, 0.080 mmol) at room temperature. After 2 h, the solution was extracted with EtOAc, washed with brine (2×), dried (Na$_2$SO$_4$), filtered and concentrated. The residue was purified by chromatography on SiO$_2$ (ISCO-Rf, 0-100% EtOAc/hexanes) to give product (0.007 g, 35%, 2-steps) as an orange oil: $^1$H NMR (CDCl$_3$, 500 MHz) 8.72 (br s, 2H), 7.82 (d, J=8.0 Hz, 1H), 7.43 (dd, J=4.5, 7.5 Hz, 1H), 7.39 (s, 1H), 7.28-7.26 (m, 1H), 6.60 (d, J=2.0 Hz, 1H), 6.53 (dd, J=2.5, 8.5 Hz, 1H), 4.75 (s, 2H), 4.50 (s, 2H), 3.46 (q, J=7.5 Hz, 2H), 2.35 (s, 3H), 2.21 (br s, 1H), 1.39 (t, J=7.5 Hz, 3H); $^{13}$C NMR (CDCl$_3$, 151 MHz) 157.4, 151.3, 148.2, 144.8, 142.5, 135.7, 133.6, 132.7, 132.2, 130.4, 123.8, 116.1, 115.8, 111.9, 90.4, 84.1, 58.8, 51.8, 49.6, 21.0, 7.0; HRMS (LCMS ESI+) m/z calcd for C$_{21}$H$_{22}$N$_3$O$_4$S [M+H] 412.1326, found 412.1321; ELS purity (100%).

Example 9. 2-(Cyclopentylthio)-5-(hydroxymethyl)-1-(pyridin-3-yl)-1H-imidazole-4-carbonitrile

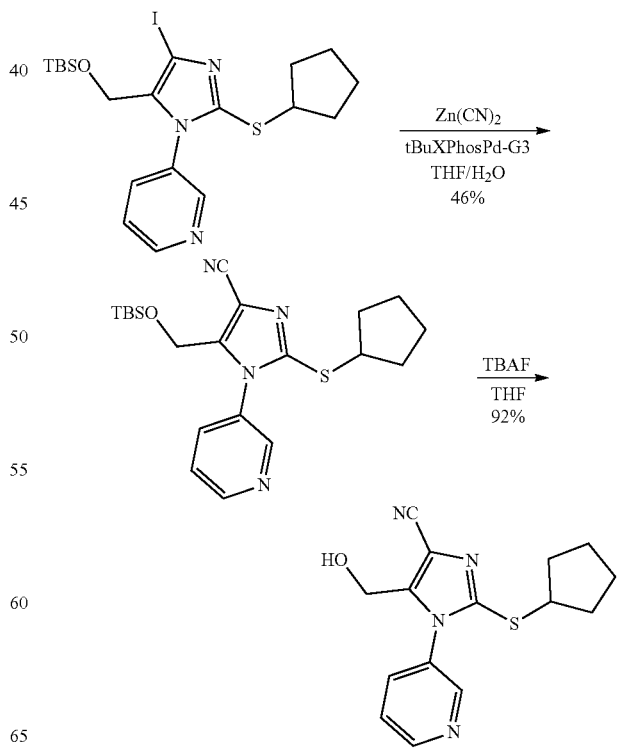

A. 5-(((tert-Butyldimethylsilyl)oxy)methyl)-2-(cyclopentylthio)-1-(pyridin-3-yl)-1H-imidazole-4-carbonitrile A sealed tube equipped with a magnetic stirbar was charged with tBuXPhos Pd G3 (0.068 g, 0.083 mmol), 3-(5-(((tert-butyldimethylsilyl)oxy)methyl)-2-(cyclopentylthio)-4-iodo-1H-imidazol-1-yl)pyridine (0.213 g, 0.413 mmol), and Zn(CN)$_2$ (0.146 g, 1.24 mmol). The reaction vial was evacuated and refilled with nitrogen (3×). To this mixture was added THF (1.0 mL) and degassed distilled H$_2$O (3.0 mL). The reaction mixture was heated at 40° C. for 44.5 h. After cooling the mixture to room temperature, the mixture was quenched with satd. NaHCO$_3$ (20 mL) and diluted with EtOAc (20 mL). The mixture was extracted with EtOAc (3×15 mL). The combined organic phase was dried (MgSO$_4$), filtered and concentrated in vacuo. The crude product was purified by flash chromatography on SiO$_2$ (20% EtOAc/hexanes) to give the product (0.078 g, 46%): $^1$H NMR (CDCl$_3$, 500 MHz) 8.77 (br s, 1H), 8.61 (br s, 1H), 7.71-7.69 (m, 1H), 7.48 (dd, J=4.5, 6.6 Hz, 1H), 4.51 (s, 2H), 3.92 (pent, J=7.0 Hz, 1H), 2.16-2.12 (m, 2H), 1.69-1.52 (m, 6H), 1.27-1.24 (m, 2H) 0.78 (s, 9H), 0.04 (s, 6H); $^{13}$C NMR (CDCl$_3$, 125 MHz) 150.9, 148.5, 148.1, 141.6, 135.7, 123.9, 112.0, 114.1, 53.7, 46.2, 33.6, 27.9, 25.6, 24.5, 18.0, −5.7

B. 2-(Cyclopentylthio)-5-(hydroxymethyl)-1-(pyridin-3-yl)-1H-imidazole-4-carbonitrile A solution of 5-(((tert-butyldimethylsilyl)oxy)methyl)-2-(cyclopentylthio)-1-(pyridin-3-yl)-1H-imidazole-4-carbonitrile (0.078 g, 0.19 mmol) in THF (1.9 mL) was cooled to 0° C. and treated with TBAF (0.21 mL, 1M in THF). The mixture was stirred for 3 h at room temperature. Then the solution was quenched with water (30 mL), extracted with EtOAc (3×30 mL), dried (Na$_2$SO$_4$), filtered and concentrated in vacuo. The residue was purified by chromatography on SiO$_2$ (66% EtOAc/hexanes) to give product (0.052 g, 92%) as a white solid: M.p. 136-137° C.; IR (neat) 3248, 2957, 2868, 2231, 1484, 1449, 1429, 1278, 1029, 993, 821, 734, 708 cm$^{-1}$; $^1$H NMR (CDCl$_3$, 400 MHz) 8.74 (br s, 1H), 8.64 (br s, 1H), 7.85 (d, J=8.0 Hz, 1H), 7.53 (d, J=4.4 Hz, 1H), 4.52 (s, 2H), 3.89 (pent, J=6.4 Hz, 1H), 2.17-2.09 (m, 2H), 1.72-1.58 (m, 6H); $^{13}$C NMR (CDCl$_3$, 100 MHz) 150.8, 148.5, 148.2, 142.4, 135.9, 131.3, 124.3, 114.1, 114.0, 52.6, 46.3, 33.6, 24.5.

Example 10. Ethyl 2-(cyclopentylthio)-5-(hydroxymethyl)-1-(pyridin-3-yl)-1H-imidazole-4-carboxylate

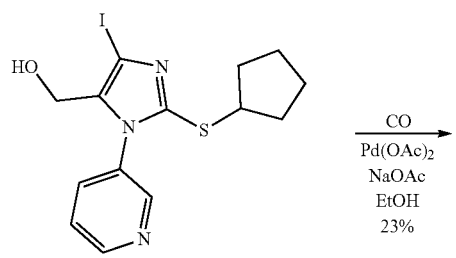

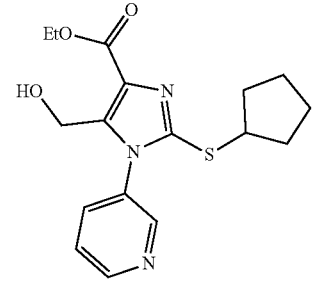

Palladium(II) acetate (1.34 mg, 0.0059 mmol) was added to a solution of the (2-(cyclopentylthio)-4-iodo-1-(pyridin-3-yl)-1H-imidazol-5-yl)methanol (0.030 g, 0.075 mmol) and sodium acetate (0.025 g, 0.31 mmol) in anhydrous ethanol (0.75 mL). The reaction mixture was stirred for 67 h at room temperature under an atmosphere of carbon monoxide. The mixture was filtered through Celite and the filtrate was concentrated in vacuo. The residue was purified by flash column chromatography on SiO$_2$ (75-80% EtOAc/hexanes) to afford the desired product (0.006 g, 23%) as a light yellow oil: $^1$H NMR (CDCl$_3$, 400 MHz) 8.77 (d, J=4.0 Hz, 1H), 8.58 (d, J=2.0 Hz, 1H), 7.69-7.67 (m, 1H), 7.50 (dd, J=4.8, 8.0 Hz, 1H), 4.53 (br s, 2H), 4.46 (q, J=7.2 Hz, 2H), 3.88 (pent, J=6.8 Hz, 1H), 3.73 (app t, J=6.8 Hz, 1H), 2.08-2.01 (m, 2H), 1.68-1.49 (m, 6H), 1.44 (t, J=7.2 Hz, 3H).

Example 11. 2-(Cyclopentylthio)-5-((3-methyl-4-(3-((tetrahydro-2H-pyran-2-yl)oxy)prop-1-yn-1-yl)phenoxy)-methyl)-1-(pyridin-3-yl)-1H-imidazole-4-carboxamide

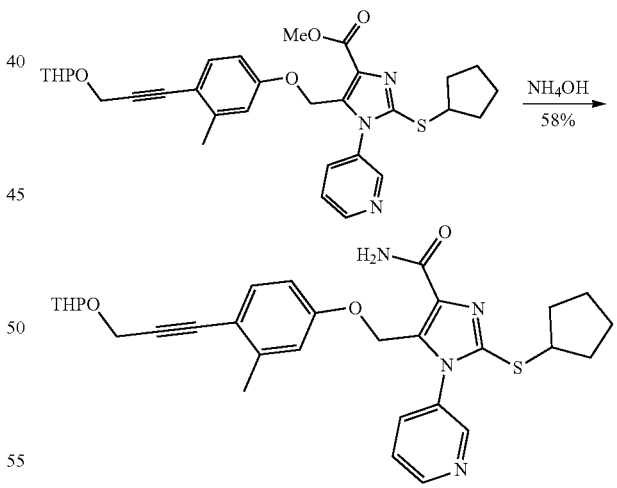

To the flame-dried sealed tube was added methyl 2-(cyclopentylthio)-5-((3-methyl-4-(3-((tetrahydro-2H-pyran-2-yl)oxy)prop-1-yn-1-yl)phenoxy)methyl)-1-(pyridin-3-yl)-1H-imidazole-4-carboxylate (0.087 mg, 0.154 mmol) and 28% NH$_4$OH (1.54 mL). The mixture was heated at 120° C. for 38 h, cooled to room temperature, quenched with H$_2$O (10 mL) and extracted with EtOAc (3×10 mL). The combined organic layer was dried (Na$_2$SO$_4$), filtered, concentrated. The crude residue was purified by chromatography on SiO$_2$ (33% EtOAc/hexanes) to give the desired product (0.049 mg, 58%) as a colorless oil: $^1$H NMR (CDCl$_3$, 400 MHz) 8.72 (d, J=4.0 Hz, 1H), 8.59 (s, 1H), 7.68-7.64 (m, 1H) 7.43 (dd, J=0.5, 8.0 Hz, 1H), 7.24 (d, J=8.8 Hz, 2H), 7.15 (d, J=3.2 Hz, 1H), 6.68 (d, J=2.4 Hz, 1H), 6.60 (dd, J=2.4, 8.4 Hz, 1H), 5.52 (d, J=2.8 Hz, 1H), 5.34 (s, 2H), 4.91 (app t, J=3.6 Hz, 1H), 4.49 (d, J=15.6 Hz, 2H), 3.91-3.81 (m, 2H), 3.58-3.52 (m, 1H), 2.34 (s, 3H), 2.12-2.06 (m, 2H), 1.86-1.52 (m, 12H).

Example 12. (5-(Cyclopentylmethyl)-4-(pyridin-3-yl)-4H-1,2,4-triazol-3-yl)methanol

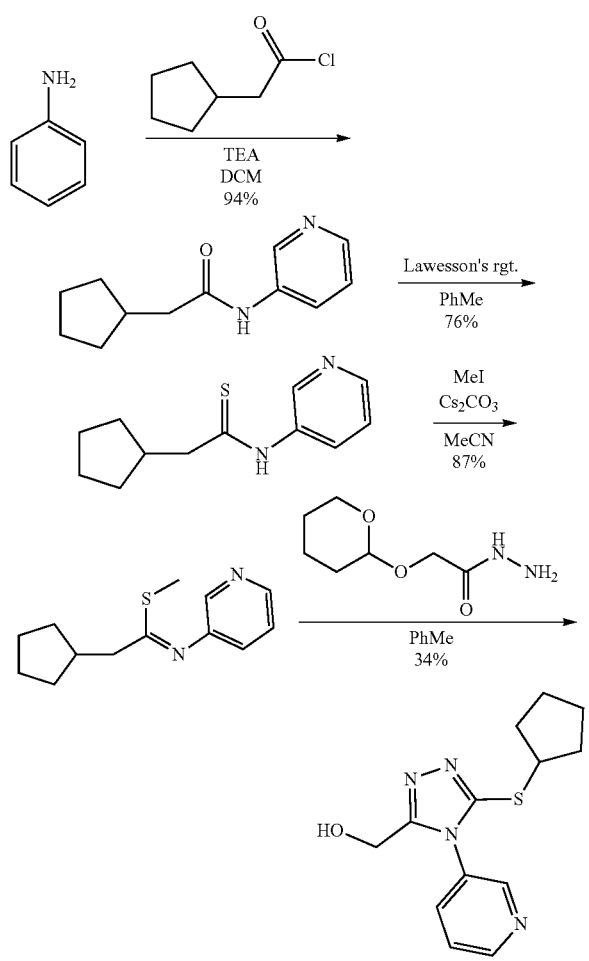

A. 2-Cyclopentyl-N-(pyridin-3-yl)acetamide

To a 100 mL round bottom flask under nitrogen atmosphere was added 3-aminopyridine (0.95 g, 10.0 mmol), dry CH$_2$Cl$_2$ (12 mL), and TEA (1.01 g, 10.0 mmol). This solution was brought to 0° C. and cyclopentylacetyl chloride (1.47 g, 10.0 mmol) was added dropwise. The reaction mixture was allowed to stir overnight and was poured into H$_2$O, extracted with CH$_2$Cl$_2$ (3×) and the combined organic layers were washed with brine (3×). The crude mixture was purified by chromatography on SiO$_2$ (EtOAc) to give product (1.93 g, 94%) as a white solid: HRMS (LCMS ESI+) m/z calcd for C$_{24}$H$_{17}$D$_9$N$_3$O$_3$ [M+H] 205.1335, found 205.1335.

B. 2-Cyclopentyl-N-(pyridin-3-yl)ethanethioamide

2-Cyclopentyl-N-(pyridin-3-yl)acetamide (1.00 g, 4.90 mmol) and 2,4-bis(4-phenoxyphenyl)-1,3-dithia-2,4-diphosphetane-2,4-disulfide (1.98 g, 2.90 mmol) were added to dry toluene and heated to reflux. Water (3.0 mL) was added and the reaction mixture was concentrated to yield a bright yellow oil. The oil was taken up in CH$_2$Cl$_2$ (50 mL) and absorbed on SiO$_2$ and purified by column chromatography on SiO$_2$ (70% EtOAc, 18% hexanes, and 12% TEA) to give product (0.820 g, 76%) as a light yellow solid: $^1$H NMR (CDCl$_3$, 300 MHz) 9.61 (s, 1H), 8.61 (d, J=2.4 Hz, 1H), 8.51-8.35 (m, 2H), 7.36 (dd, J=8.1, 5.0 Hz, 1H), 2.86 (d, J=7.4 Hz, 2H), 2.49 (appt. hept, J=7.7 Hz, 1H), 1.88 (tdd, J=11.8, 4.5, 2.4 Hz, 2H), 1.73-1.49 (m, 3H), 1.41-1.10 (m, 2H).

C. Methyl (Z)-2-cyclopentyl-N-(pyridin-3-yl)ethanimidothioate

To a solution of 2-cyclopentyl-N-(pyridin-3-yl)ethanethioamide (0.513 g, 2.328 mmol) in MeCN (15 mL), iodomethane (0.14 mL, 2.21 mmol) and cesium carbonate (0.758 g, 2.33 mmol) were added. The mixture was stirred at room temperature for 30 min and was diluted with H$_2$O, extracted with EtOAc (3×), washed with brine, dried (Na$_2$SO$_4$), filtered and concentrated. The residual oil was treated with hexanes and concentrated to give product (0.90 g, 87%) as a yellow oil: $^1$H NMR (CDCl$_3$, 300 MHz) 8.31 (dd, J=4.8, 1.5 Hz, 1H), 8.08 (s, 1H), 7.27-7.18 (m, 1H), 7.07 (d, J=8.1 Hz, 1H), 2.41-2.37 (m, 5H), 2.05-1.96 m, 1H), 1.74 (m, 2H), 1.50 (m, 4H), 1.01 (m, 2H).

D. (5-(Cyclopentylmethyl)-4-(pyridin-3-yl)-4H-1,2,4-triazol-3-yl)methanol

2-Cyclopentyl-N-(pyridin-3-yl)ethanethioamide (0.900 g, 3.65 mmol) and 2-((tetrahydro-2H-pyran-2-yl)oxy)acetohydrazide (0.662 g, 3.80 mmol) in DMF 9.0 mL was heated at 120° C. for 2 d, then cooled to room temperature. The reaction mixture was poured into H$_2$O, extracted with EtOAc (4×), washed with brine, dried (Na$_2$SO$_4$) filtered, and concentrated. The crude mixture was purified by chromatography on SiO$_2$ (0-10% MeOH/CH$_2$Cl$_2$) to give product (0.324 g, 34%) as an off-white solid: $^1$H NMR (CDCl$_3$, 300 MHz) 8.69 (dd, J=4.8, 1.5 Hz, 1H), 8.54 (d, J=2.5 Hz, 1H), 7.89 (s, 1H), 7.78 (ddd, J=8.2, 2.6, 1.5 Hz, 1H), 7.49 (ddd, J=8.1, 4.8, 0.8 Hz, 1H), 4.47 (s, 2H), 2.48 (d, J=7.5 Hz, 2H), 2.01 (apt. hept, J=7.7 Hz, 1H), 1.71-1.54 (m, 2H), 1.53-1.29 (m, 4H), 1.08-0.90 (m, 2H).

Example 13. (E)-3-(5-(((tert-butyldimethylsilyl)oxy)methyl)-2-(cyclopentylthio)-1-(pyridin-3-yl)-1H-imidazol-4-yl)acrylate

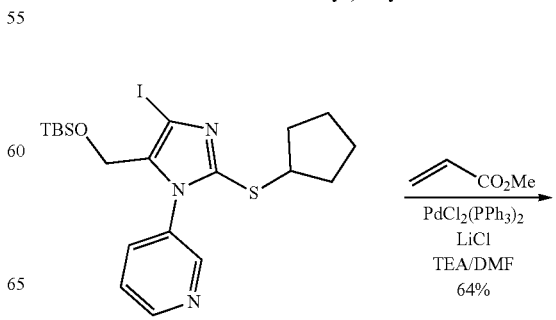

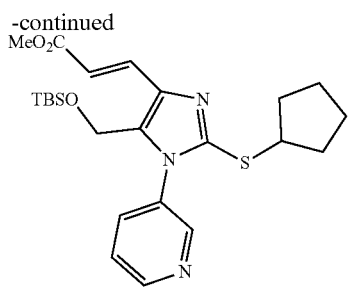

A solution of 3-(5-(((tert-butyldimethylsilyl)oxy)methyl)-2-(cyclopentylthio)-4-iodo-1H-imidazol-1-yl)pyridine (0.107 g, 0.207 mmol), LiCl (0.016 g, 0.37 mmol), PdCl$_2$(PPh$_3$)$_2$ (0.014 g, 0.020 mmol) was treated with DMF (1.2 mL). The solution was degassed with bubbling N2 for 10 min. To the solution was added methylacrylate (0.025 ml, 0.27 mmol) followed by TEA (0.050 mL, 0.35 mmol). The solution was degassed for 5 min, and the reaction vial was sealed and submerged into preheated oil bath at 50° C. The reaction mixture was heated at 90° C. overnight. The solution was cooled to room temperature, extracted with EtOAc, washed with brine (2x), dried (Na$_2$SO$_4$), filtered and concentrated. The residual oil was purified by chromatography on SiO$_2$ (ISCO-Rf, 0-100% EtOAc/hexanes) to give product (0.063 g, 64%) as a light yellow oil: IR (neat) 2951, 2929, 2357, 1712, 1637, 1483, 1460, 1427, 1300, 1254, 1161, 1056, 973, 937, 834, 775, 732, 707 685 cm$^{-1}$; $^1$H NMR (CDCl$_3$, 500 MHz) 8.71 (dd, J=1.5, 5.0 Hz, 1H), 8.60 (d, J=2.5 Hz, 1H), 7.70-7.68 (m, 1H), 7.60 (d, J=15.5 Hz, 1H), 7.43 (dd, J=5.0, 8.0 Hz, 1H), 6.72 (d, J=15.0 Hz, 1H), 4.48 (s, 2H), 3.91-3.88 (m, 1H), 3.79 (s, 3H), 2.15-2.10 (m, 2H), 1.69-1.61 (m, 2H), 1.60-1.56 (m, 4H), 0.79 (s, 9H), −0.15 (s, 6H); $^{13}$C NMR (CDCl$_3$, 125 MHz) 168.1, 150.3, 148.8, 146.9, 136.3, 135.5, 134.3, 133.7, 132.2, 123.6, 116.6, 53.2, 51.5, 46.4, 33.6, 25.7, 24.6, 18.0, −5.6; HRMS (LCMS ESI+) m/z calcd for C$_{24}$H$_{36}$N$_3$O$_3$SSi [M+H] 474.2241, found 474.2240.

Example 14. Methyl (E)-3-(2-(cyclopentylthio)-5-((4-(3-hydroxyprop-1-yn-1-yl)-3-methylphenoxy) methyl)-1-(pyridin-3-yl)-1H-imidazol-4-yl)acrylate

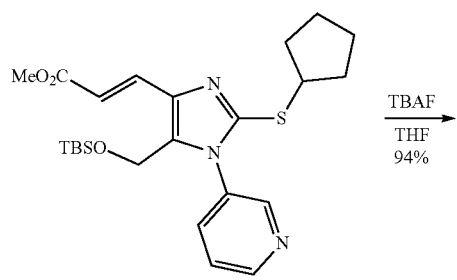

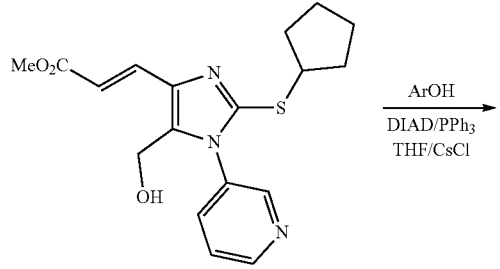

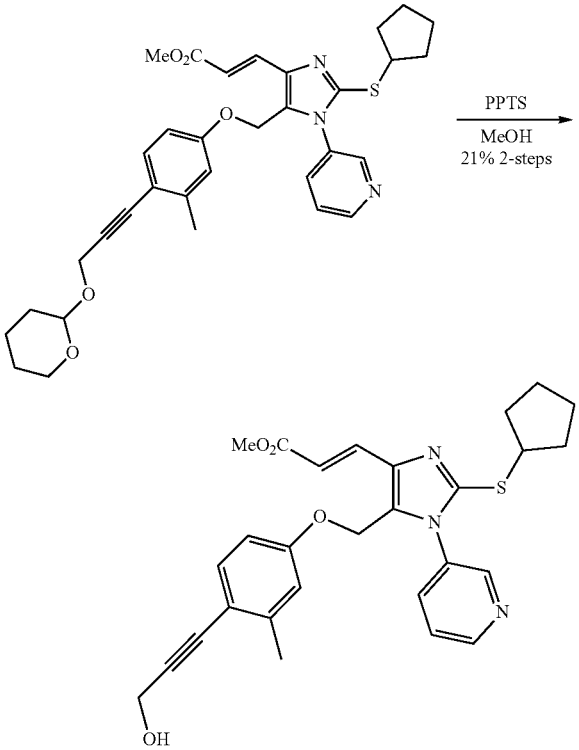

A. Methyl (E)-3-(2-(cyclopentylthio)-5-(hydroxymethyl)-1-(pyridin-3-yl)-1H-imidazol-4-yl)acrylate A solution of methyl (E)-3-(5-(((tert-butyldimethylsilyl)oxy)methyl)-2-(cyclopentylthio)-1-(pyridin-3-yl)-1H-imidazol-4-yl)acrylate (0.063 g, 0.13 mmol) in THF (2.0 mL) was cooled to 0° C. and treated with TBAF (0.15 mL, 1M THF). After 30 min, the reaction mixture was extracted with EtOAc, washed with brine (2x), dried (Na$_2$SO$_4$), filtered and concentrated. The solid residue was slurried with CH$_2$Cl2 and collected by filtration. The filtrate was concentrated and the residue was diluted with CH$_2$Cl$_2$ and the off-white solid was collected by filtration to give product (0.045 g, 94%) and was used without further purification: M.p. 168-169° C.; IR(neat) 3199, 2958, 2867, 1703, 1634, 1485, 1458, 1441, 1386, 1299, 1283, 1247, 1204, 1162, 1007, 993, 936, 866, 848, 812, 741, 707 cm$^{-1}$; $^1$H NMR (acetone-d$_6$, 500 MHz) 8.68 (d, J=4.6 Hz, 1H), 8.62 (d, J=2.2 Hz, 1H), 7.88 (d, J=8.1 Hz, 1H), 7.62 (d, J=15 Hz, 1H), 7.58-7.55 (m, 1H), 6.55 (d, J=15.3 Hz, 1H), 4.46 (d, J=5.7 Hz, 2H), 4.36 (t, J=5.5 Hz, 1H), 3.89 (t, J=6.5 Hz, 1H), 3.68 (s, 3H), 2.11-2.09 (m, 2H), 1.65-1.53 (m, 6H); $^{13}$C NMR (acetone-d$_6$, 100 MHz) 169.0, 152.3, 150.7, 148.0, 138.1, 137.9, 137.5, 136.3, 134.1, 125.9, 117.4, 53.5, 52.6, 47.9, 35.3, 26.3; HRMS (LCMS ESI+) m/z calcd for C$_{18}$H$_{22}$O$_3$N$_3$S [M+H] 360.1376, found 360.1379.

B. Methyl (E)-3-(2-(cyclopentylthio)-5-((3-methyl-4-(3-((tetrahydro-2H-pyran-2-yl)oxy)prop-1-yn-1-yl) phenoxy)methyl)-1-(pyridin-3-yl)-1H-imidazol-4-yl) acrylate To a solution of methyl (E)-3-(2-(cyclopentylthio)-5-(hydroxymethyl)-1-(pyridin-3-yl)-1H-imidazol-4-yl)acrylate (0.024 g, 0.067 mmol, crude), 3-methyl-4-(3-((tetrahydro- 2H-pyran-2-yl)oxy)prop-1-yn-1-yl)phenol (0.019 g, 0.077 mmol), PPh₃ (0.024 g, 0.090 mmol), CsCl (0.028 g, 0.16 mmol) in THF (1.5 mL) was added DIAD (0.030 mL, 0.15 mmol) at room temperature. After 18 h, the solution was extracted with EtOAc, washed with brine, dried (Na₂SO₄), filtered and concentrated. The residual oil was purified by chromatography on SiO₂ (ISCO-Rf, 0-100% EtOAc/hexanes) to give product (0.020 g, 45%) that was used without further purification: HRMS (LCMS ESI+) m/z calcd for $C_{33}H_{38}O_5N_3S$ [M+H] 588.2527, found 588.2527.

C. Methyl (E)-3-(2-(cyclopentylthio)-5-((4-(3-hydroxyprop-1-yn-1-yl)-3-methylphenoxy)methyl)-1-(pyridin-3-yl)-1H-imidazol-4-yl)acrylate To a solution of methyl (E)-3-(2-(cyclopentylthio)-5-((3-methyl-4-(3-((tetrahydro-2H-pyran-2-yl)oxy)prop-1-yn-1-yl)phenoxy)methyl)-1-(pyridin-3-yl)-1H-imidazol-4-yl)acrylate (0.020 g, 0.034 mmol) in MeOH (3.0 mL) was added PPTS (0.005 g, 0.020 mmol) at room temperature. The solution was heated at 40° C. for 2 h. The solution was treated with NaHCO₃ and concentrated. The residue was extracted with EtOAc, washed with satd. NaHCO₃, brine, dried (Na₂SO₄), filtered and concentrated. The residual oil was purified by chromatography on SiO₂ (ISCO-Rf, 0-100% EtOAc/hexanes) to give product (0.007 g, 21% 2-steps) as a light yellow oil: ¹H NMR (CDCl₃, 500 MHz) 8.69 (s, 1H), 8.64 (s, 1H), 7.70 (d, J=8.0 Hz, 1H), 7.60 (d, J=15.5 Hz, 1H), 7.41 (s, 1H), 7.26 (d, J=6.5 Hz, 1H), 6.79 (d, J=15.0 Hz, 1H), 6.61 (d, J=1.5 Hz, 1H), 6.54 (d, J=8.5 Hz, 1H), 4.80 (s, 2H), 4.50 (s, 2H), 3.98-3.95 (m, 1H), 3.79 (s, 3H), 2.35 (s, 3H), 2.19-2.16 (m, 2H), 1.71-1.57 (m, 6H); HRMS (LCMS ESI+) m/z calcd for $C_{28}H_{30}O_4N_3S$ [M+H] 504.1952, found 504.1952.

Example 15. 3-(4-((2-(Cyclopentylthio)-4-(2-hydroxypropan-2-yl)-1-(pyridin-3-yl)-1H-imidazol-5-yl)methoxy)-2-methylphenyl)prop-2-yn-1-ol

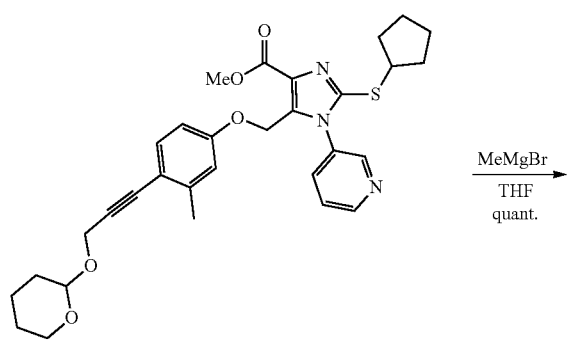

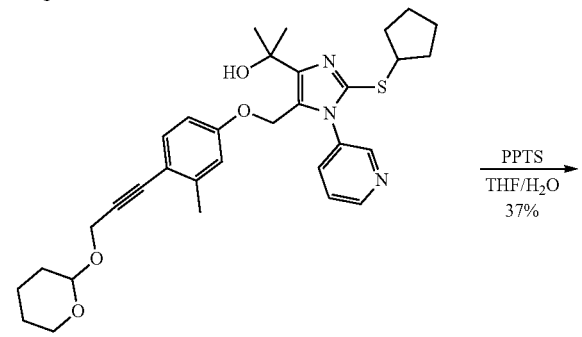

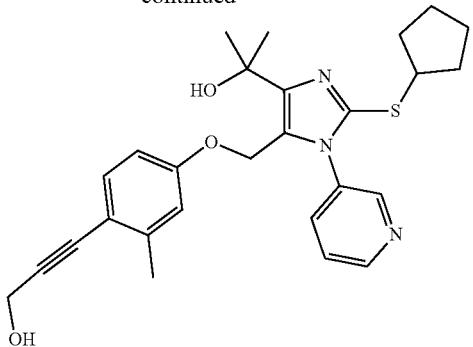

A. 2-(2-(Cyclopentylthio)-5-((3-methyl-4-(3-((tetrahydro-2H-pyran-2-yl)oxy)prop-1-yn-1-yl)phenoxy)methyl)-1-(pyridin-3-yl)-1H-imidazol-4-yl)propan-2-ol A solution of methyl 2-(cyclopentylthio)-5-((3-methyl-4-(3-((tetrahydro-2H-pyran-2-yl)oxy)prop-1-yn-1-yl)phenoxy)methyl)-1-(pyridin-3-yl)-1H-imidazole-4-carboxylate (0.035 g, 0.062 mmol) in THF (1.5 mL) was cooled to 0° C. and treated with MeMgBr (0.18 mL, 1.0M Et₂O-diluted from 3M solution) dropwise. After 2 h, the solution was quenched with brine, extracted with EtOAc (2×), dried (Na₂SO₄), filtered and concentrated to give product (0.035 g, quant.) as a light orange oil that was used without further purification: ¹H NMR (CDCl₃, 400 MHz) 8.64 (d, J=3.2 Hz, 1H), 8.61 (s, 1H), 7.70-7.67 (m, 1H), 7.39-7.37 (m, 1H), 7.28 (s, 1H), 6.62 (d, J=2.4 Hz, 1H), 6.54 (dd, J=2.4, 8.4 Hz, 1H), 4.90 (t, J=3.6 Hz, 1H), 4.84 (s, 2H), 4.49 (d, J=4.8 Hz, 2H), 3.88-3.85 (m, 1H), 3.78-3.74 (m, 1H), 3.56-3.53 (m, 1H), 2.35 (s, 3H), 2.04-2.02 (m, 2H), 1.79-1.55 (m, 3H), 1.53 (s, 6H), 1.52-1.50 (m, 7H); ¹³C NMR (CDCl₃, 100 MHz) 157.8, 150.1, 149.6, 148.9, 142.9, 142.3, 135.5, 133.5, 132.2, 123.7, 123.1, 115.7, 115.6, 112.0, 96.6, 87.7, 84.3, 71.0, 62.1, 59.4, 54.8, 47.0, 33.5, 31.1, 30.3, 25.4, 24.5, 20.9, 19.1; HRMS (LCMS ESI+) m/z calcd for $C_{32}H_{40}O_4N_3S$ [M+H] 562.2734, found 562.2735.

B. 3-(4-((2-(Cyclopentylthio)-4-(2-hydroxypropan-2-yl)-1-(pyridin-3-yl)-1H-imidazol-5-yl)methoxy)-2-methylphenyl)prop-2-yn-1-ol To a solution of 2-(2-(cyclopentylthio)-5-((3-methyl-4-(3-((tetrahydro-2H-pyran-2-yl)oxy)prop-1-yn-1-yl)phenoxy)methyl)-1-(pyridin-3-yl)-1H-imidazol-4-yl)propan-2-ol (0.035 g, 0.062 mmol) in THF (1.0 mL) was added H₂O (0.2 mL) followed by PPTS (0.016 g, 0.063 mmol) at room temperature. After 20 h, the reaction was heated to reflux for 2 h. The solution was extracted with EtOAc, washed with satd. NaHCO₃, brine, dried (Na₂SO₄), filtered and concentrated. The residue was purified by chromatography on SiO₂ (ISCO-Rf, 0-100% EtOAc/hexanes) to give product as an off-white solid (0.011 g, 37%): M.p. 119-121° C.; IR (neat) 3326, 2966, 1602, 1495, 1430, 1376, 1232, 1164, 1034, 956, 842, 826, 726, 709 cm⁻¹; ¹H NMR (CDCl₃, 500 MHz) 8.65 (d, J=3.9 Hz, 1H), 8.61 (d, J=2.1 Hz, 1H), 7.69 (dd, J=1.9, 6.5 Hz, 1H), 7.38 (dd, J=4.8, 4.8 Hz, 1H), 7.25 (d, J=8.5 Hz, 1H), 6.62 (d, J=2.2 Hz, 1H), 6.55 (dd, J=2.4, 8.5 Hz, 1H), 4.85 (s, 2H), 4.49 (s, 2H), 3.76 (pent, J=6.7 Hz, 1H), 2.34 (s, 3H), 2.05-1.98 (m, 3H), 1.68-1.56 (m, 2H), 1.55 (s, 6H), 1.54-1.51 (m, 5H); ¹³C NMR (CDCl₃, 100 MHz) 157.9, 150.2, 149.7, 148.9, 143.0, 142.2, 135.6, 133.4, 132.2, 123.7, 123.1, 115.8, 115.4, 112.0, 89.9, 84.2, 71.1, 59.4, 51.7, 47.0, 33.6, 31.1, 24.6, 20.9; HRMS (LCMS ESI+) m/z calcd for $C_{27}H_{32}O_3N_3S$ [M+H] 478.2159, found 478.2158; ELS purity (98%).

Example 16. Assay Methods

The BioMol Green ATPase assay procedure used was that which was disclosed in Zhang, et al., "Altered cofactor regulation with disease-associated p97/VCP mutations," Proc. Natl. Acad. Sci. USA, 112(14), E1705-E1714 (2015). The following Table IV provides relevant results. The compound number correlates to the numbered compounds in Table 111. Compounds also show activity in a cell-based assay such as the ubiquitin assay (assay as described in, e.g., (1) Dantuma et al., "Short-lived green fluorescent proteins for quantifying ubiquitin/proteasome-dependent proteolysis in living cells," Nat. Biotechnol. 2000, 18, 538-543; and (2) WO 2010003908).

TABLE IV

| No | P97 Biomolgreen; 200 µM ATP; $IC_{50}$ (µM); |
|---|---|
| 1 | 0.037 |
| 2 | 0.034 |
| 3 | 0.039 |
| 4 | 0.036 |
| 5 | 0.10 |
| 6 | 0.1 |
| 7 | 0.11 |
| 8 | 0.06 |
| 9 | 0.056 |
| 10 | 0.05 |
| 11 | 0.02 |
| 12 | 0.05 |
| 13 | 0.032 |
| 14 | 0.027 |
| 15 | 0.014 |
| 16 | >6.7 |
| 17 | 0.24 |
| 18 | 0.034 |
| 19 | 0.057 |
| 20 | 0.029 |
| 21 | 0.017 |
| 22 | 0.06 |
| 23 | 0.03 |
| 24 | 0.05 |
| 25 | 0.05 |
| 26 | 0.05 |
| 27 | 0.11 |
| 28 | 0.25 |
| 29 | 0.075 |
| 30 | 0.066 |
| 31 | 0.054 |
| 32 | 0.037 |
| 33 | 0.13 |
| 34 | 0.16 |
| 35 | 0.008 |
| 36 | 0.011 |
| 37 | 0.017 |
| 38 | 0.019 |
| 39 | 0.019 |
| 40 | 0.020 |
| 41 | 0.040 |
| 42 | 0.046 |
| 43 | 0.056 |
| 44 | 0.060 |
| 45 | 0.20 |

Paragraph A. A compound having a structure of Formula (I):

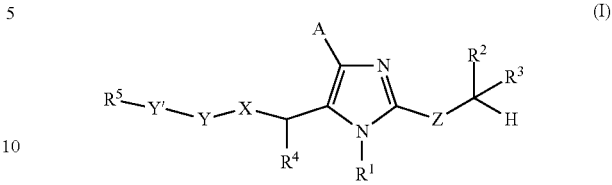

or a pharmaceutically acceptable salt, solvate, or prodrug thereof, wherein:

X is O, $SO_{0-2}$, NR or $C(R^7)_2$;

Y is optionally substituted aryl, optionally substituted alkyl, optionally substituted alkenyl, alkynyl, optionally substituted heteroaryl, optionally substituted cycloalkyl, or optionally substituted non-aromatic heterocyclyl;

Y' is alkynyl, optionally substituted aryl, optionally substituted heteroaryl, optionally substituted cycloalkyl, optionally substituted non-aromatic heterocyclyl, or a bond;

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

Z is O, $SO_{0-2}$, NR, $C(R^7)_2$, alkenyl or alkynyl;

$R^1$ is optionally substituted phenyl, optionally substituted 5- or 6-membered heteroaryl, or optionally substituted non-aromatic heterocyclic;

$R^4$ is H, $C(R^7)_2$, aryl, or heteroaryl;

$R^5$ is H, nitrile, an optionally substituted aryl, an optionally substituted heterocycle, optionally substituted $C_1$-$C_6$ alkyl, optionally substituted $C_3$-$C_9$ cycloalkyl, or

where

R' and R" are each independently selected from the group consisting of H, optionally substituted alkyl, —OR, halogen, —N(R)$_2$, optionally substituted cycloalkyl, and optionally substituted heterocyclyl;

or R' and R" may together form an optionally substituted 3- to 6-membered cycloalkyl or optionally substituted 3- to 6-membered non-aromatic heterocycle;

D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;

E' is selected from the group consisting of a bond, an optionally substituted $C_1$-$C_6$ alkyl, optionally substituted $C_1$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted $C_1$-$C_6$ alkyl, and optionally substituted cycloalkyl;

$R^7$ is independently selected from the group consisting of H, halogen, optionally substituted $C_1$-$C_6$ alkyl, optionally substituted cycloalkyl, —OR, and —N(R); and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

Paragraph B. A compound having a structure of Formula (Ia):

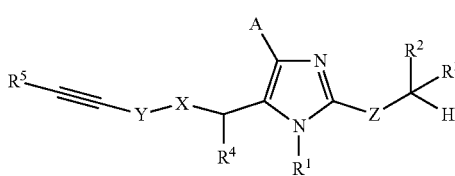

(Ia)

or a pharmaceutically acceptable salt, solvate, or prodrug thereof, wherein:

X is O, SO$_{0-2}$, NR, or C(R$^7$)$_2$;

Y is optionally substituted aryl, optionally substituted alkyl, optionally substituted alkenyl, alkynyl, optionally substituted heteroaryl, optionally substituted cycloalkyl, or optionally substituted non-aromatic heterocyclyl;

R$^2$ and R$^3$ are independently H, optionally substituted C$_{1-6}$ alkyl, optionally substituted C$_{1-9}$ cyclic, optionally substituted C$_{3-9}$ heterocyclyl, or halogen, or R$^2$ and R$^3$ together form an optionally substituted C$_{3-9}$ cyclic or optionally substituted 3- to 9-membered heterocyclyl ring;

Z is O, SO$_{0-2}$, NR, C(R$^7$)$_2$, alkenyl or alkynyl;

R$^1$ is optionally substituted phenyl, optionally substituted 5- or 6-membered heteroaryl, or optionally substituted non-aromatic heterocyclic;

R$^4$ is H, C(R$^7$)$_2$, aryl, or heteroaryl;

R$^5$ is H, nitrile, an optionally substituted aryl, an optionally substituted heterocycle, optionally substituted C$_1$-C$_6$ alkyl, optionally substituted C$_3$-C$_9$ cycloalkyl, or

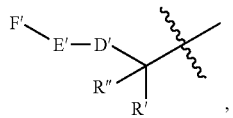

where

R' and R" are each independently selected from the group consisting of H, optionally substituted alkyl, —OR, halogen, —N(R)$_2$, optionally substituted cycloalkyl, and optionally substituted heterocyclyl;

or R' and R" may together form an optionally substituted 3- to 6-membered cycloalkyl or optionally substituted 3- to 6-membered non-aromatic heterocycle;

D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;

E' is selected from the group consisting of a bond, an optionally substituted C$_1$-C$_6$ alkyl, optionally substituted C$_1$-C$_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted C$_1$-C$_6$ alkyl, and optionally substituted cycloalkyl;

R$^7$ is independently selected from the group consisting of H, halogen, optionally substituted C$_1$-C$_6$ alkyl, optionally substituted cycloalkyl, —OR, and —N(R); and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

Paragraph C. A compound having a structure of Formula (Ib):

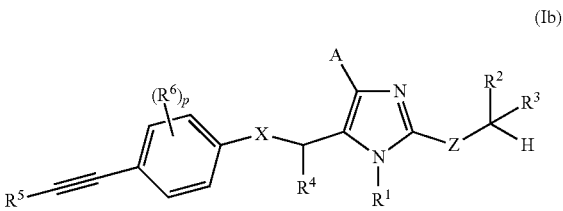

(Ib)

or a pharmaceutically acceptable salt, solvate, or prodrug thereof, wherein:

X is O, SO$_{0-2}$, or NR;

R$^2$ and R$^3$ are independently H, optionally substituted C$_{1-6}$ alkyl, optionally substituted C$_{1-9}$ cyclic, optionally substituted C$_{3-9}$ heterocyclyl, or halogen, or R$^2$ and R$^3$ together form an optionally substituted C$_{3-9}$ cyclic or optionally substituted 3- to 9-membered heterocyclyl ring;

Z is O, SO$_{0-2}$, NR, C(R$^7$)$_2$, alkenyl or alkynyl;

R$^1$ is optionally substituted phenyl, optionally substituted 5- or 6-membered heteroaryl, or optionally substituted non-aromatic heterocyclic;

R$^4$ is H, C(R$^7$)$_2$, aryl, or heteroaryl;

R$^5$ is H, nitrile, an optionally substituted aryl, an optionally substituted heterocycle, optionally substituted C$_1$-C$_6$ alkyl, optionally substituted C$_3$-C$_9$ cycloalkyl, or

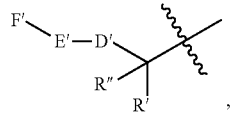

where

R' and R" are each independently selected from the group consisting of H, optionally substituted alkyl, —OR, halogen, —N(R)$_2$, optionally substituted cycloalkyl, and optionally substituted heterocyclyl;

or R' and R" may together form an optionally substituted 3- to 6-membered cycloalkyl or optionally substituted 3- to 6-membered non-aromatic heterocycle;

D' is selected from the group consisting of —O—, —NR—, —OCONR—, —OCO—, —NRSO$_2$—, —NRCO—, —NRSO₂NR—, —NRCOO—, —NR-CONR—, and —NRC(NR)NR—;

E' is selected from the group consisting of a bond, an optionally substituted C₁-C₆ alkyl, optionally substituted C₁-C₆ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted C₁-C₆ alkyl, and optionally substituted cycloalkyl;

R⁶ is independently selected from the group consisting of alkyl, —CF₃, —OR, —CN, —CO₂R, halogen, —SR, —SOR, —SO₂R, —SF₅, and —NR₂;

p is 0, 1, or 2;

R⁷ is independently selected from the group consisting of H, halogen, optionally substituted C₁-C₆ alkyl, optionally substituted cycloalkyl, —OR, and —N(R); and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)₂, or —COOR;

provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

Paragraph D. A compound having a structure of Formula (Ic):

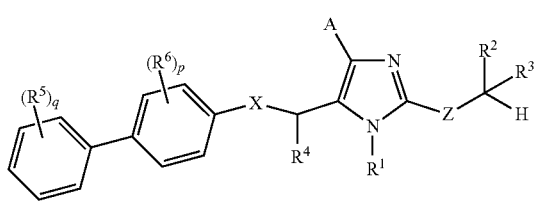

(Ic)

or a pharmaceutically acceptable salt, solvate, or prodrug thereof, wherein:

X is O, SO₀₋₂, or NR;

R² and R³ are independently H, optionally substituted C₁₋₆ alkyl, optionally substituted C₁₋₉ cyclic, optionally substituted C₃₋₉ heterocyclyl, or halogen, or R² and R³ together form an optionally substituted C₃₋₉ cyclic or optionally substituted 3- to 9-membered heterocyclyl ring;

Z is O, SO₀₋₂, NR, C(R⁷)₂, alkenyl or alkynyl;

R¹ is optionally substituted phenyl, optionally substituted 5- or 6-membered heteroaryl, or optionally substituted non-aromatic heterocyclic;

R⁴ is H, C(R⁷)₂, aryl, or heteroaryl;

R⁵ is independently selected from the group consisting of NO₂, optionally substituted alkynyl, optionally substituted alkenyl, C₁₋₆ alkyl, —CF₃, —OR, —CN, —CO₂R, halogen, —SR, —SOR, —SO₂R, —SF₅, and —NR₂;

R⁶ is independently selected from the group consisting of NO₂, optionally substituted alkynyl, optionally substituted alkenyl, alkyl, —CF₃, —OR, —CN, —CO₂R, halogen, —SR, —SOR, —SO₂R, —SF₅, and —NR₂;

p is 0, 1, or 2;

q is 0, 1, 2, 3, 4, or 5;

R is independently selected from the group consisting of H, optionally substituted C₁-C₆ alkyl, and optionally substituted cycloalkyl;

R⁷ is independently selected from the group consisting of H, halogen, optionally substituted C₁-C₆ alkyl, optionally substituted cycloalkyl, —OR, and —N(R)₂; and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)₂, or —COOR.

Paragraph E. The compound of any one of Paras. A-D, wherein X is O or S.

Paragraph F. The compound of Paragraph A or Paragraph B, wherein Y is selected from the group consisting of:

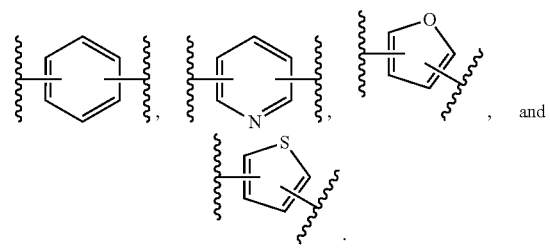

and

Paragraph G. The compound of Paragraph A or Paragraph B, wherein Y is phenylene optionally substituted with C₁-C₆ alkyl, cycloalkyl, —CF₃, —OR, —CN, —CO₂R, halogen, —SR, —SOR, —SO₂R, —SF₅, or —NR₂, or a combination of two or more thereof.

Paragraph H. The compound of Paragraph A, wherein Y' is a bond, alkynyl, or optionally substituted aryl.

Paragraph I. The compound of Paragraph A, wherein Y' is a bond, alkynyl, or phenylene optionally substituted with alkyl, —CF₃, —OR, —CN, —CO₂R, halogen, —SR, —SOR, —SO₂R, —SF₅, or —NR₂, or a combination of two or more thereof.

Paragraph J. The compound of any one of Paras. A-D, wherein Z is selected from the group consisting of O, S and CH₂.

Paragraph K. The compound of any one of Paras. A-C, wherein R⁵ is a phenyl optionally substituted with one or more alkyl, —OR, —CN, —CO₂R, halogen, —SR, —SOR, —SO₂R, —SF₅, and —NR₂, or any combination thereof.

Paragraph L. The compound of any one of Paras. A-C, wherein R⁵ is a heterocycle optionally substituted with alkyl, —OR, —CN, —CO₂R, halogen, —SR, —SOR, —SO₂R, —SF₅ or —NR₂, or a combination of two or more thereof.

Paragraph M. The compound of any one of Paras. A-C, wherein R⁵ is

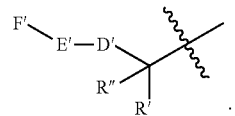

Paragraph N. The compound of Paragraph M, wherein R' and R" together form a 3- to 6-membered cycloalkyl or 3- to 6-membered non-aromatic heterocycle.

Paragraph O. The compound of Paragraph M, wherein R' and R" are each H, or at least one of R' and R" is methyl and any remaining R' or R" is H.

Paragraph P. The compound of Paragraph M, wherein at least one of R' and R" is an optionally substituted alkyl.

Paragraph Q. The compound of any one of Paras. M-P, wherein E' is a $C_1$-$C_6$ alkyl and F' is H.

Paragraph R. The compound of any one of Paras. M-P, wherein F' is an optionally substituted cycloalkyl selected from: cyclopropyl, cyclobutyl, cyclopentyl, and cyclohexyl.

Paragraph S. The compound of any one of Paras. M-P, wherein F' is an optionally substituted heterocycle selected from: morpholine, azetidine, alkyl-piperidine, alkyl-piperazine, alkyl-diazepane, thiomorpholine 1,1-dioxide, isoindoline-1,3-dione, tetrahydropyran, and pyrrolidone.

Paragraph T. The compound of any one of Paras. M-P, wherein F' is an optionally substituted aryl selected from: phenyl, optionally substituted with alkyl, —$CF_3$, —OR, —CN, —$CO_2R$, halogen, —SR, —SOR, —$SO_2R$, —$SF_5$ or —$NR_2$, or a combination of two or more thereof.

Paragraph U. The compound of any one of Paras. M-P, wherein F' is an optionally substituted heteroaryl selected from: alkyl-triazole, tetrazole, imidazole, and isoxazole.

Paragraph V. The compound of any one of Paras. M-U, wherein D' is —O—, —NH—, —OCONH—, —OCO—, —NHCO—, or —NHCOO—.

Paragraph W. The compound of any one of Paras. A-D, wherein $R^1$ is optionally substituted pyridine.

Paragraph X. A compound of Formula (IIa):

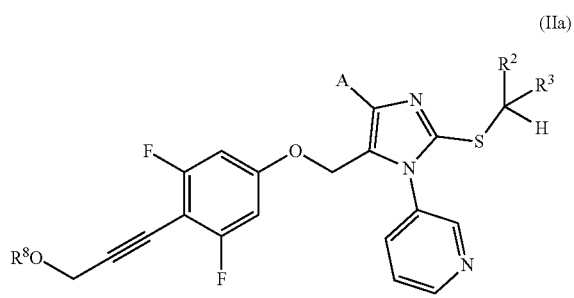

(IIa)

or a pharmaceutically acceptable salt, solvate, or prodrug thereof, wherein:

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

R is independently selected from the group consisting of H, optionally substituted $C_1$-$C_6$ alkyl, and optionally substituted cycloalkyl; and $R^8$ is selected from the group consisting of H,

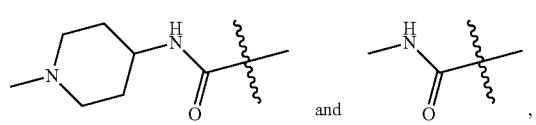

and wherein ⸰ indicates a point of attachment to O.

Paragraph Y. A compound of Formula (IIb):

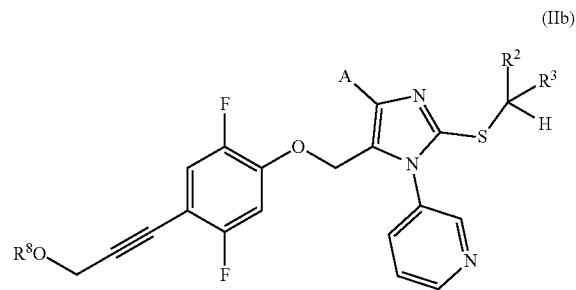

(IIb)

or a pharmaceutically acceptable salt, solvate, or prodrug thereof, wherein:

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

R is independently selected from the group consisting of H, optionally substituted $C_1$-$C_6$ alkyl, and optionally substituted cycloalkyl; and $R^8$ is selected from the group consisting of H,

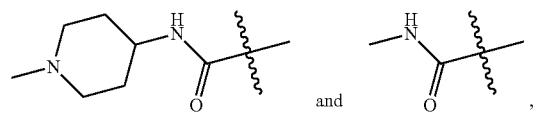

wherein ⸰ indicates a point of attachment to O.

Paragraph Z. The compound of any one of Paras. A-D, X and Y, wherein $R^2$ and $R^3$ together form a cyclopropyl, cyclopentyl or cyclohexene.

Paragraph AA. The compound of any one of Paras. A-D, X and Y, wherein $R^2$ and $R^3$ are independently optionally substituted $C_{1-6}$ alkyl.

Paragraph AB. The compound of any one of Paras. A-D, X and Y, wherein A is H, halogen, nitrile, optionally substituted alkyl, optionally substituted alkenyl, optionally substituted alkynyl, —CON(R)$_2$, or —COOR.

Paragraph AC. The compound of any one of Paras. A-D, X and Y, wherein A is H.

Paragraph AD. A compound of Formula (III):

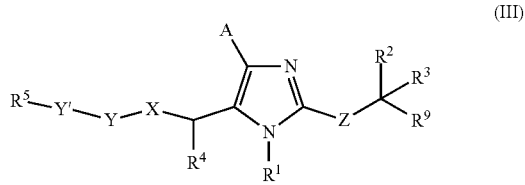

(III)

or a pharmaceutically acceptable salt, solvate, or prodrug thereof, wherein:

X is O, $SO_{0-2}$, NR, or $C(R^7)_2$;

Y is optionally substituted aryl, optionally substituted alkyl, optionally substituted alkenyl, alkynyl, optionally substituted heteroaryl, optionally substituted cycloalkyl, or optionally substituted non-aromatic heterocyclyl;

Y' is alkynyl, optionally substituted aryl, optionally substituted heteroaryl, optionally substituted cycloalkyl, optionally substituted non-aromatic heterocyclyl, or a bond;

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

Z is O, $SO_{0-2}$, NR, $C(R^7)_2$, alkenyl or alkynyl;

$R^1$ is optionally substituted phenyl, optionally substituted 5- or 6-membered heteroaryl, or optionally substituted non-aromatic heterocyclic;

$R^4$ is H, $C(R^7)_2$, aryl, or heteroaryl;

$R^5$ is H, nitrile, an optionally substituted aryl, an optionally substituted heterocycle, optionally substituted $C_1$-$C_6$ alkyl, optionally substituted $C_3$-$C_9$ cycloalkyl, or

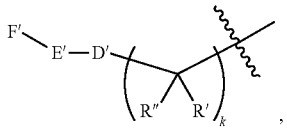

where k is 1, 2, 3, 4, or 5; R' and R" are each independently selected from the group consisting of H, optionally substituted alkyl, —OR, halogen (e.g., F, Cl, Br, I), —N(R)$_2$, optionally substituted cycloalkyl, and optionally substituted heterocyclyl;

or R' and R" may together form an optionally substituted 3- to 6-membered cycloalkyl or optionally substituted 3- to 6-membered non-aromatic heterocycle;

D' is selected from the group consisting of —O—, —NR—, —OCONR—, —OCO—, —CO—, —CO(NR)—, —$SO_{0-2}$—, —$SO_{0-2}$NR—, —NRSO$_2$—, —NRCO—, —NRSO$_2$NR—, —NRCOO—, —NRCONR—, and —NRC(NR)NR—;

E' is selected from the group consisting of a bond, an optionally substituted $C_1$-$C_6$ alkyl, optionally substituted $C_1$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted $C_1$-$C_6$ alkyl, and optionally substituted cycloalkyl;

$R^7$ is independently selected from the group consisting of H, halogen, optionally substituted $C_1$-$C_6$ alkyl, optionally substituted cycloalkyl, —OR, and —N(R); and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

$R^9$ is H, nitrile, halogen, —C(O)(optionally substituted alkyl), optionally substituted heterocycle, optionally substituted cyclic ring, or optionally substituted alkyl;

provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

Paragraph AE. The compound of Paragraph AD, wherein X is O or S.

Paragraph AF. The compound of Paragraph AD or Paragraph AE, wherein Y is selected from the group consisting of:

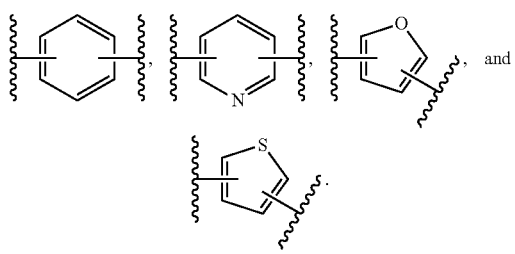

Paragraph AG. The compound of Paragraph AD or Paragraph AE, wherein Y is phenylene optionally substituted with $C_1$-$C_6$ alkyl, cycloalkyl, —CF$_3$, —OR, —CN, —CO$_2$R, halogen, —SR, —SOR, —SO$_2$R, —SF$_5$, or —NR$_2$, or a combination of two or more thereof.

Paragraph AH. The compound of any of Paras. AD-AG, wherein Y' is a bond, alkynyl, or optionally substituted aryl.

Paragraph AI. The compound of any of Paras. AD-AH, wherein Y' is a bond, alkynyl, or phenylene optionally substituted with alkyl, —CF$_3$, —OR, —CN, —CO$_2$R, halogen, —SR, —SOR, —SO$_2$R, —SF$_5$, or —NR$_2$, or a combination of two or more thereof.

Paragraph AJ. The compound of any of Paras. AD-AI, wherein Z is selected from the group consisting of O, S and CH$_2$.

Paragraph AK. The compound of any of Paras. AD-AJ, wherein $R^5$ is a phenyl optionally substituted with one or more alkyl, —OR, —CN, —CO$_2$R, halogen, —SR, —SOR, —SO$_2$R, —SF$_5$, and —NR$_2$, or any combination thereof.

Paragraph AL. The compound of any of Paras. AD-AJ, wherein $R^5$ is a heterocycle optionally substituted with alkyl, —OR, —CN, —CO$_2$R, halogen, —SR, —SOR, —SO$_2$R, —SF$_5$ or —NR$_2$, or a combination of two or more thereof.

Paragraph AM. The compound of any of Paras. AD-AJ, wherein $R^5$ is

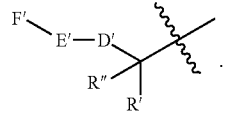

Paragraph AN. The compound of Paragraph AM, wherein R' and R" together form a 3- to 6-membered cycloalkyl or 3- to 6-membered non-aromatic heterocycle.

Paragraph AO. The compound of Paragraph AM, wherein R' and R" are each H, or at least one of R' and R" is methyl and any remaining R' or R" is H.

Paragraph AP. The compound of Paragraph AM, wherein at least one of R' and R" is an optionally substituted alkyl.

Paragraph AQ. The compound of any one of Paras. AM-AP, wherein E' is a $C_1$-$C_6$ alkyl and F' is H.

Paragraph AR. The compound of any one of Paras. AM-AP, wherein F' is an optionally substituted cycloalkyl selected from: cyclopropyl, cyclobutyl, cyclopentyl, and cyclohexyl.

Paragraph AS. The compound of any one of Paras. AM-AP, wherein F' is an optionally substituted heterocycle selected from: morpholine, azetidine, alkyl-piperidine, alkyl-piperazine, alkyl-diazepane, thiomorpholine 1,1-dioxide, isoindoline-1,3-dione, tetrahydropyran, and pyrrolidone.

Paragraph AT. The compound of any one of Paras. AM-AP, wherein F' is an optionally substituted aryl selected from: phenyl, optionally substituted with alkyl, —$CF_3$, —OR, —CN, —$CO_2R$, halogen, —SR, —SOR, —$SO_2R$, —$SF_5$ or —$NR_2$, or a combination of two or more thereof.

Paragraph AU. The compound of any one of Paras. AM-AP, wherein F' is an optionally substituted heteroaryl selected from: alkyl-triazole, tetrazole, imidazole, and isoxazole.

Paragraph AV. The compound of any one of Paras. AM-AU, wherein D' is —O—, —NH—, —OCONH—, —OCO—, —NHCO—, or —NHCOO—.

Paragraph AW. The compound of any one of Paras. AD-AV, wherein $R^1$ is optionally substituted pyridine Paragraph AX. The compound of any one of Paras. AD-AW, wherein $R^2$ and $R^3$ together form a cyclopropyl, cyclopentyl or cyclohexene.

Paragraph AY. The compound of any one of Paras. AD-AW, wherein $R^2$ and $R^3$ are independently optionally substituted $C_{1-6}$ alkyl.

Paragraph AZ. The compound of any one of Paras. AD-AY, wherein A is H, halogen, nitrile, optionally substituted alkyl, optionally substituted alkenyl, optionally substituted alkynyl, —$CON(R)_2$, or —COOR.

Paragraph BA. The compound of any one of Paras. AD-AZ, wherein A is H.

Paragraph BB. A compound selected from Table III or a pharmaceutically acceptable salt, solvate, or prodrug thereof.

Paragraph BC. A pharmaceutical composition comprising a compound of any one of Paras. A-BB and at least one pharmaceutically acceptable excipient.

Paragraph BD. A method of inhibiting p97 in a subject in need thereof, comprising administering to the subject a therapeutically effective amount of a compound of any one of Paras. A-BB or a therapeutically effective amount of a pharmaceutical composition of Paragraph BC.

Paragraph BE. A method of modulating p97 in a subject in need thereof, comprising administering to the subject a therapeutically effective amount of a compound of any one of Paras. A-BB or a therapeutically effective amount of a pharmaceutical composition of Paragraph BC.

Paragraph BF. A method of treating cancer or a neurodegenerative disease susceptible to treatment by p97 inhibition in a subject in need thereof comprising administering to the subject a therapeutically effective amount of a compound of any one of Paras. A-BB or a therapeutically effective amount of a pharmaceutical composition of Paragraph BC.

Paragraph BG. The method of Paragraph BF, wherein the method is a method of treating cancer susceptible to treatment by p97 inhibition, and wherein the cancer is selected from the group consisting of a solid tumor, non-small cell lung carcinoma, multiple myeloma, and mantle cell lymphoma.

Paragraph BH. The method of Paragraph BF, wherein the method is a method of treating a neurodegenerative disease susceptible to treatment by p97 inhibition, and wherein the neurodegenerative disease is selected from the group consisting of inclusion body myopathy (IBM), Paget's disease of the bone (PDB), frontotemporal dementia (FTD) and amyotrophic lateral sclerosis (ALS).

Paragraph BI. A method of treating cancer or a neurodegenerative disease susceptible to treatment by p97 modulation in a subject in need thereof comprising administering to the subject a therapeutically effective amount of a compound of any one of Paras. A-BB or a therapeutically effective amount of a pharmaceutical composition of Paragraph BC.

Paragraph BJ. The method of Paragraph BI, wherein the method is a method of treating cancer susceptible to treatment by p97 modulation, and wherein the cancer is selected from the group consisting of a solid tumor, non-small cell lung carcinoma, multiple myeloma, and mantle cell lymphoma.

Paragraph BK. The method of Paragraph BI, wherein the method is a method of treating a neurodegenerative disease susceptible to treatment by p97 modulation, and wherein the neurodegenerative disease is selected from the group consisting of inclusion body myopathy (IBM), Paget's disease of the bone (PDB), frontotemporal dementia (FTD) and amyotrophic lateral sclerosis (ALS).

Paragraph BL. A method of treating antibacterial and/or antiviral infection in a subject in need thereof comprising administering to the subject a therapeutically effective amount of a compound of any one of Paras. A-BB or a therapeutically effective amount of a pharmaceutical composition of Paragraph BC.

The invention claimed is:
1. A compound having a structure of Formula (I):

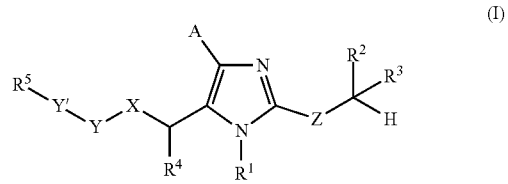

or a pharmaceutically acceptable salt, solvate, or prodrug thereof, wherein:
  X is O, $SO_{0-2}$, or $C(R^7)_2$;
  Y is optionally substituted aryl, optionally substituted alkenyl, alkynyl, optionally substituted heteroaryl, optionally substituted cycloalkyl, or optionally substituted non-aromatic heterocyclyl;
  Y' is alkynyl, optionally substituted aryl, optionally substituted heteroaryl, optionally substituted cycloalkyl, optionally substituted non-aromatic heterocyclyl, or a bond;
  $R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;
  Z is O, $SO_{0-2}$, NR, $C(R^7)_2$, alkenyl or alkynyl;
  $R^1$ is optionally substituted phenyl, optionally substituted 5- or 6-membered heteroaryl, or optionally substituted non-aromatic heterocyclic;
  $R^4$ is H, $C(R^7)_2$, aryl, or heteroaryl;

$R^5$ is

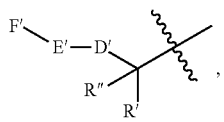

where
R' and R" are each independently selected from the group consisting of H, optionally substituted alkyl, —OR, halogen, —N(R)$_2$, optionally substituted cycloalkyl, and optionally substituted heterocyclyl;
or R' and R" may together form an optionally substituted 3- to 6-membered cycloalkyl or optionally substituted 3- to 6-membered non-aromatic heterocycle;
D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;
E' is selected from the group consisting of a bond, an optionally substituted $C_1$-$C_6$ alkyl, optionally substituted $C_1$-$C_6$ alkenyl, and optionally substituted cycloalkyl; and
F' is selected from the group consisting of H, an optionally substituted cycloalkyl, an optionally substituted non-aromatic heterocycle, an optionally substituted aryl, and an optionally substituted heteroaryl;
R is independently selected from the group consisting of H, optionally substituted $C_1$-$C_6$ alkyl, and optionally substituted cycloalkyl;
$R^7$ is independently selected from the group consisting of H, halogen, optionally substituted $C_1$-$C_6$ alkyl, optionally substituted cycloalkyl, —OR, and —N(R); and
A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;
provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

2. A compound having a structure of Formula (Ia):

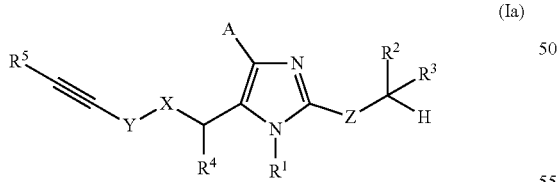

or a pharmaceutically acceptable salt, solvate, or prodrug thereof, wherein:
X is O, SO$_{0-2}$, NR, or C(R$^7$)$_2$;
Y is optionally substituted aryl, optionally substituted alkyl, optionally substituted alkenyl, alkynyl, optionally substituted heteroaryl, optionally substituted cycloalkyl, or optionally substituted non-aromatic heterocyclyl;
$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;
Z is O, SO$_{0-2}$, NR, C(R$^7$)$_2$, alkenyl or alkynyl;
$R^1$ is optionally substituted phenyl, optionally substituted 5- or 6-membered heteroaryl, or optionally substituted non-aromatic heterocyclic;
$R^4$ is H, C(R$^7$)$_2$, aryl, or heteroaryl;
$R^5$ is H, nitrile, an optionally substituted aryl, an optionally substituted heterocycle, optionally substituted $C_1$-$C_6$ alkyl, optionally substituted $C_3$-$C_9$ cycloalkyl, or

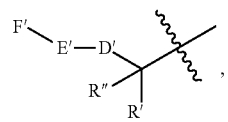

where
R' and R" are each independently selected from the group consisting of H, optionally substituted alkyl, —OR, halogen, —N(R)$_2$, optionally substituted cycloalkyl, and optionally substituted heterocyclyl;
or R' and R" may together form an optionally substituted 3- to 6-membered cycloalkyl or optionally substituted 3- to 6-membered non-aromatic heterocycle;
D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;
E' is selected from the group consisting of a bond, an optionally substituted $C_1$-$C_6$ alkyl, optionally substituted $C_1$-$C_6$ alkenyl, and optionally substituted cycloalkyl; and
F' is selected from the group consisting of H, an optionally substituted cycloalkyl, an optionally substituted non-aromatic heterocycle, an optionally substituted aryl, and an optionally substituted heteroaryl;
R is independently selected from the group consisting of H, optionally substituted $C_1$-$C_6$ alkyl, and optionally substituted cycloalkyl;
$R^7$ is independently selected from the group consisting of H, halogen, optionally substituted $C_1$-$C_6$ alkyl, optionally substituted cycloalkyl, —OR, and —N(R); and
A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;
provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

3. A compound having a structure of Formula (Ib):

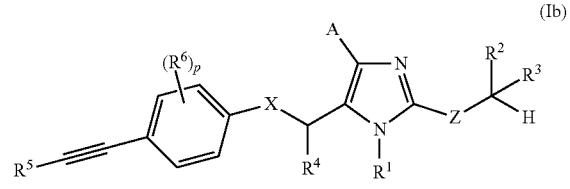

or a pharmaceutically acceptable salt, solvate, or prodrug thereof, wherein:

X is O, $SO_{0-2}$, or NR;

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

Z is O, $SO_{0-2}$, NR, $C(R^7)_2$, alkenyl or alkynyl;

$R^1$ is optionally substituted phenyl, optionally substituted 5- or 6-membered heteroaryl, or optionally substituted non-aromatic heterocyclic;

$R^4$ is H, $C(R^7)_2$, aryl, or heteroaryl;

$R^5$ is H, nitrile, an optionally substituted aryl, an optionally substituted heterocycle, optionally substituted $C_1$-$C_6$ alkyl, optionally substituted $C_3$-$C_9$ cycloalkyl, or

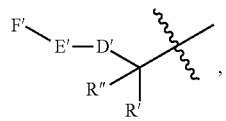

where

R' and R" are each independently selected from the group consisting of H, optionally substituted alkyl, —OR, halogen, —N(R)$_2$, optionally substituted cycloalkyl, and optionally substituted heterocyclyl;

or R' and R" may together form an optionally substituted 3- to 6-membered cycloalkyl or optionally substituted 3- to 6-membered non-aromatic heterocycle;

D' is selected from the group consisting of —O—, —NR—, —OCONR—, —OCO—, —NRSO$_2$—, —NRCO—, —NRSO$_2$NR—, —NRCOO—, —NR-CONR—, and —NRC(NR)NR—;

E' is selected from the group consisting of a bond, an optionally substituted $C_1$-$C_6$ alkyl, optionally substituted $C_1$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted $C_1$-$C_6$ alkyl, and optionally substituted cycloalkyl;

$R^6$ is independently selected from the group consisting of alkyl, —CF$_3$, —OR, —CN, —CO$_2$R, halogen, —SR, —SOR, —SO$_2$R, —SF$_5$, and —NR$_2$;

p is 0, 1, or 2;

$R^7$ is independently selected from the group consisting of H, halogen, optionally substituted $C_1$-$C_6$ alkyl, optionally substituted cycloalkyl, —OR, and —N(R); and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

4. A compound having a structure of Formula (Ic):

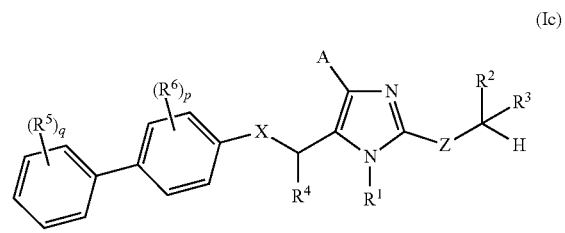

(Ic)

or a pharmaceutically acceptable salt, solvate, or prodrug thereof, wherein:

X is O, $SO_{0-2}$, or NR;

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

Z is O, $SO_{0-2}$, NR, $C(R^7)_2$, alkenyl or alkynyl;

$R^1$ is optionally substituted phenyl, optionally substituted 5- or 6-membered heteroaryl, or optionally substituted non-aromatic heterocyclic;

$R^4$ is H, $C(R^7)_2$, aryl, or heteroaryl;

$R^5$ is independently selected from the group consisting of NO$_2$, optionally substituted alkynyl, optionally substituted alkenyl, $C_{1-6}$ alkyl, —CF$_3$, —OR, —CN, —CO$_2$R, halogen, —SR, —SOR, —SO$_2$R, —SF$_5$, and —NR$_2$;

$R^6$ is independently selected from the group consisting of NO$_2$, optionally substituted alkynyl, optionally substituted alkenyl, alkyl, —CF$_3$, —OR, —CN, —CO$_2$R, halogen, —SR, —SOR, —SO$_2$R, —SF$_5$, and —NR$_2$;

p is 0, 1, or 2;

q is 0, 1, 2, 3, 4, or 5;

R is independently selected from the group consisting of H, optionally substituted $C_1$-$C_6$ alkyl, and optionally substituted cycloalkyl;

$R^7$ is independently selected from the group consisting of H, halogen, optionally substituted $C_1$-$C_6$ alkyl, optionally substituted cycloalkyl, —OR, and —N(R)$_2$; and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR.

5. The compound of claim 2, wherein:

(a) X is O or S; and/or (b) Y is selected from the group consisting of:

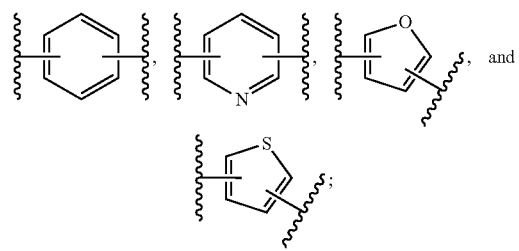

or (c) Y is phenylene optionally substituted with $C_1$-$C_6$ alkyl, cycloalkyl, —CF$_3$, —OR, —CN, —CO$_2$R, halogen, —SR, —SOR, —SO₂R, —SF₅, or —NR₂, or a combination of two or more thereof; and/or
(d) Z is selected from the group consisting of O, S and CH₂; and/or
(e) R⁵ is a phenyl optionally substituted with one or more alkyl, —OR, —CN, —CO₂R, halogen, —SR, —SOR, —SO₂R, —SF₅, and —NR₂, or any combination thereof, and/or
(f) R⁵ is a heterocycle optionally substituted with alkyl, —OR, —CN, —CO₂R, halogen, —SR, —SOR, —SO₂R, —SF₅ or —NR₂, or a combination of two or more thereof, and/or
(g) R¹ is optionally substituted pyridine; and/or
(h) R² and R³ together form a cyclopropyl, cyclopentyl or cyclohexene; and/or
(i) R² and R³ are independently optionally substituted C₁₋₆ alkyl; and/or
(j) A is H, halogen, nitrile, optionally substituted alkyl, optionally substituted alkenyl, optionally substituted alkynyl, —CON(R)₂, or —COOR; and/or
(k) A is H.

6. The compound of claim 3, wherein:
(a) X is O or S; and/or
(b) Z is selected from the group consisting of O, S and CH₂; and/or
(c) R⁵ is a phenyl optionally substituted with one or more alkyl, —OR, —CN, —CO₂R, halogen, —SR, —SOR, —SO₂R, —SF₅, and —NR₂, or any combination thereof, and/or
(d) R⁵ is a heterocycle optionally substituted with alkyl, —OR, —CN, —CO₂R, halogen, —SR, —SOR, —SO₂R, —SF₅ or —NR₂, or a combination of two or more thereof, and/or
(e) R¹ is optionally substituted pyridine; and/or
(f) R² and R³ together form a cyclopropyl, cyclopentyl or cyclohexene; and/or
(g) R² and R³ are independently optionally substituted C₁₋₆ alkyl; and/or
(h) A is H, halogen, nitrile, optionally substituted alkyl, optionally substituted alkenyl, optionally substituted alkynyl, —CON(R)₂, or —COOR; and/or
(i) A is H.

7. The compound of claim 4, wherein:
(a) X is O or S; and/or
(b) Z is selected from the group consisting of O, S and CH₂; and/or
(c) R¹ is optionally substituted pyridine; and/or
(d) R² and R³ together form a cyclopropyl, cyclopentyl or cyclohexene; and/or
(e) R² and R³ are independently optionally substituted C₁₋₆ alkyl; and/or
(f) A is H, halogen, nitrile, optionally substituted alkyl, optionally substituted alkenyl, optionally substituted alkynyl, —CON(R)₂, or —COOR; and/or
(g) A is H.

8. A compound selected from the group consisting of:
(a) a compound having a structure of Formula (Ia):

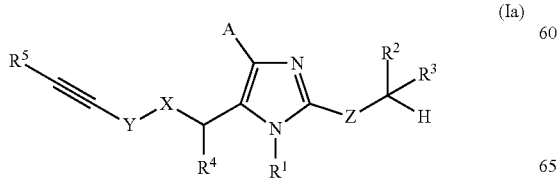

or a pharmaceutically acceptable salt, solvate, or prodrug thereof, wherein:
X is O, SO₀₋₂, NR, or C(R⁷)₂;
Y is optionally substituted aryl, optionally substituted alkyl, optionally substituted alkenyl, alkynyl, optionally substituted heteroaryl, optionally substituted cycloalkyl, or optionally substituted non-aromatic heterocyclyl;
R² and R³ are independently H, optionally substituted C₁₋₆ alkyl, optionally substituted C₁₋₉ cyclic, optionally substituted C₃₋₉ heterocyclyl, or halogen, or R² and R³ together form an optionally substituted C₃₋₉ cyclic or optionally substituted 3- to 9-membered heterocyclyl ring;
Z is O, SO₀₋₂, NR, C(R⁷)₂, alkenyl or alkynyl;
R¹ is optionally substituted phenyl, optionally substituted 5- or 6-membered heteroaryl, or optionally substituted non-aromatic heterocyclic;
R⁴ is H, C(R⁷)₂, aryl, or heteroaryl;
R⁵ is

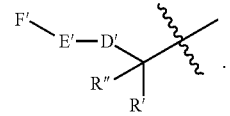

where
R' and R" are each independently selected from the group consisting of H, optionally substituted alkyl, —OR, halogen, —N(R)₂, optionally substituted cycloalkyl, and optionally substituted heterocyclyl;
or R' and R" may together form an optionally substituted 3- to 6-membered cycloalkyl or optionally substituted 3- to 6-membered non-aromatic heterocycle;
D' is selected from the group consisting of —O—, —NR—, —OCONR—, —OCO—, —NRSO₂—, —NRCO—, —NRSO₂NR—, —NRCOO—, —NRCONR—, and —NRC(NR)NR—;
E' is selected from the group consisting of a bond, an optionally substituted C1-C6 alkyl, optionally substituted C₁-C₆ alkenyl, and optionally substituted cycloalkyl; and
F' is selected from the group consisting of H, an optionally substituted cycloalkyl, an optionally substituted non-aromatic heterocycle, an optionally substituted aryl, and an optionally substituted heteroaryl;
R is independently selected from the group consisting of H, optionally substituted C₁-C₆ alkyl, and optionally substituted cycloalkyl;
R⁷ is independently selected from the group consisting of H, halogen, optionally substituted C₁-C₆ alkyl, optionally substituted cycloalkyl, —OR, and —N(R); and
A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)₂, or —COOR;
provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate; and (b) a compound having a structure of Formula (Ib):

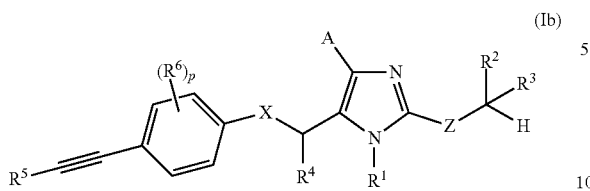

or a pharmaceutically acceptable salt, solvate, or prodrug thereof, wherein:

X is O, $SO_{0-2}$, or NR;

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

Z is O, $SO_{0-2}$, NR, $C(R^7)_2$, alkenyl or alkynyl;

$R^1$ is optionally substituted phenyl, optionally substituted 5- or 6-membered heteroaryl, or optionally substituted non-aromatic heterocyclic;

$R^4$ is H, $C(R^7)_2$, aryl, or heteroaryl;

$R^5$

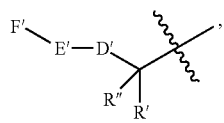

where

R' and R" are each independently selected from the group consisting of H, optionally substituted alkyl, —OR, halogen, —N(R)$_2$, optionally substituted cycloalkyl, and optionally substituted heterocyclyl; or R' and R" may together form an optionally substituted 3- to 6-membered cycloalkyl or optionally substituted 3- to 6-membered non-aromatic heterocycle;

D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;

E' is selected from the group consisting of a bond, an optionally substituted C1-C6 alkyl, optionally substituted $C_1$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted $C_1$-$C_6$ alkyl, and optionally substituted cycloalkyl;

$R^6$ is independently selected from the group consisting of alkyl, —CF$_3$, —OR, —CN, —CO$_2$R, halogen, —SR, —SOR, —SO$_2$R, —SF$_5$, and —NR$_2$;

p is 0, 1, or 2;

$R^7$ is independently selected from the group consisting of H, halogen, optionally substituted $C_1$-$C_6$ alkyl, optionally substituted cycloalkyl, —OR, and —N(R); and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

9. The compound of claim 8 or 1 wherein:

(a) R' and R" together form a 3- to 6-membered cycloalkyl or 3- to 6-membered non-aromatic heterocycle; or (b) R' and R" are each H, or at least one of R' and R" is methyl and any remaining R' or R" is H; and/or (c) at least one of R' and R" is an optionally substituted alkyl; and/or (d) E' is a $C_1$-$C_6$ alkyl and F' is H; and/or (e) F' is an optionally substituted cycloalkyl selected from: cyclopropyl, cyclobutyl, cyclopentyl, and cyclohexyl; and/or (f) F' is an optionally substituted heterocycle selected from: morpholine, azetidine, alkyl-piperidine, alkyl-piperazine, alkyl-diazepane, thiomorpholine 1,1-dioxide, isoindoline-1,3-dione, tetrahydropyran, and pyrrolidone; and/or (g) F' is an optionally substituted aryl selected from: phenyl, optionally substituted with alkyl, —CF$_3$, —OR, —CN, —CO$_2$R, halogen, —SR, —SOR, —SO$_2$R, —SF$_5$ or —NR$_2$, or a combination of two or more thereof, and/or (h) F' is an optionally substituted heteroaryl selected from: alkyl-triazole, tetrazole, imidazole, and isoxazole; and/or (i) D' is —O—, —NH—, —OCONH—, —OCO—, —NHCO—, or —NHCOO—.

10. A compound of Formula (IIa):

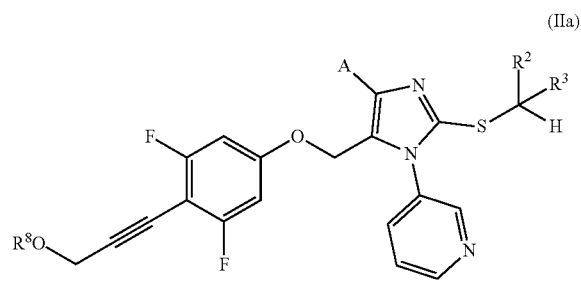

or a pharmaceutically acceptable salt, solvate, or prodrug thereof, wherein:

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

R is independently selected from the group consisting of H, optionally substituted $C_1$-$C_6$ alkyl, and optionally substituted cycloalkyl; and $R^8$ is selected from the group consisting of H,

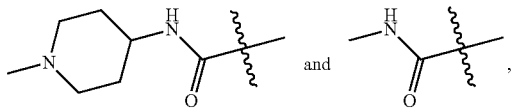

wherein ⧘ indicates a point of attachment to O.

11. A compound of Formula (IIb):

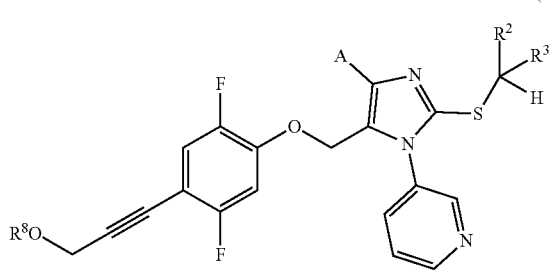

or a pharmaceutically acceptable salt, solvate, or prodrug thereof, wherein:

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

R is independently selected from the group consisting of H, optionally substituted $C_1$-$C_6$ alkyl, and optionally substituted cycloalkyl; and $R^8$ is selected from the group consisting of H,

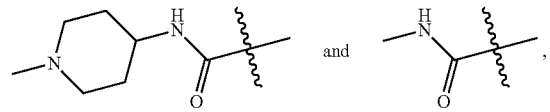

wherein ⧘ indicates a point of attachment to O.

12. The compound of claim 10, wherein:
(a) $R^2$ and $R^3$ together form a cyclopropyl, cyclopentyl or cyclohexene; or
(b) $R^2$ and $R^3$ are independently optionally substituted $C_{1-6}$ alkyl; and/or
(c) A is H, halogen, nitrile, optionally substituted alkyl, optionally substituted alkenyl, optionally substituted alkynyl, —CON(R)$_2$, or —COOR.

13. The compound of claim 11, wherein:
(a) $R^2$ and $R^3$ together form a cyclopropyl, cyclopentyl or cyclohexene; or
(b) $R^2$ and $R^3$ are independently optionally substituted $C_{1-6}$ alkyl; and/or
(c) A is H, halogen, nitrile, optionally substituted alkyl, optionally substituted alkenyl, optionally substituted alkynyl, —CON(R)$_2$, or —COOR.

14. A compound of Formula (III):

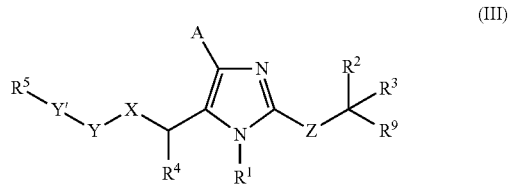

or a pharmaceutically acceptable salt, solvate, or prodrug thereof, wherein:

X is O, SO$_{0-2}$, or C(R$^7$)$_2$;

Y is optionally substituted aryl, optionally substituted alkenyl, alkynyl, optionally substituted heteroaryl, optionally substituted cycloalkyl, or optionally substituted non-aromatic heterocyclyl;

Y' is alkynyl, optionally substituted aryl, optionally substituted heteroaryl, optionally substituted cycloalkyl, optionally substituted non-aromatic heterocyclyl, or a bond;

$R^2$ and $R^3$ are independently H, optionally substituted $C_{1-6}$ alkyl, optionally substituted $C_{1-9}$ cyclic, optionally substituted $C_{3-9}$ heterocyclyl, or halogen, or $R^2$ and $R^3$ together form an optionally substituted $C_{3-9}$ cyclic or optionally substituted 3- to 9-membered heterocyclyl ring;

Z is O, SO$_{0-2}$, NR, C(R$^7$)$_2$, alkenyl or alkynyl;

$R^1$ is optionally substituted phenyl, optionally substituted 5- or 6-membered heteroaryl, or optionally substituted non-aromatic heterocyclic;

$R^4$ is H, C(R$^7$)$_2$, aryl, or heteroaryl;

$R^5$ is H, nitrile, an optionally substituted aryl, an optionally substituted heterocycle, optionally substituted $C_1$-$C_6$ alkyl, optionally substituted $C_3$-$C_9$ cycloalkyl, or

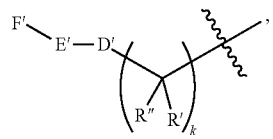

where
k is 1, 2, 3, 4, or 5; R' and R" are each independently selected from the group consisting of H, optionally substituted alkyl, —OR, halogen, —N(R)$_2$, optionally substituted cycloalkyl, and optionally substituted heterocyclyl;

or R' and R" may together form an optionally substituted 3- to 6-membered cycloalkyl or optionally substituted 3- to 6-membered non-aromatic heterocycle;

D' is selected from the group consisting of —O—, —NR—, —OCONR—, —OCO—, —CO—, —CO(NR)—, —SO$_{0-2}$—, —SO$_{0-2}$NR—, —NRSO$_2$—, —NRCO—, —NRSO$_2$NR—, —NRCOO—, —NRCONR—, and —NRC(NR)NR—;

E' is selected from the group consisting of a bond, an optionally substituted C1-C6 alkyl, optionally substituted C$_1$-C$_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted C$_1$-C$_6$ alkyl, and optionally substituted cycloalkyl;

R$^7$ is independently selected from the group consisting of H, halogen, optionally substituted C$_1$-C$_6$ alkyl, optionally substituted cycloalkyl, —OR, and —N(R); and A is H, halogen, nitrile, optionally substituted alkyl, optionally substituted alkenyl, optionally substituted alkynyl, optionally substituted cycloalkyl, optionally substituted aryl, optionally substituted heteroaryl, optionally substituted non-aromatic heterocyclyl, —COR, —CON(R)$_2$, or —COOR;

R$^9$ is H, nitrile, halogen, —C(O)(optionally substituted alkyl), optionally substituted heterocycle, optionally substituted cyclic ring, or optionally substituted alkyl;

provided that the compound is not 3-(4-((2-(cyclohex-2-en-1-ylthio)-1-(pyridin-3-yl)-1H-imidazol-5-yl)methoxy)-2-methylphenyl)prop-2-yn-1-yl (2-(4-isopropylpiperazin-1-yl)ethyl)carbamate.

15. A compound selected from the group consisting of:

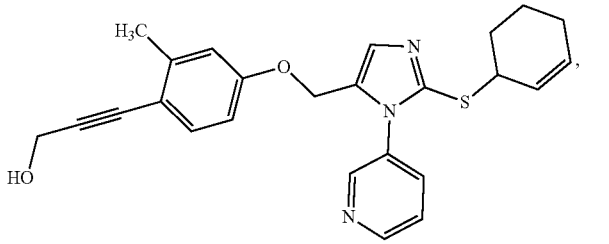

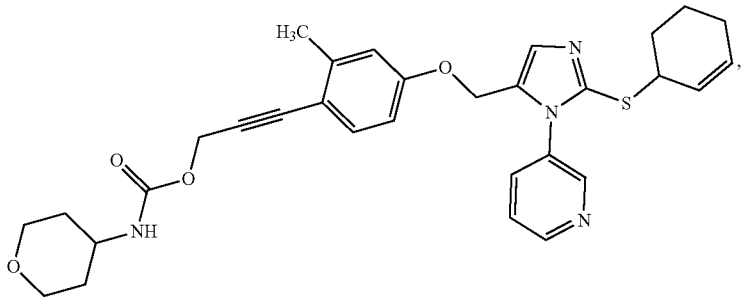

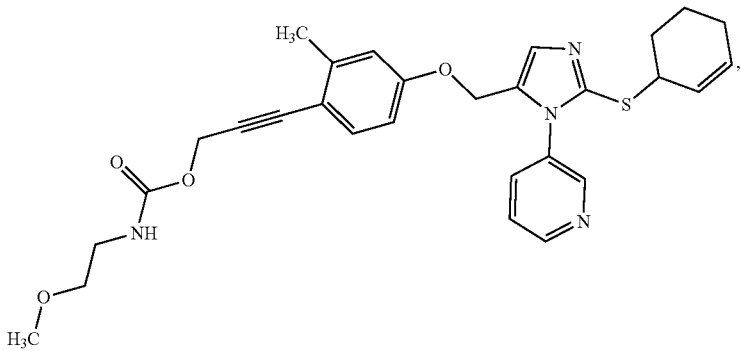

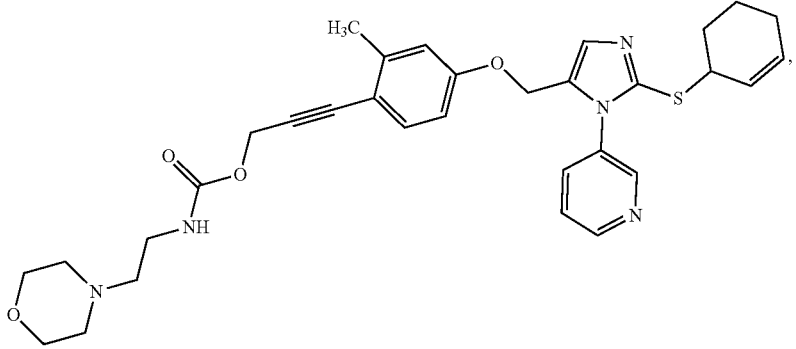

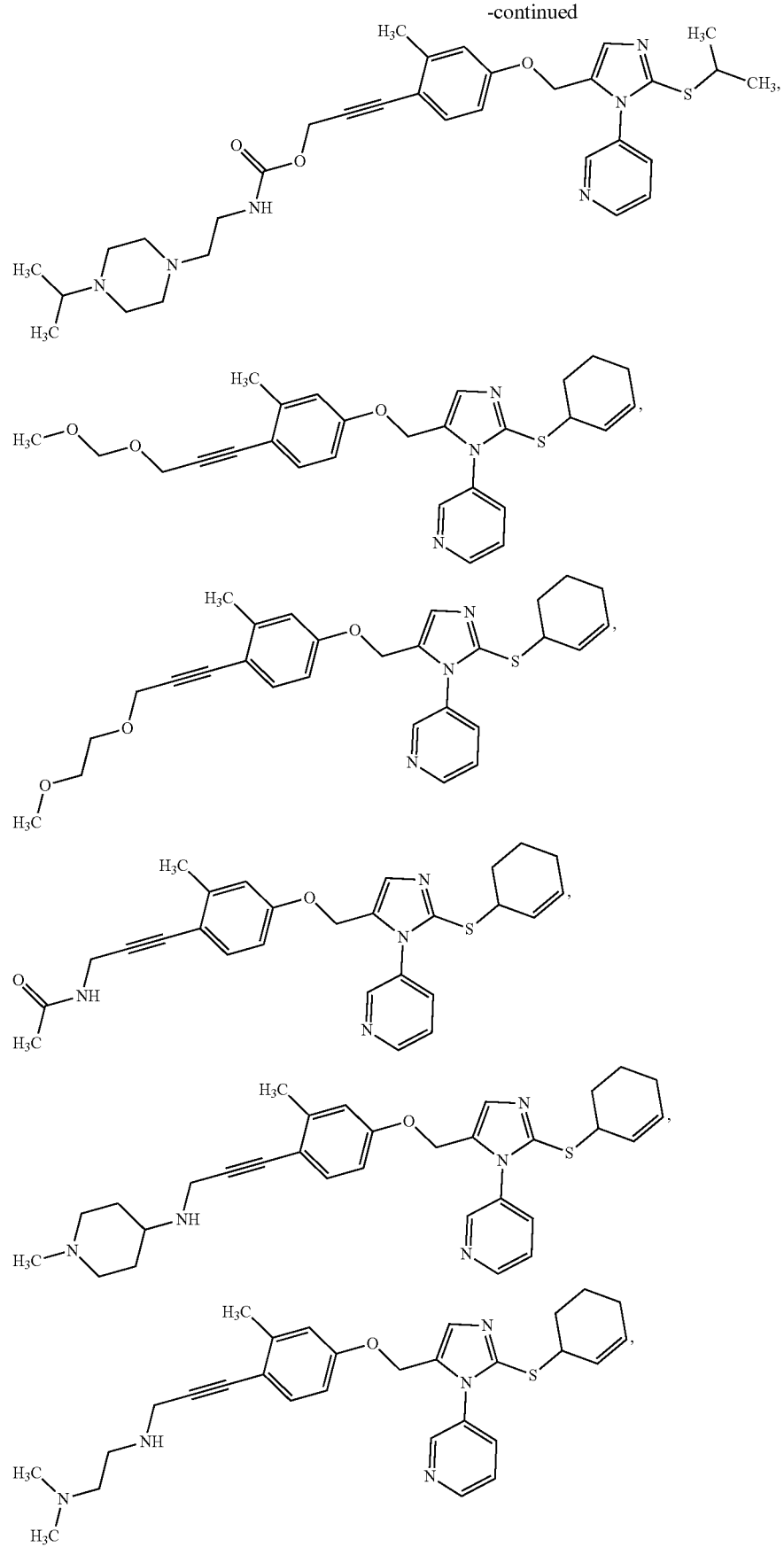

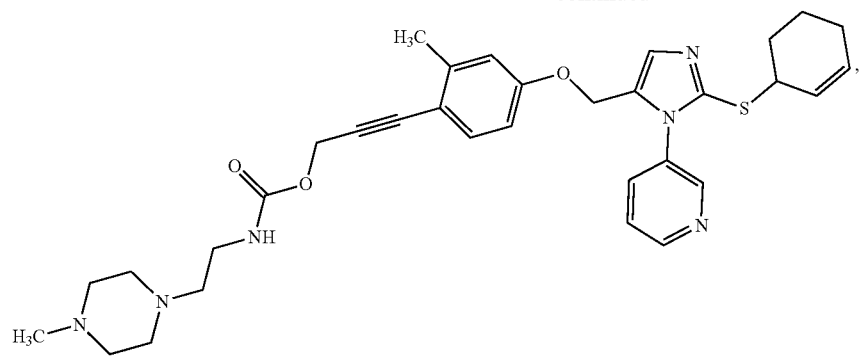
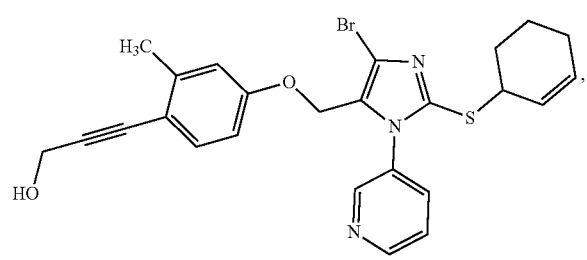
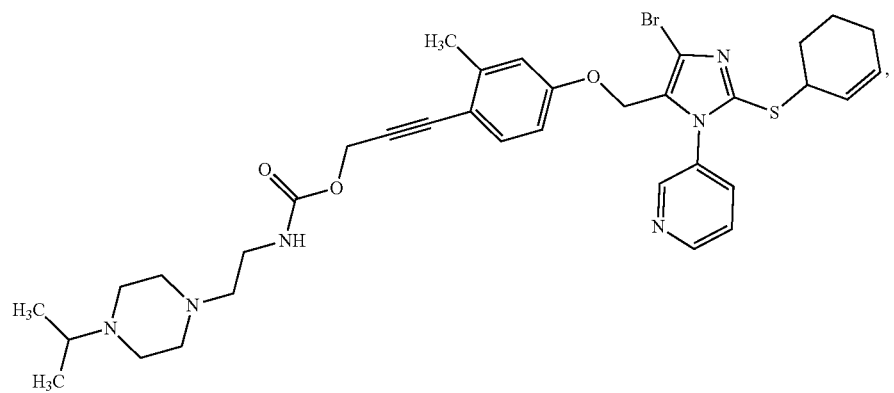
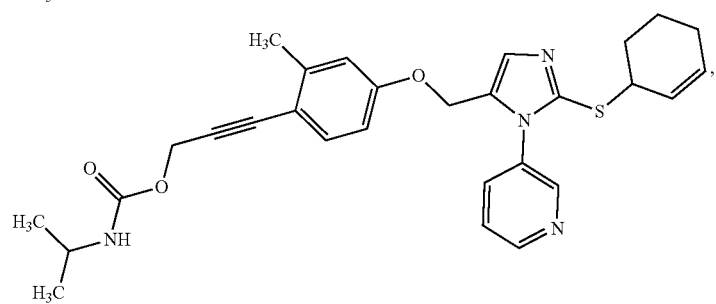
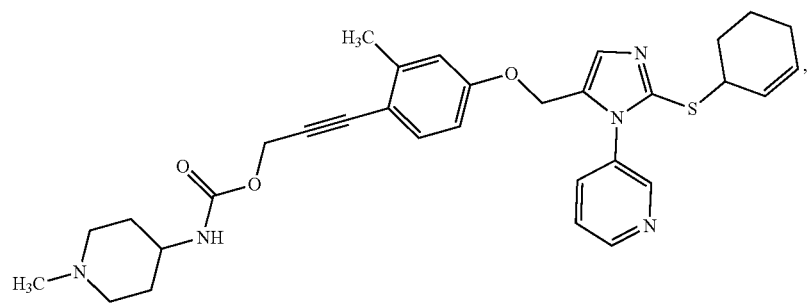

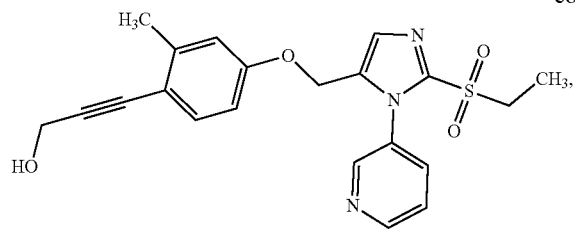
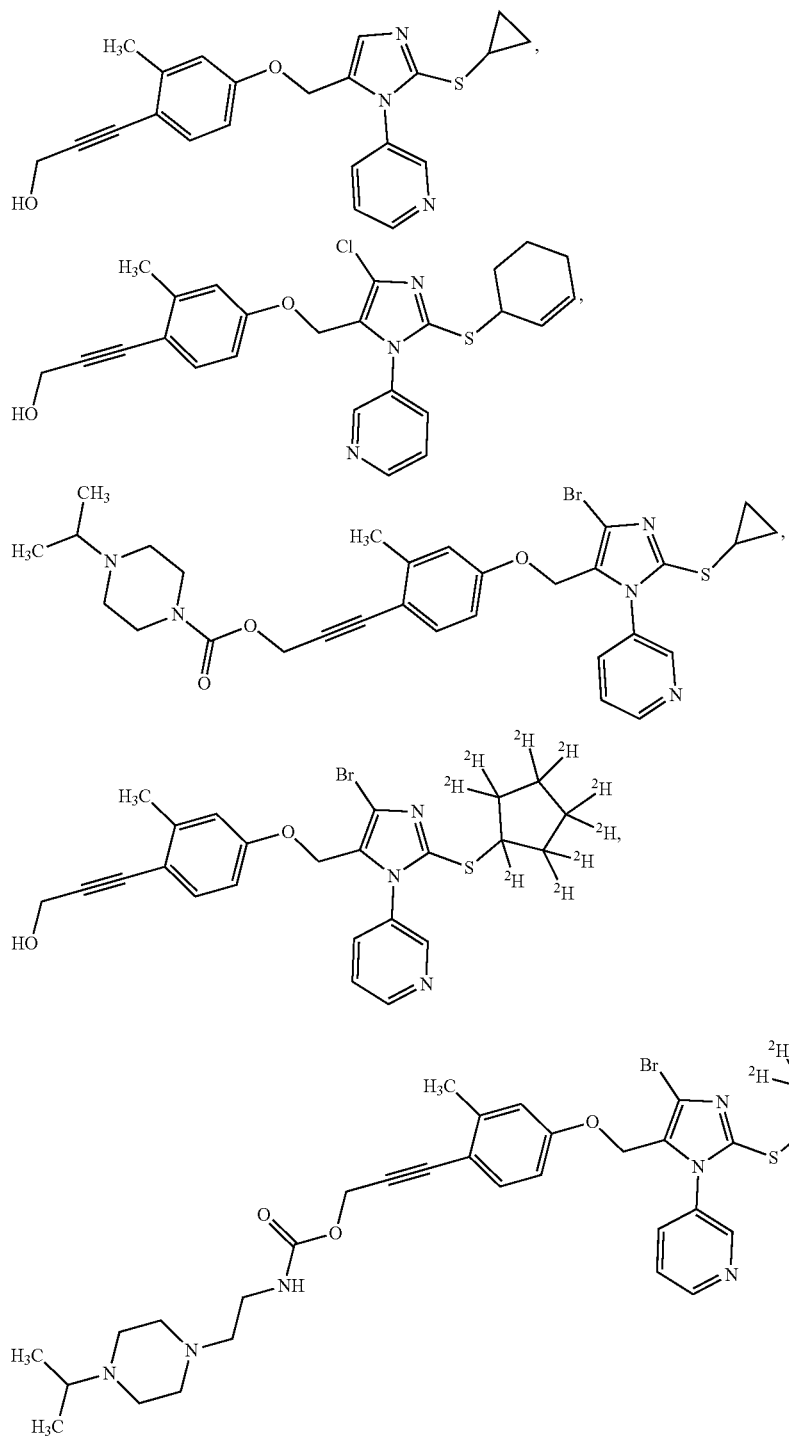

-continued
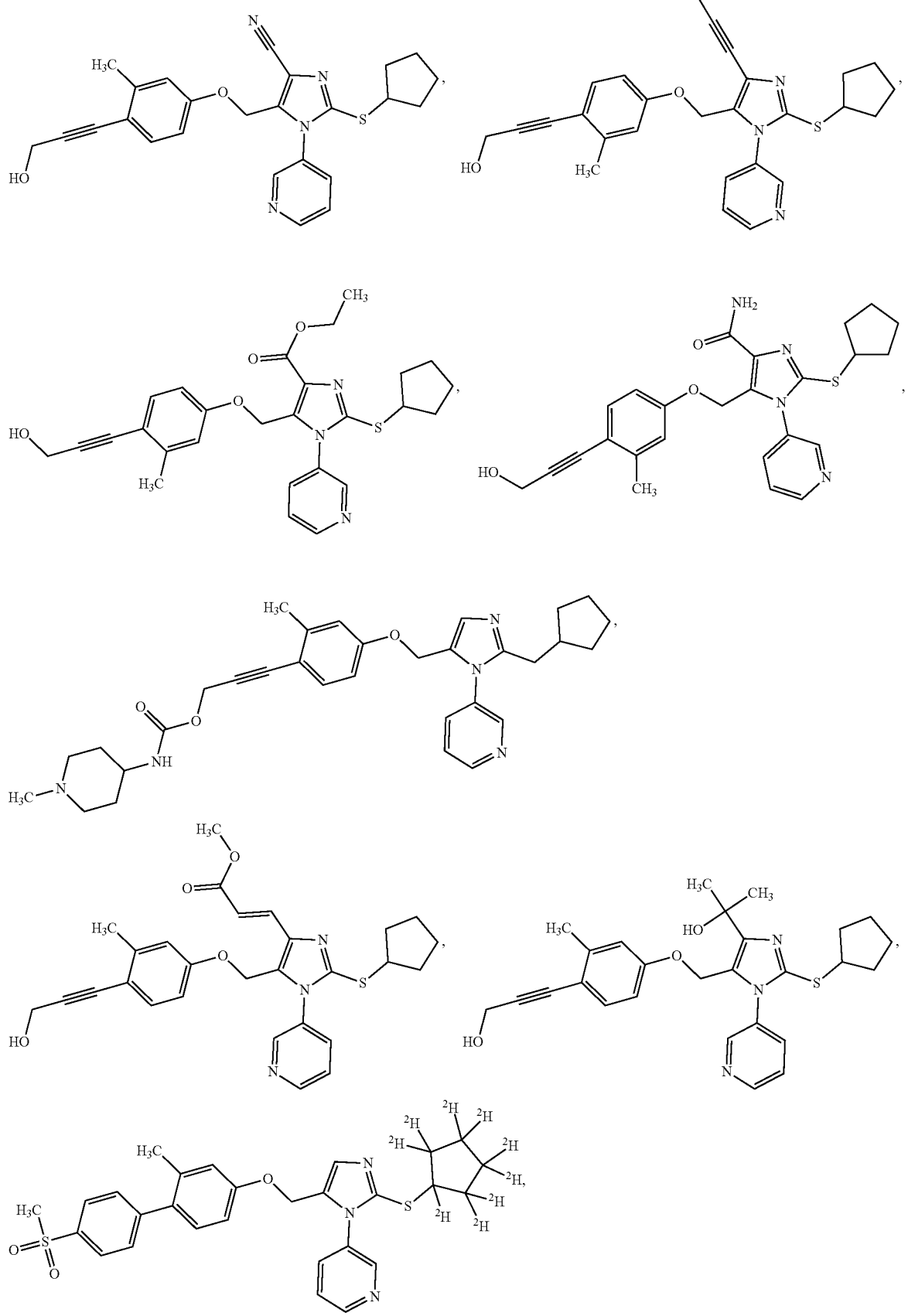

-continued
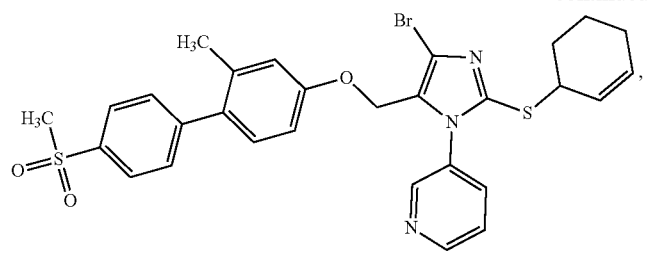
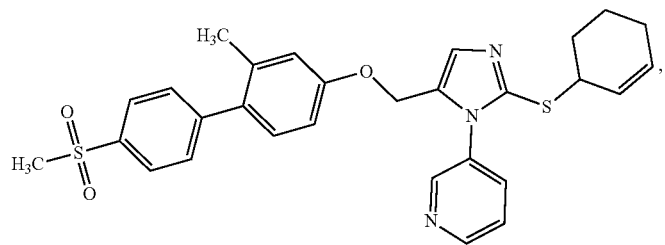
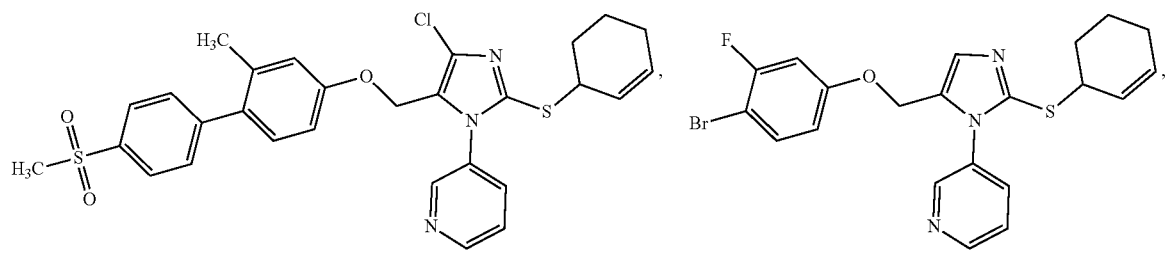
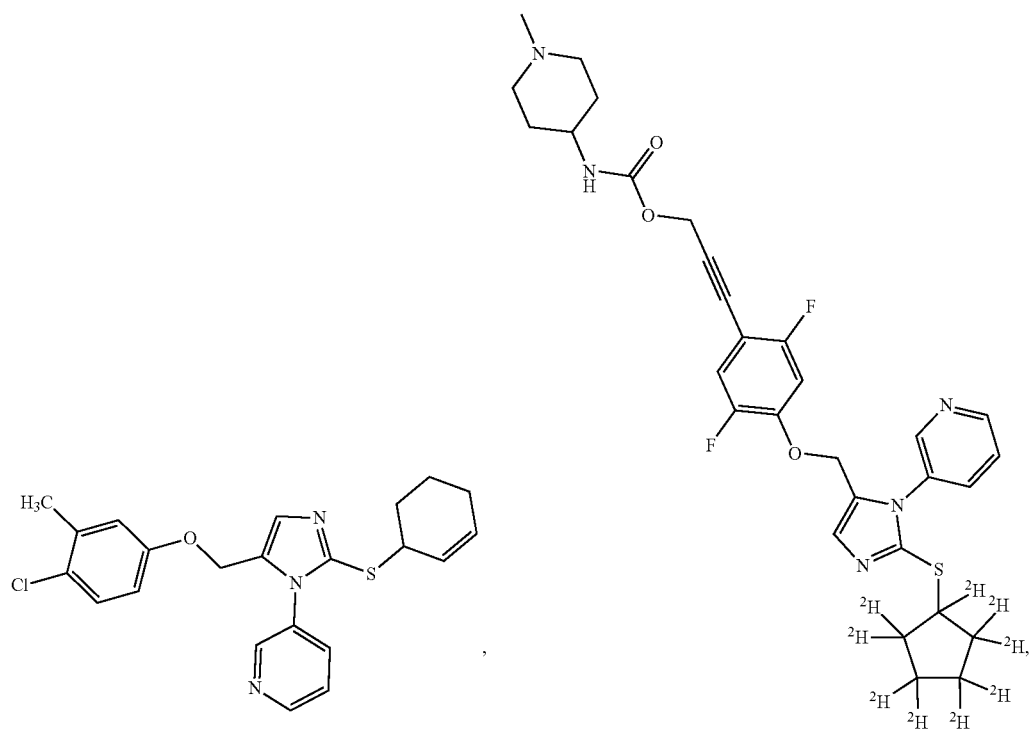

-continued
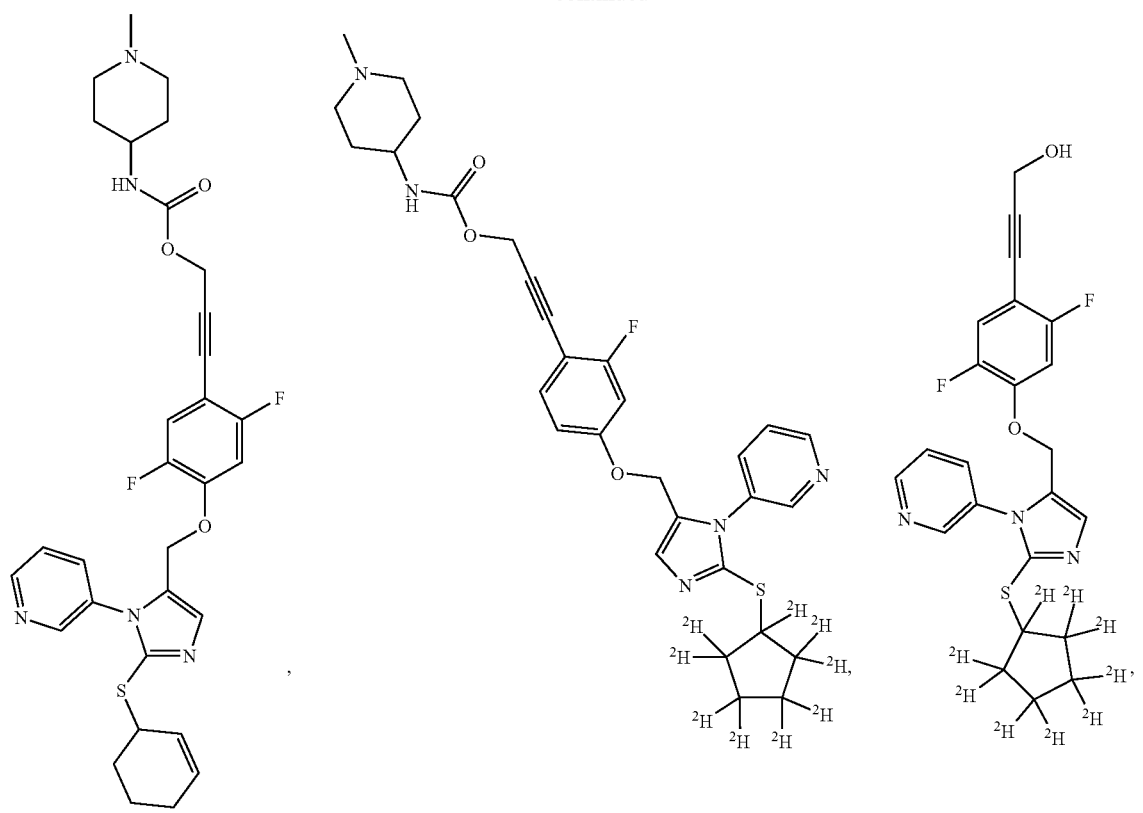
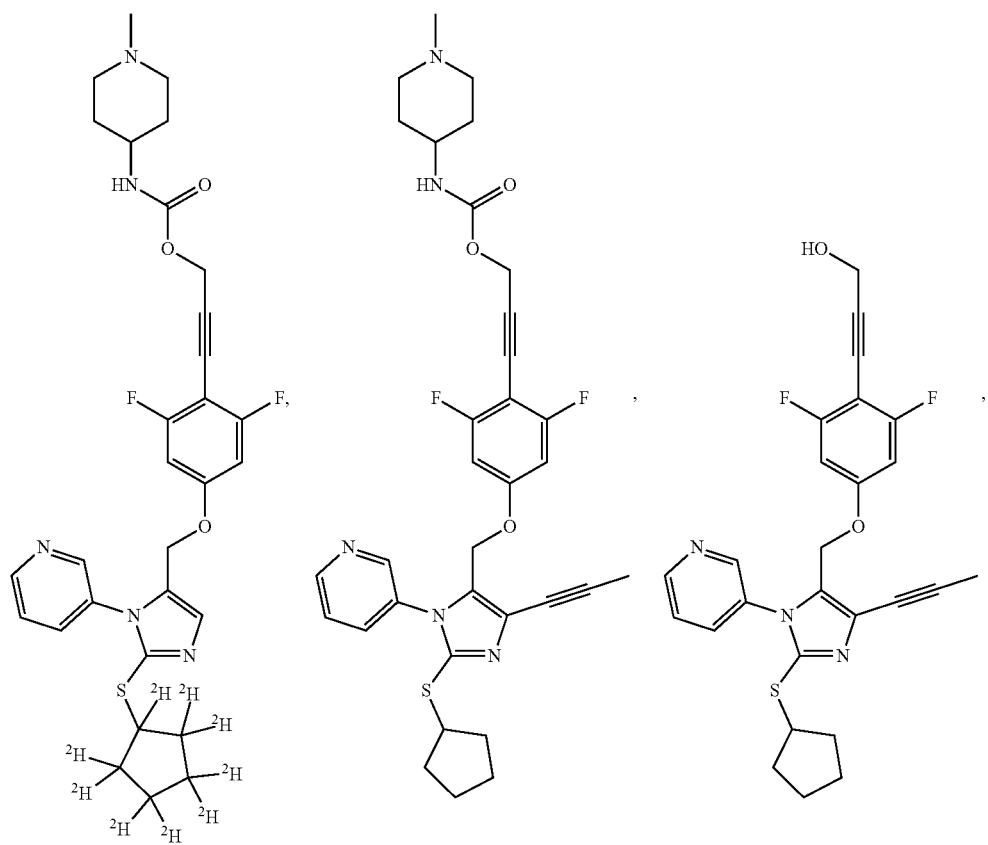

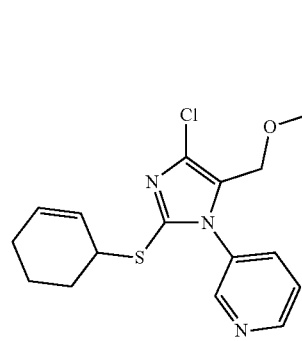
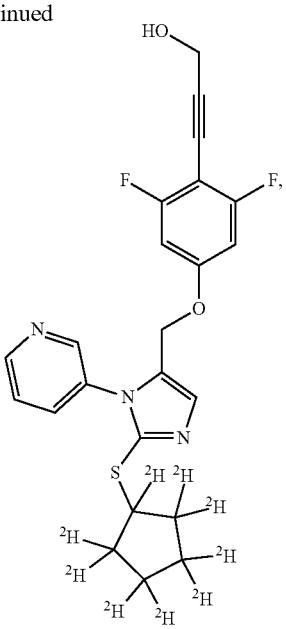
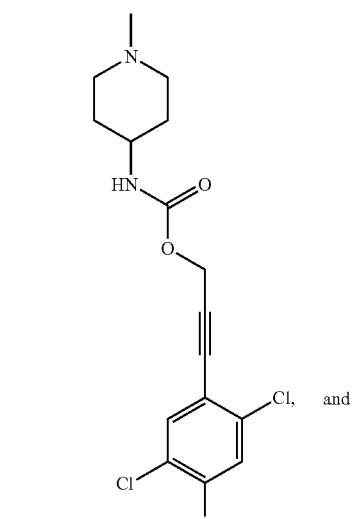
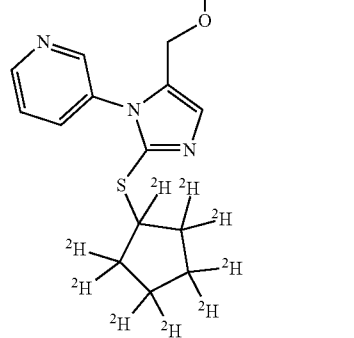

or a pharmaceutically acceptable salt, solvate, or prodrug thereof.

16. A pharmaceutical composition comprising a compound of claim 1, and at least one pharmaceutically acceptable excipient.

17. A pharmaceutical composition comprising a compound of claim 2, and at least one pharmaceutically acceptable excipient.

18. A pharmaceutical composition comprising a compound of claim 3, and at least one pharmaceutically acceptable excipient.

19. A pharmaceutical composition comprising a compound of claim 4, and at least one pharmaceutically acceptable excipient.

20. A pharmaceutical composition comprising a compound of claim 10, and at least one pharmaceutically acceptable excipient.

21. A pharmaceutical composition comprising a compound of claim 11, and at least one pharmaceutically acceptable excipient.

22. A pharmaceutical composition comprising a compound of claim 14, and at least one pharmaceutically acceptable excipient.

* * * * *